US008574253B2

(12) United States Patent
Gruber et al.

(10) Patent No.: US 8,574,253 B2
(45) Date of Patent: Nov. 5, 2013

(54) METHOD, SYSTEM AND DEVICE FOR TISSUE REMOVAL

(75) Inventors: William Harwick Gruber, Southborough, MA (US); Ronald David Adams, Holliston, MA (US); Albert Chun-Chi Chin, Newton, MA (US); Eric Karl Litscher, Hopkinton, MA (US); Roy Hewitt Sullivan, Uxbridge, MA (US); Paul DiCesare, Easton, CT (US); Jeffrey Radziunas, Wallingford, CT (US); Daniel Vigliotti, Hamden, CT (US); Bryan Dale Knodel, Flagstaff, AZ (US); Chris Scott Daniels, Columbus, OH (US); Kevin J. Vititoe, Columbus, OH (US); Michael Anthony Lorenz, Gahanna, OH (US); Paul P. Kolada, Bexley, OH (US); Ryan Scott Crisp, Lewis Center, OH (US); Chris William Cicenas, Pataskala, OH (US); Ludwin M. Mora, Pataskala, OH (US); Brent Lee Burchfield, Powell, OH (US)

(73) Assignee: Hologic, Inc., Marlborough, MA (US)

( * ) Notice: Subject to any disclaimer, the term of this patent is extended or adjusted under 35 U.S.C. 154(b) by 966 days.

(21) Appl. No.: 12/098,250

(22) Filed: Apr. 4, 2008

(65) Prior Publication Data

US 2008/0249553 A1    Oct. 9, 2008

Related U.S. Application Data

(60) Provisional application No. 60/910,618, filed on Apr. 6, 2007, provisional application No. 60/910,625, filed on Apr. 6, 2007, provisional application No. 60/986,912, filed on Nov. 9, 2007.

(51) Int. Cl.
*A61B 17/32* (2006.01)

(52) U.S. Cl.
USPC .......................................... 606/171

(58) Field of Classification Search
USPC ............. 606/170, 171, 79–85, 159, 166, 167, 606/169, 177, 178, 110–115, 127, 128; 604/22; 600/564, 565, 567
See application file for complete search history.

(56) References Cited

U.S. PATENT DOCUMENTS

| | | | |
|---|---|---|---|
| 2,708,437 A | 5/1955 | Hutchins | |
| 2,849,002 A | 8/1958 | Oddo et al. | |

(Continued)

FOREIGN PATENT DOCUMENTS

| | | |
|---|---|---|
| EP | 0010650 | 5/1980 |
| EP | 0044877 | 2/1982 |

(Continued)

OTHER PUBLICATIONS

International Search Report and Written Opinion Received in PCT/US07/79449 Dated Jan. 28, 2008.

(Continued)

*Primary Examiner* — S. Thomas Hughes
*Assistant Examiner* — Tin Nguyen
(74) *Attorney, Agent, or Firm* — Vista IP Law Group LLP

(57) ABSTRACT

A method and device for tissue removal. The device may be used to remove uterine fibroids and other abnormal gynecological tissue. According to one embodiment, the device includes a housing, an outer tube, and an inner tube. The outer tube is fixed to the housing and includes a side window proximate to its distal end. The side window may have sloped proximal and distal ends. The inner tube has a distal end positioned within the outer tube, the distal end being adapted to rotate and, at the same time, to move back and forth past the side window, with the rotational and translational movement of the inner tube being independently controllable. The distal end of the inner tube may have an external bevel. Suction is applied to the proximal end of the inner tube to draw tissue into the side window and to remove resected tissue through the inner tube.

11 Claims, 50 Drawing Sheets

(56) References Cited

U.S. PATENT DOCUMENTS

| | | | |
|---|---|---|---|
| 3,369,034 A | 2/1968 | Chalmers et al. | |
| 3,561,429 A | 2/1971 | Jewett | |
| 4,040,311 A | 8/1977 | Page, Jr. et al. | |
| 4,188,952 A | 2/1980 | Loschilov et al. | |
| 4,198,981 A | 4/1980 | Sinnreich | |
| 4,203,444 A | 5/1980 | Bonnell et al. | |
| 4,246,902 A | 1/1981 | Martinez | |
| 4,261,360 A | 4/1981 | Perez | |
| 4,316,465 A | 2/1982 | Dotson, Jr. | |
| 4,598,698 A | 7/1986 | Siegmund | |
| 4,598,710 A | 7/1986 | Klienberg et al. | |
| 4,650,462 A | 3/1987 | DeSatnick et al. | |
| 4,662,869 A | 5/1987 | Wright | |
| 4,673,393 A | 6/1987 | Suzuki et al. | |
| 4,700,694 A | 10/1987 | Shishido | |
| 4,729,763 A | 3/1988 | Henrie | |
| 4,844,088 A * | 7/1989 | Kambin | 600/566 |
| 4,848,323 A | 7/1989 | Marijnissen et al. | |
| 4,850,423 A | 7/1989 | Allen et al. | |
| 4,895,565 A | 1/1990 | Hillstead | |
| RE33,258 E | 7/1990 | Onik et al. | |
| 4,949,718 A | 8/1990 | Neuwirth et al. | |
| 4,998,527 A | 3/1991 | Meyer | |
| 5,078,725 A | 1/1992 | Enderle et al. | |
| 5,104,377 A | 4/1992 | Levine | |
| 5,108,414 A | 4/1992 | Enderle et al. | |
| 5,125,903 A | 6/1992 | McLaughlin et al. | |
| 5,163,433 A | 11/1992 | Kagawa et al. | |
| 5,163,949 A | 11/1992 | Bonutti | |
| 5,176,628 A | 1/1993 | Charles et al. | |
| 5,183,031 A | 2/1993 | Rossoff | |
| 5,195,541 A | 3/1993 | Obenchain | |
| 5,201,756 A | 4/1993 | Horzewski et al. | |
| 5,222,971 A | 6/1993 | Willard et al. | |
| 5,246,016 A | 9/1993 | Lieber et al. | |
| 5,259,836 A | 11/1993 | Thurmond et al. | |
| 5,269,798 A | 12/1993 | Winkler | |
| 5,275,609 A | 1/1994 | Pingleton et al. | |
| 5,304,115 A | 4/1994 | Pflueger et al. | |
| 5,320,091 A | 6/1994 | Grossi et al. | |
| 5,334,183 A | 8/1994 | Wuchinich | |
| 5,350,390 A | 9/1994 | Sher | |
| 5,361,752 A | 11/1994 | Moll et al. | |
| 5,377,668 A | 1/1995 | Ehmsen et al. | |
| 5,392,765 A | 2/1995 | Muller | |
| 5,402,772 A | 4/1995 | Moll et al. | |
| 5,403,276 A | 4/1995 | Schechter et al. | |
| 5,423,844 A | 6/1995 | Miller | |
| 5,443,470 A | 8/1995 | Stern et al. | |
| 5,450,843 A | 9/1995 | Moll et al. | |
| 5,458,112 A | 10/1995 | Weaver | |
| 5,472,439 A | 12/1995 | Hurd | |
| 5,484,401 A | 1/1996 | Rodriguez et al. | |
| 5,490,860 A | 2/1996 | Middle et al. | |
| 5,503,626 A | 4/1996 | Goldrath | |
| 5,505,730 A | 4/1996 | Edwards | |
| 5,514,091 A | 5/1996 | Yoon | |
| 5,522,790 A | 6/1996 | Moll et al. | |
| 5,526,822 A | 6/1996 | Burbank et al. | |
| 5,540,658 A | 7/1996 | Evans et al. | |
| 5,575,788 A | 11/1996 | Baker et al. | |
| 5,601,583 A | 2/1997 | Donahue et al. | |
| 5,602,449 A | 2/1997 | Krause et al. | |
| 5,618,296 A | 4/1997 | Sorensen et al. | |
| 5,624,395 A | 4/1997 | Mikhail et al. | |
| 5,624,399 A | 4/1997 | Ackerman | |
| 5,656,013 A | 8/1997 | Yoon | |
| 5,685,840 A * | 11/1997 | Schechter et al. | 604/22 |
| 5,695,511 A * | 12/1997 | Cano et al. | 606/170 |
| 5,697,940 A | 12/1997 | Chu et al. | |
| 5,709,664 A | 1/1998 | Vandenbroek et al. | |
| 5,725,525 A | 3/1998 | Kordis | |
| 5,730,725 A | 3/1998 | Yoon | |
| 5,738,629 A | 4/1998 | Moll et al. | |
| 5,741,287 A | 4/1998 | Alden et al. | |
| 5,743,850 A | 4/1998 | Moll et al. | |
| 5,743,851 A | 4/1998 | Moll et al. | |
| 5,749,845 A | 5/1998 | Hildebrand et al. | |
| 5,749,889 A | 5/1998 | Bacich et al. | |
| 5,755,731 A | 5/1998 | Grinberg | |
| 5,775,333 A | 7/1998 | Burbank et al. | |
| 5,782,800 A | 7/1998 | Yoon | |
| 5,800,493 A | 9/1998 | Stevens et al. | |
| 5,807,401 A * | 9/1998 | Grieshaber et al. | 606/107 |
| 5,823,945 A | 10/1998 | Moll et al. | |
| 5,823,971 A | 10/1998 | Robinson et al. | |
| 5,843,046 A | 12/1998 | Motisi et al. | |
| 5,855,549 A | 1/1999 | Newman | |
| 5,857,585 A | 1/1999 | Tolkoff et al. | |
| 5,865,728 A | 2/1999 | Moll et al. | |
| 5,873,815 A | 2/1999 | Kerin et al. | |
| 5,891,134 A | 4/1999 | Goble et al. | |
| 5,899,915 A | 5/1999 | Saadat | |
| 5,902,251 A | 5/1999 | vanHooydonk | |
| 5,904,649 A | 5/1999 | Andrese | |
| 5,904,680 A | 5/1999 | Kordis et al. | |
| 5,911,739 A | 6/1999 | Kordis et al. | |
| 5,916,198 A | 6/1999 | Dillow | |
| 5,928,161 A | 7/1999 | Krulevitch et al. | |
| 5,954,714 A | 9/1999 | Saadat et al. | |
| 5,954,715 A | 9/1999 | Harrington et al. | |
| 5,961,444 A | 10/1999 | Thompson | |
| 5,961,532 A | 10/1999 | Finley et al. | |
| 5,964,755 A | 10/1999 | Edwards | |
| 5,964,777 A | 10/1999 | Drucker | |
| 5,972,000 A | 10/1999 | Beyar et al. | |
| 5,979,494 A | 11/1999 | Perkins et al. | |
| 6,002,968 A | 12/1999 | Edwards | |
| 6,017,316 A | 1/2000 | Ritchart et al. | |
| 6,032,673 A | 3/2000 | Savage et al. | |
| 6,039,748 A | 3/2000 | Savage et al. | |
| 6,042,590 A | 3/2000 | Sporri et al. | |
| 6,068,626 A | 5/2000 | Harrington et al. | |
| 6,080,129 A | 6/2000 | Blaisdell | |
| 6,086,544 A | 7/2000 | Hibner et al. | |
| 6,099,541 A | 8/2000 | Klopotek | |
| 6,117,070 A | 9/2000 | Akiba | |
| 6,119,973 A | 9/2000 | Galloway | |
| 6,126,635 A | 10/2000 | Simpson et al. | |
| 6,139,570 A | 10/2000 | Saadat et al. | |
| 6,149,632 A | 11/2000 | Landuyt | |
| 6,159,209 A | 12/2000 | Hakky | |
| 6,190,357 B1 | 2/2001 | Ferrari et al. | |
| 6,216,043 B1 | 4/2001 | Swanson et al. | |
| 6,216,044 B1 | 4/2001 | Kordis | |
| 6,221,007 B1 | 4/2001 | Green | |
| 6,251,121 B1 | 6/2001 | Saadat | |
| 6,293,952 B1 | 9/2001 | Brosens et al. | |
| 6,319,272 B1 | 11/2001 | Brenneman et al. | |
| 6,328,686 B1 | 12/2001 | Kovac | |
| 6,378,524 B1 | 4/2002 | Jones | |
| 6,387,110 B1 | 5/2002 | Drucker et al. | |
| 6,395,012 B1 | 5/2002 | Yoon et al. | |
| 6,402,701 B1 | 6/2002 | Kaplan et al. | |
| 6,428,498 B2 | 8/2002 | Uflacker | |
| 6,428,539 B1 | 8/2002 | Baxter et al. | |
| 6,432,116 B1 | 8/2002 | Callister et al. | |
| 6,440,061 B1 | 8/2002 | Wenner et al. | |
| 6,458,076 B1 | 10/2002 | Pruitt | |
| 6,471,644 B1 | 10/2002 | Sidor, Jr. | |
| 6,494,909 B2 | 12/2002 | Greenhalgh | |
| 6,517,561 B1 | 2/2003 | Phillips | |
| 6,537,207 B1 | 3/2003 | Rice et al. | |
| 6,547,784 B1 | 4/2003 | Thompson et al. | |
| 6,565,557 B1 | 5/2003 | Sporri et al. | |
| 6,605,037 B1 | 8/2003 | Moll et al. | |
| 6,607,545 B2 | 8/2003 | Kammerer et al. | |
| 6,612,977 B2 | 9/2003 | Staskin et al. | |
| 6,626,924 B1 | 9/2003 | Klopotek | |
| 6,626,940 B2 | 9/2003 | Crowley | |
| 6,638,235 B2 | 10/2003 | Miller et al. | |
| 6,673,023 B2 | 1/2004 | Pflueger | |
| 6,673,101 B1 | 1/2004 | Fitzgerald et al. | |
| 6,682,477 B2 | 1/2004 | Boebel et al. | |

(56) References Cited

U.S. PATENT DOCUMENTS

| | | |
|---|---|---|
| 6,705,986 B2 | 3/2004 | Fiegel et al. |
| 6,709,667 B1 | 3/2004 | Lowe et al. |
| 6,742,236 B1 | 6/2004 | Dion et al. |
| 6,758,824 B1* | 7/2004 | Miller et al. .................. 600/568 |
| 6,758,882 B2 | 7/2004 | Nakamura et al. |
| 6,763,833 B1 | 7/2004 | Khera et al. |
| 6,802,825 B2 | 10/2004 | Ackerman et al. |
| 6,805,131 B2 | 10/2004 | Kordis |
| 6,812,204 B1 | 11/2004 | McHale et al. |
| 6,821,274 B2 | 11/2004 | McHale et al. |
| 6,821,282 B2 | 11/2004 | Perry et al. |
| 6,827,703 B1 | 12/2004 | Ackerman |
| 6,858,024 B1 | 2/2005 | Berg et al. |
| 6,896,682 B1 | 5/2005 | Mcclellan et al. |
| 6,951,569 B2 | 10/2005 | Nohilly et al. |
| 6,960,203 B2 | 11/2005 | Xiao et al. |
| 6,979,332 B2 | 12/2005 | Adams |
| 6,997,925 B2 | 2/2006 | Maguire et al. |
| 7,037,321 B2 | 5/2006 | Sachdeva et al. |
| 7,070,559 B2 | 7/2006 | Adams et al. |
| 7,105,003 B2 | 9/2006 | Hiltebrandt |
| 7,150,713 B2 | 12/2006 | Shener et al. |
| 7,189,206 B2 | 3/2007 | Quick et al. |
| 7,226,459 B2 | 6/2007 | Cesarini et al. |
| 7,226,460 B2 | 6/2007 | Gibson et al. |
| 7,249,602 B1 | 7/2007 | Emanuel |
| 7,458,940 B2 | 12/2008 | Miller |
| 7,462,187 B2 | 12/2008 | Johnson et al. |
| 7,468,060 B2 | 12/2008 | Utley et al. |
| 7,481,817 B2 | 1/2009 | Sauer |
| 7,491,212 B2 | 2/2009 | Sikora et al. |
| 7,497,833 B2 | 3/2009 | Miller |
| 7,510,563 B2 | 3/2009 | Cesarini et al. |
| 7,588,545 B2 | 9/2009 | Cohen et al. |
| 7,611,474 B2 | 11/2009 | Hibner et al. |
| 7,666,200 B2 | 2/2010 | Heisler |
| 7,749,254 B2 | 7/2010 | Sobelman et al. |
| 7,753,857 B2 | 7/2010 | Hibner |
| 7,763,033 B2 | 7/2010 | Gruber et al. |
| 7,785,250 B2 | 8/2010 | Nakao |
| 7,806,835 B2 | 10/2010 | Hibner et al. |
| 7,922,737 B1 | 4/2011 | Cesarini et al. |
| 7,938,804 B2 | 5/2011 | Fischvogt |
| 7,963,433 B2 | 6/2011 | Whitman et al. |
| 7,981,130 B2 | 7/2011 | Seeh |
| 2001/0008575 A1 | 7/2001 | Rho et al. |
| 2001/0029371 A1 | 10/2001 | Kordis |
| 2001/0039963 A1 | 11/2001 | Spear et al. |
| 2001/0041900 A1 | 11/2001 | Callister et al. |
| 2001/0047183 A1 | 11/2001 | Privitera et al. |
| 2001/0056222 A1 | 12/2001 | Rudischhauser et al. |
| 2002/0010457 A1 | 1/2002 | Duchon et al. |
| 2002/0013601 A1 | 1/2002 | Nobles et al. |
| 2002/0020417 A1 | 2/2002 | Nikolchev |
| 2002/0068934 A1 | 6/2002 | Edwards et al. |
| 2002/0082519 A1 | 6/2002 | Miller et al. |
| 2002/0082634 A1 | 6/2002 | Kammerer et al. |
| 2002/0188307 A1* | 12/2002 | Pintor et al. .................. 606/159 |
| 2002/0193705 A1* | 12/2002 | Burbank et al. .............. 600/562 |
| 2003/0050639 A1 | 3/2003 | Yachia et al. |
| 2003/0083684 A1 | 5/2003 | Cesarini et al. |
| 2003/0114875 A1 | 6/2003 | Sjostrom |
| 2003/0153940 A1 | 8/2003 | Nohilly et al. |
| 2004/0002702 A1 | 1/2004 | Xiao et al. |
| 2004/0002703 A1 | 1/2004 | Xiao et al. |
| 2004/0049211 A1 | 3/2004 | Tremulis et al. |
| 2004/0049217 A1* | 3/2004 | Ross et al. .................... 606/171 |
| 2004/0092980 A1* | 5/2004 | Cesarini et al. .............. 606/159 |
| 2004/0116955 A1 | 6/2004 | Foltz et al. |
| 2004/0127932 A1 | 7/2004 | Shah |
| 2004/0204682 A1 | 10/2004 | Smith |
| 2004/0225187 A1 | 11/2004 | Kamrava et al. |
| 2004/0255957 A1 | 12/2004 | Cafferata |
| 2004/0267157 A1 | 12/2004 | Miller et al. |
| 2005/0027245 A1 | 2/2005 | Sachdeva et al. |
| 2005/0045183 A1 | 3/2005 | Callister et al. |
| 2005/0080318 A1 | 4/2005 | Squicciarini |
| 2005/0090849 A1 | 4/2005 | Adams |
| 2005/0107663 A1 | 5/2005 | Saadat et al. |
| 2005/0113715 A1 | 5/2005 | Schwindt et al. |
| 2005/0113836 A1 | 5/2005 | Lozier et al. |
| 2005/0113857 A1 | 5/2005 | Nohilly et al. |
| 2005/0177168 A1 | 8/2005 | Brunnett et al. |
| 2005/0182397 A1 | 8/2005 | Ryan |
| 2005/0187572 A1* | 8/2005 | Johnston et al. .............. 606/167 |
| 2005/0222598 A1 | 10/2005 | Ho et al. |
| 2005/0234437 A1 | 10/2005 | Baxter et al. |
| 2005/0240206 A1 | 10/2005 | Sjostrom |
| 2005/0245960 A1 | 11/2005 | Grundeman |
| 2005/0250933 A1 | 11/2005 | Binz et al. |
| 2005/0250993 A1 | 11/2005 | Jaeger |
| 2005/0267408 A1 | 12/2005 | Grandt et al. |
| 2005/0277970 A1 | 12/2005 | Norman et al. |
| 2005/0277975 A1 | 12/2005 | Saadat et al. |
| 2005/0288551 A1 | 12/2005 | Callister et al. |
| 2006/0004436 A1 | 1/2006 | Amarant et al. |
| 2006/0009798 A1 | 1/2006 | Callister et al. |
| 2006/0036138 A1 | 2/2006 | Heller et al. |
| 2006/0047185 A1 | 3/2006 | Sherner et al. |
| 2006/0064074 A1 | 3/2006 | Mallaby |
| 2006/0089658 A1 | 4/2006 | Harrington |
| 2006/0178670 A1* | 8/2006 | Woloszko et al. ............. 606/48 |
| 2006/0189972 A1 | 8/2006 | Grossman |
| 2006/0200042 A1* | 9/2006 | Weikel et al. ................ 600/566 |
| 2006/0206136 A1 | 9/2006 | Sachdeva et al. |
| 2006/0212055 A1 | 9/2006 | Karabey et al. |
| 2006/0229647 A1 | 10/2006 | Spitz et al. |
| 2006/0241344 A1 | 10/2006 | Wilk |
| 2006/0241586 A1 | 10/2006 | Wilk |
| 2006/0241630 A1 | 10/2006 | Brunnett et al. |
| 2006/0293560 A1 | 12/2006 | Nguyen et al. |
| 2007/0010845 A1 | 1/2007 | Gong et al. |
| 2007/0161957 A1 | 7/2007 | Guenther et al. |
| 2007/0225744 A1 | 9/2007 | Nobles et al. |
| 2007/0227544 A1 | 10/2007 | Swann et al. |
| 2007/0232859 A1 | 10/2007 | Secrest et al. |
| 2008/0015621 A1 | 1/2008 | Emanuel |
| 2008/0051758 A1 | 2/2008 | Rioux et al. |
| 2008/0058588 A1 | 3/2008 | Emanuel |
| 2008/0058595 A1 | 3/2008 | Snoke et al. |
| 2008/0065125 A1* | 3/2008 | Olson .......................... 606/159 |
| 2008/0097467 A1 | 4/2008 | Gruber et al. |
| 2008/0097468 A1 | 4/2008 | Adams et al. |
| 2008/0097469 A1 | 4/2008 | Gruber et al. |
| 2008/0097470 A1 | 4/2008 | Gruber et al. |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0147012 A1 | 6/2008 | Rome |
| 2008/0183192 A1 | 7/2008 | Saal et al. |
| 2008/0234715 A1 | 9/2008 | Pesce et al. |
| 2008/0245371 A1 | 10/2008 | Gruber et al. |
| 2008/0249366 A1 | 10/2008 | Gruber et al. |
| 2008/0249534 A1 | 10/2008 | Gruber et al. |
| 2008/0262302 A1 | 10/2008 | Azarbarzin et al. |
| 2008/0281224 A1 | 11/2008 | Johnson |
| 2008/0319342 A1 | 12/2008 | Shabaz et al. |
| 2009/0005739 A1 | 1/2009 | Hart et al. |
| 2009/0048485 A1 | 2/2009 | Heisler |
| 2009/0054728 A1 | 2/2009 | Trusty |
| 2009/0118699 A1 | 5/2009 | Utley et al. |
| 2009/0137927 A1 | 5/2009 | Miller |
| 2009/0177217 A1 | 7/2009 | Keller |
| 2009/0198149 A1 | 8/2009 | Privitera et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0063360 A1 | 3/2010 | Harrington et al. |
| 2010/0076343 A1 | 3/2010 | Vetter et al. |
| 2010/0152533 A1 | 6/2010 | Mark |

(56) References Cited

U.S. PATENT DOCUMENTS

| | | | |
|---|---|---|---|
| 2010/0152758 A1 | 6/2010 | Mark et al. | |
| 2010/0152761 A1 | 6/2010 | Mark | |
| 2010/0160818 A1 | 6/2010 | Haberstich et al. | |
| 2010/0179480 A1 | 7/2010 | Sugiki et al. | |
| 2010/0185153 A1 | 7/2010 | Sugiki et al. | |
| 2010/0185222 A1 | 7/2010 | Keller | |
| 2010/0198242 A1 | 8/2010 | Heisler | |
| 2010/0217299 A1 | 8/2010 | Williams et al. | |
| 2010/0222700 A1 | 9/2010 | Hibner | |
| 2010/0256662 A1 | 10/2010 | Racenet et al. | |
| 2010/0274194 A1 | 10/2010 | Sobelman et al. | |
| 2010/0312053 A1 | 12/2010 | Larsen | |
| 2011/0034943 A1* | 2/2011 | Churchill et al. | 606/171 |
| 2011/0046624 A1 | 2/2011 | Lin | |
| 2011/0077674 A1 | 3/2011 | Sullivan et al. | |
| 2011/0125177 A1 | 5/2011 | Yates et al. | |
| 2011/0192883 A1 | 8/2011 | Whitman et al. | |

FOREIGN PATENT DOCUMENTS

| | | |
|---|---|---|
| EP | 0141589 | 5/1985 |
| EP | 0366292 | 5/1990 |
| EP | 0449663 | 10/1991 |
| EP | 0531710 | 10/1991 |
| EP | 0539125 | 4/1993 |
| EP | 782427 | 2/1996 |
| EP | 853468 | 5/1996 |
| EP | 0812573 | 12/1997 |
| EP | 1259180 | 9/2001 |
| EP | 1635695 | 1/2005 |
| FR | 2701401 | 8/1994 |
| WO | WO 94/07445 | 4/1994 |
| WO | WO 94/11052 | 5/1994 |
| WO | WO 95/10326 | 4/1995 |
| WO | WO 95/32011 | 11/1995 |
| WO | WO 96/15741 | 5/1996 |
| WO | WO 98/18520 | 5/1998 |
| WO | WO 98/29068 | 7/1998 |
| WO | WO 98/51244 | 11/1998 |
| WO | WO 99/60960 | 12/1999 |
| WO | WO 00/00100 | 1/2000 |
| WO | WO 00/12832 | 3/2000 |
| WO | WO 00/66031 | 11/2000 |
| WO | WO01/08575 | 2/2001 |
| WO | WO03/037194 | 5/2003 |
| WO | WO 2005/009504 | 2/2005 |
| WO | WO 2005/048862 | 6/2005 |
| WO | WO 2005/074844 | 8/2005 |
| WO | WO 2005/104966 | 11/2005 |
| WO | WO 2009/111717 | 9/2009 |
| WO | WO 2010/127171 | 11/2010 |
| WO | WO 2010/127174 | 11/2010 |

OTHER PUBLICATIONS

International Search Report and Written Opinion Received in PCT/US07/83982 Dated May 20, 2008.
International Search Report and Written Opinion Received in PCT/US08/59493 Dated Apr. 4, 2008.
International Search Report and Written Opinion Received in PCT/US07/83833 Dated Jun. 5, 2008.
International Search Report and Written Opinion Received in PCT/US08/59504 Dated Sep. 4, 2008.
International Search Report and Written Opinion Received in PCT/US08/59503 Dated Sep. 5, 2008.
U.S. Appl. No. 12/432,691, including its prosecution history, and the Office Actions.
U.S. Appl. No. 12/432,702, including its prosecution history, and the Office Actions.
U.S. Appl. No. 12/432,686, including its prosecution history, and the Office Actions.
U.S. Appl. No. 12/432,675, including its prosecution history, and the Office Actions.
U.S. Appl. No. 12/432,647, including its prosecution history, and the Office Actions.
U.S. Appl. No. 12/917,351, including its prosecution history, and the Office Actions, Feb. 10, 2011.
U.S. Appl. No. 12/956,974, including its prosecution history, and the Office Actions, May 19, 2011.
U.S. Appl. No. 12/972,233, including its prosecution history, and the Office Actions, Mar. 31, 2011.
U.S. Appl. No. 12/565,620, including its prosecution history, and the Office Actions, Apr. 8, 2010.
U.S. Appl. No. 12/842,775, including its prosecution history, and the Office Actions, Mar. 3, 2011.
International Search Report and Written Opinion Received in PCT/US10/56416 Dated Jan. 11, 2011.
International Search Report and Written Opinion Received in PCT/US2010/033047 Dated Jul. 6, 2010.
International Search Report and Written Opinion Received in PCT/US2010/033050 Dated Jun. 29, 2010.
"When mechanical dilation is necessary, a few prerequisites can make a difference", OBG Management, Apr. 2009, vol. 21, No. 4, p. 29-33.
Mark H. Emanuel, "The Intra Uterine Morcellator: A New Hysteroscopic Operating Technique to Remove Intrauterine Polyps and Myomas," Journal of Minimally Invasive Gynecology, vol. 12, p. 62-66 (2005).
Reference AQ "Fishing Reel produced and sold by Shimano of Japan into the U.S. prior to Oct. 26, 2001," filed Oct. 17, 2005 in the prosecution file history of U.S. Appl. No. 09/983,810, 7 pages.
Trueclear Ultra, Reciprocating Morcellator 4.0, promotional piece, Smith & Nephew, Inc., 150 Minuteman Road, Andover, MA 01810 USA, dated Jul. 2012, 2 pages.

* cited by examiner

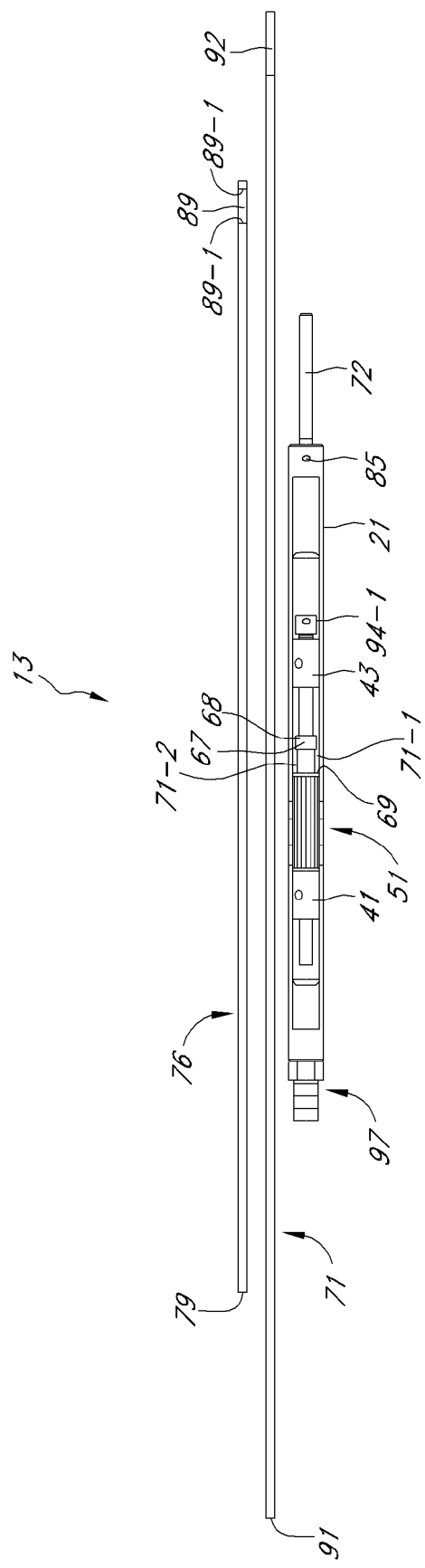

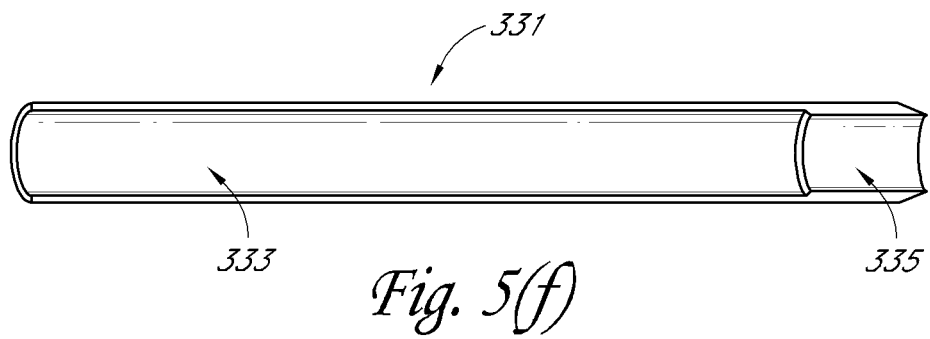
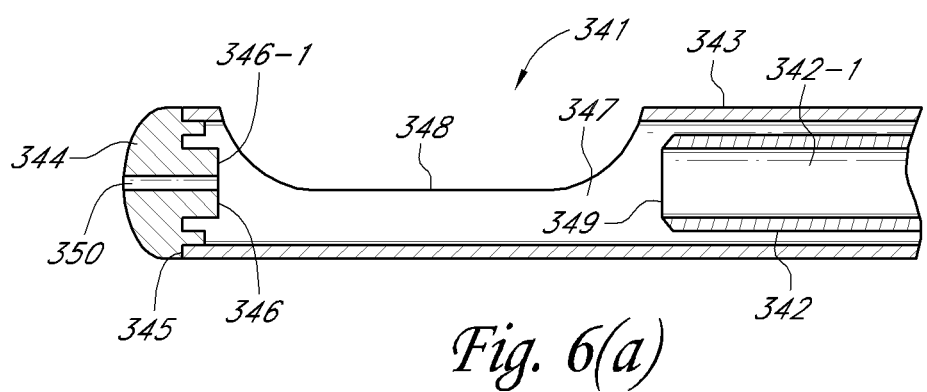
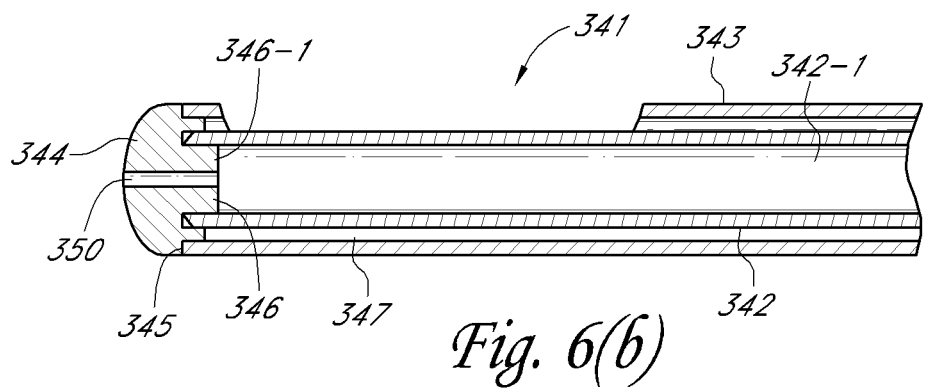

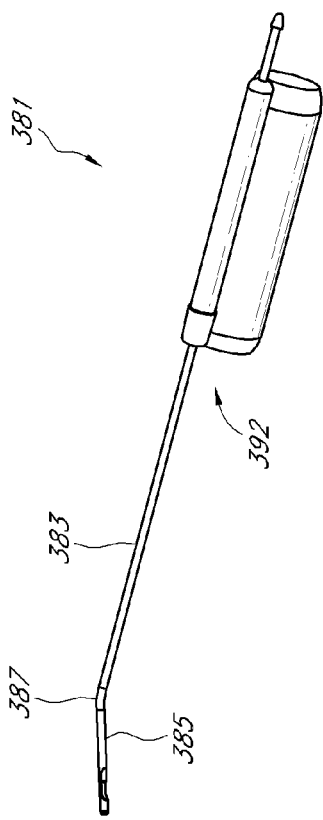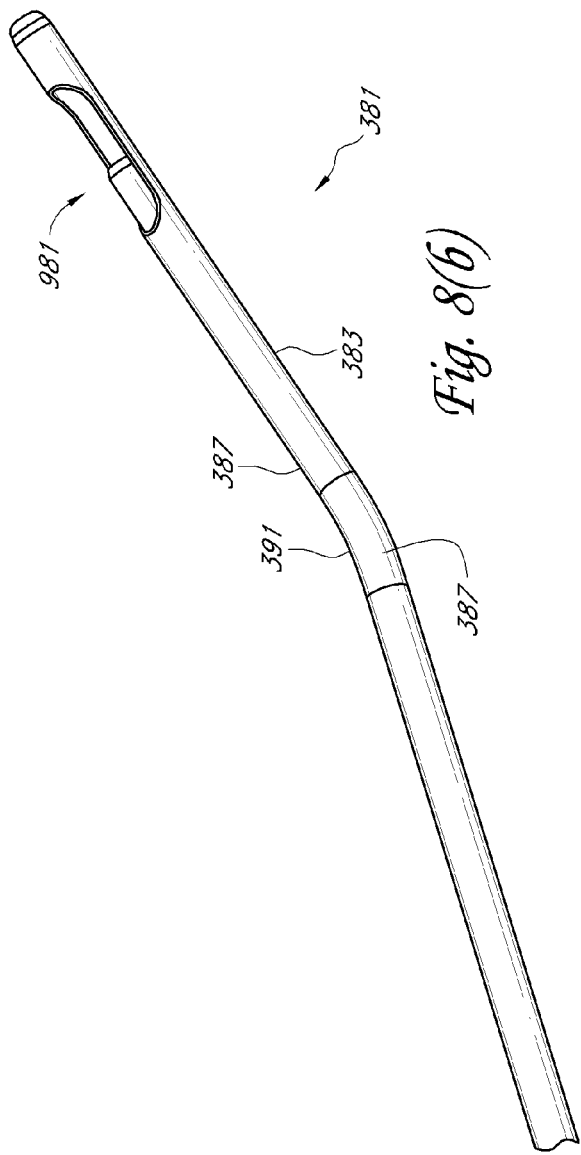

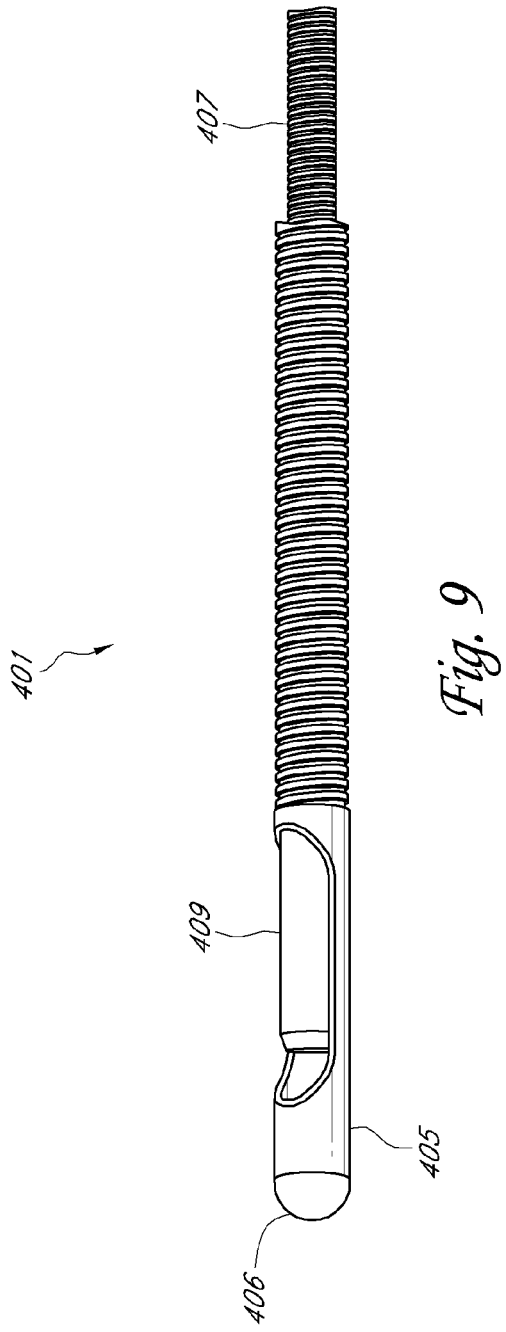
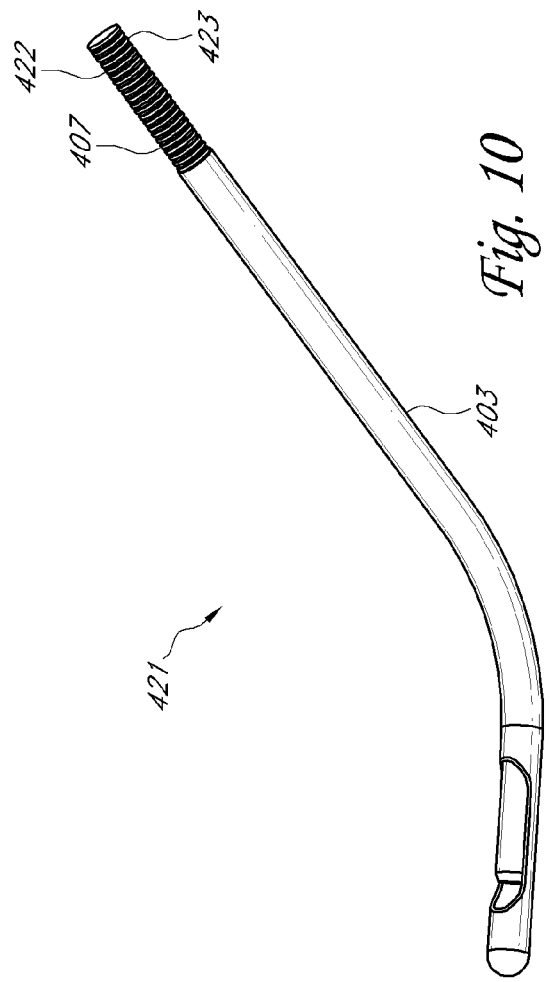

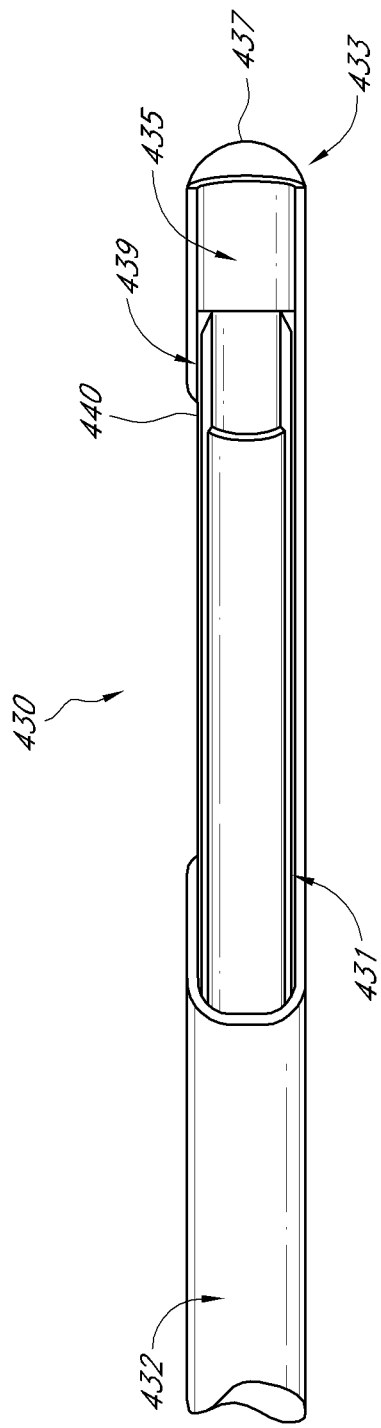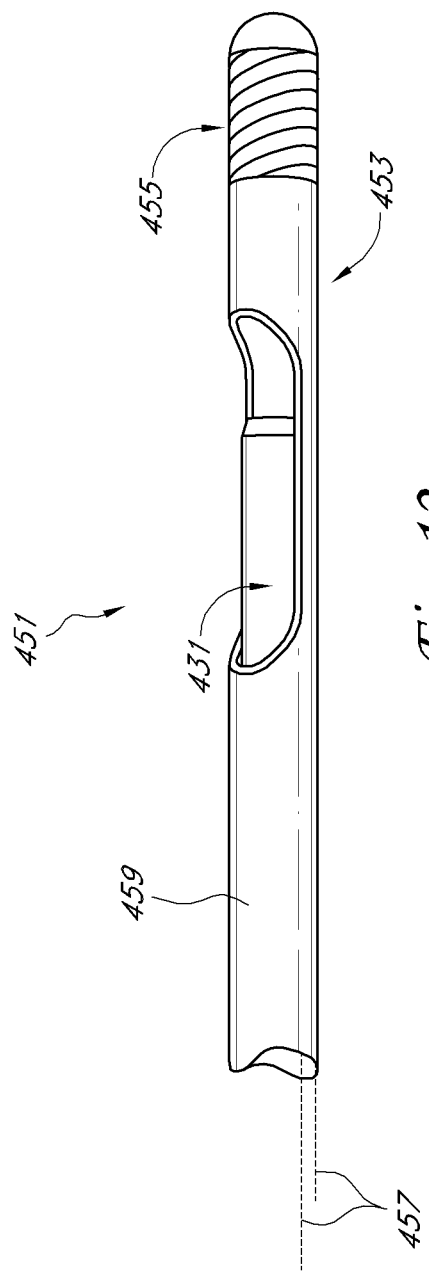
Fig. 11
Fig. 12

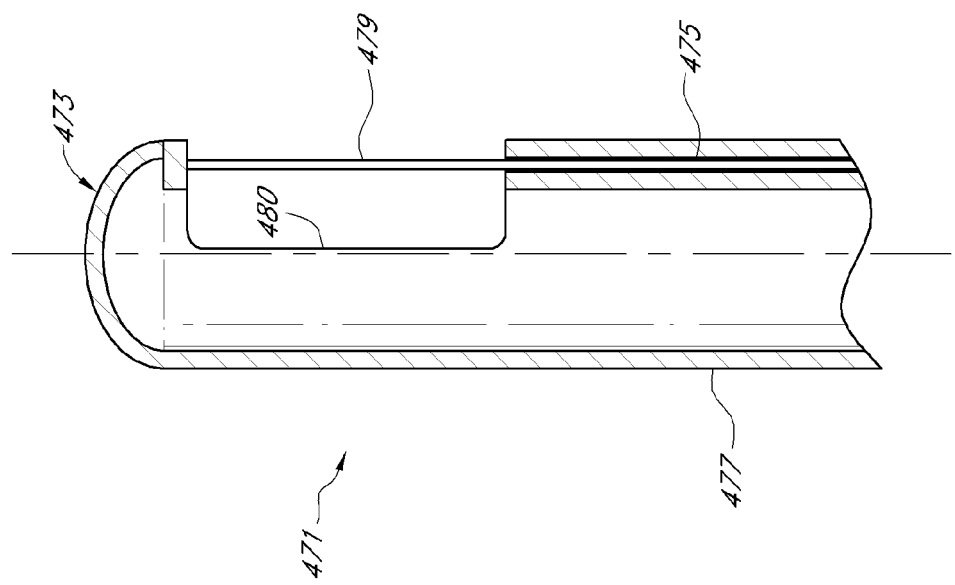
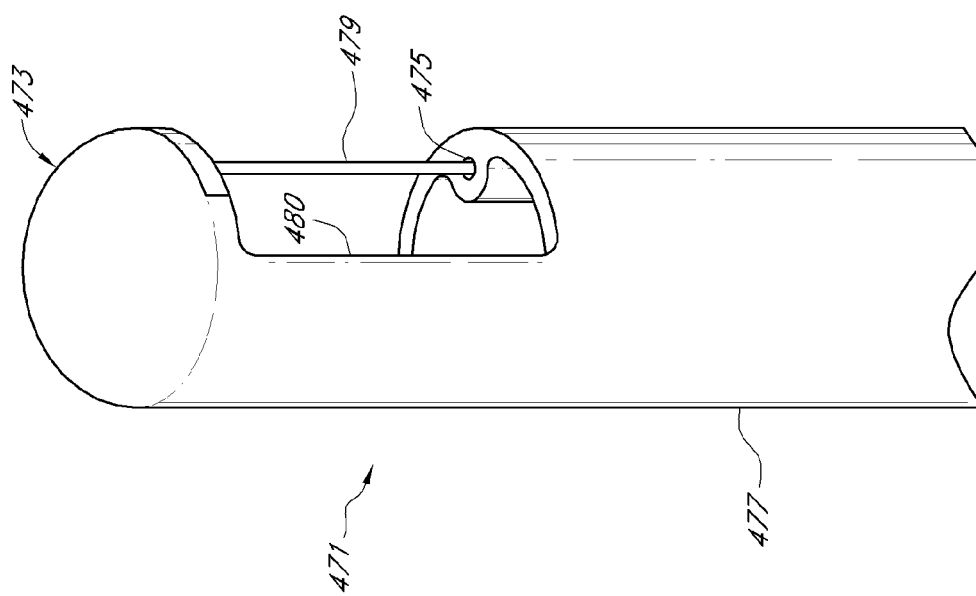

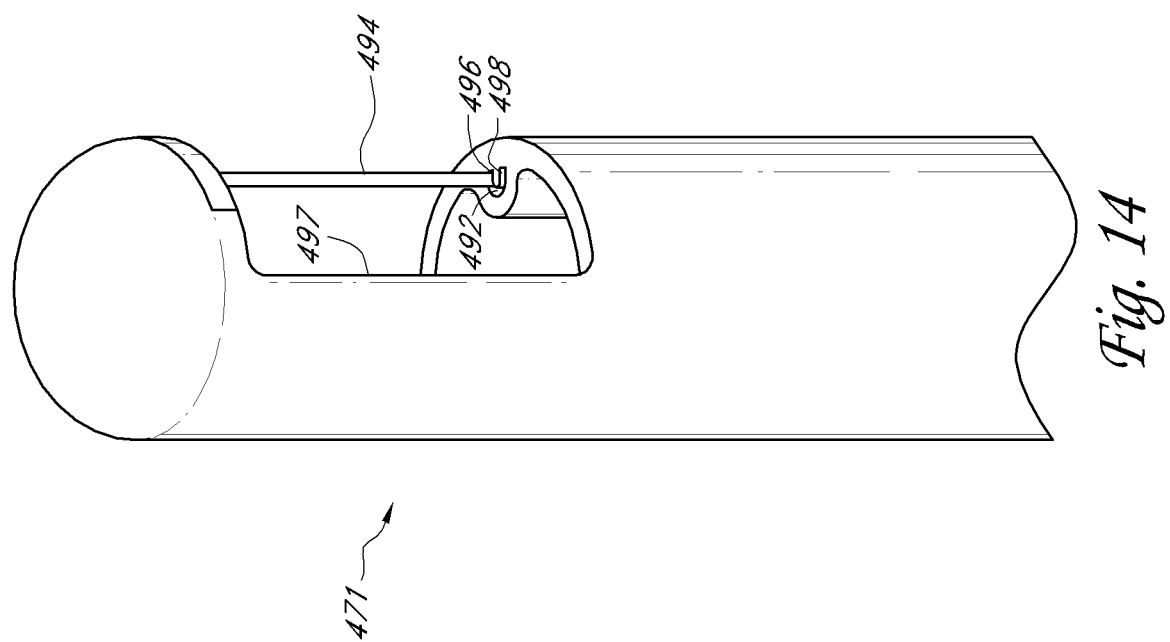

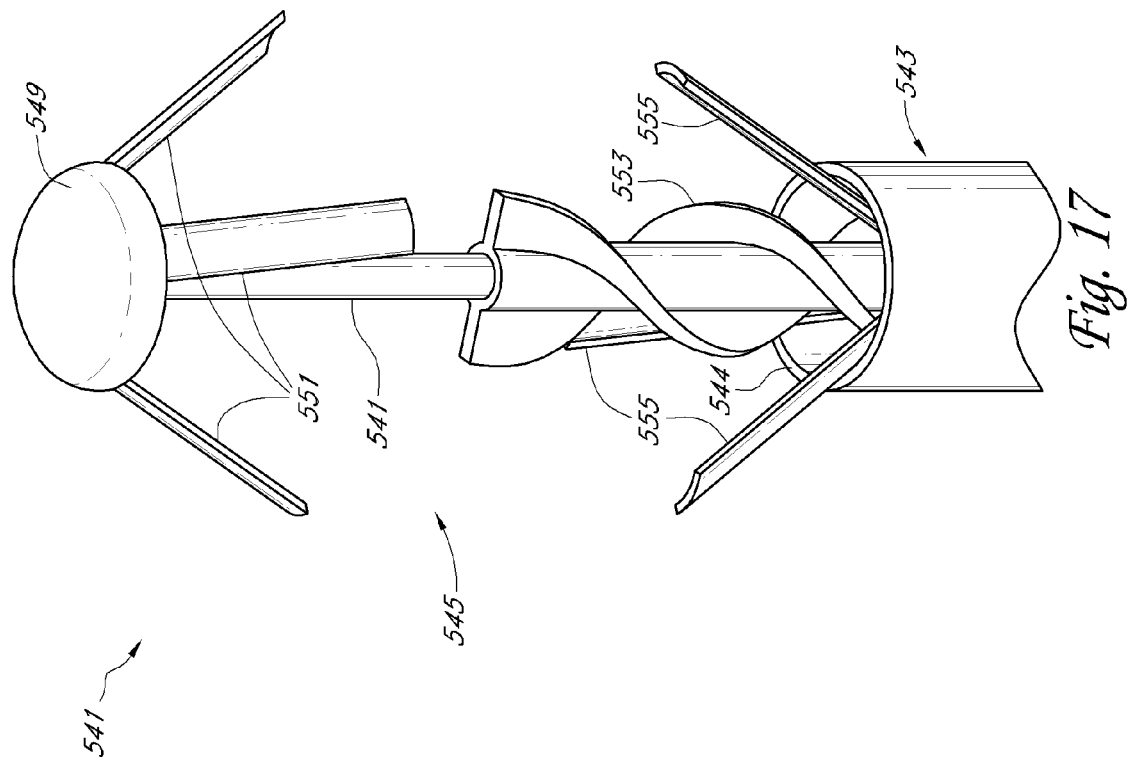

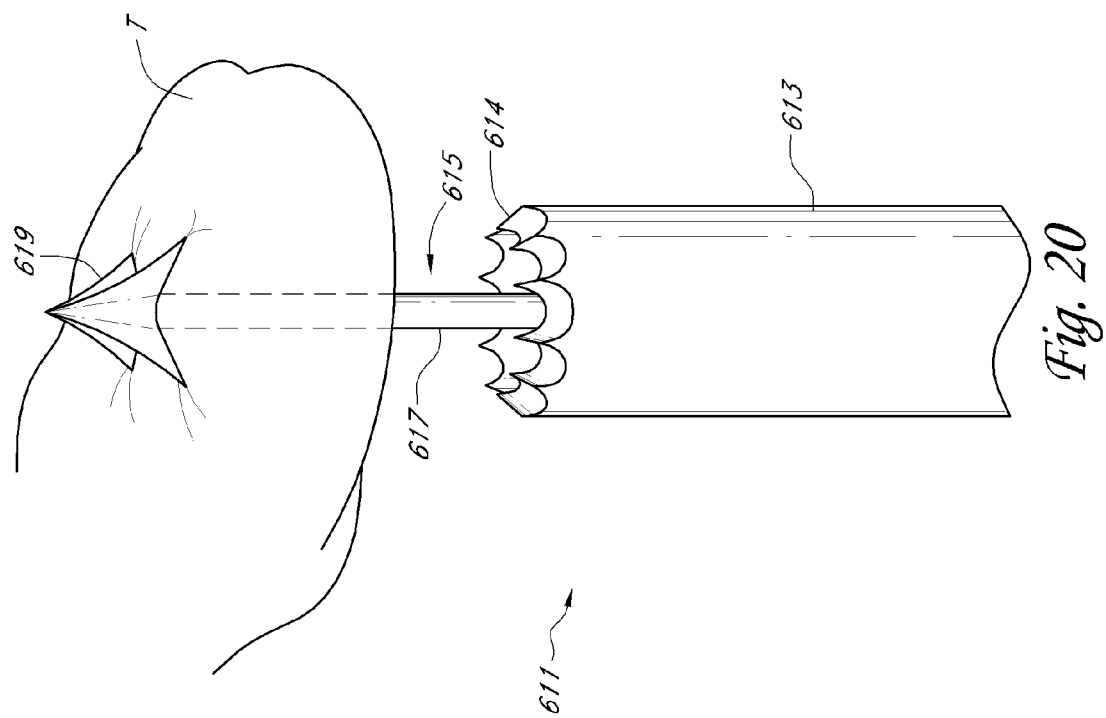

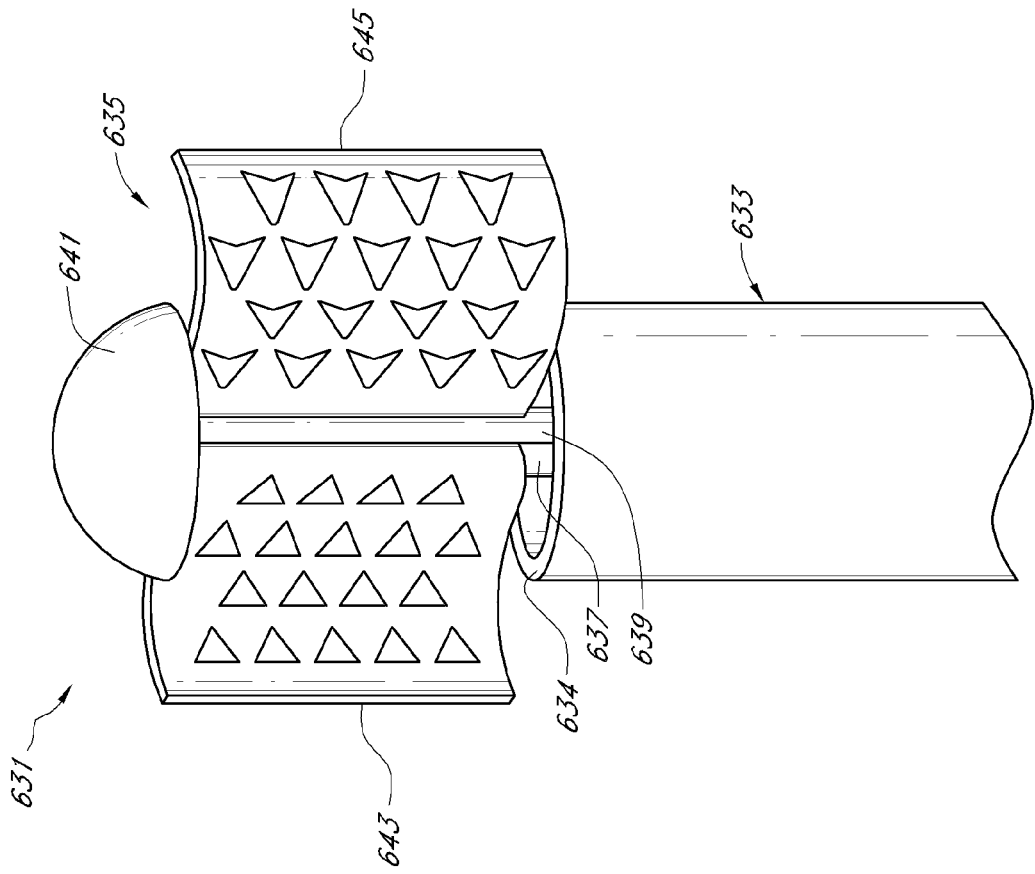
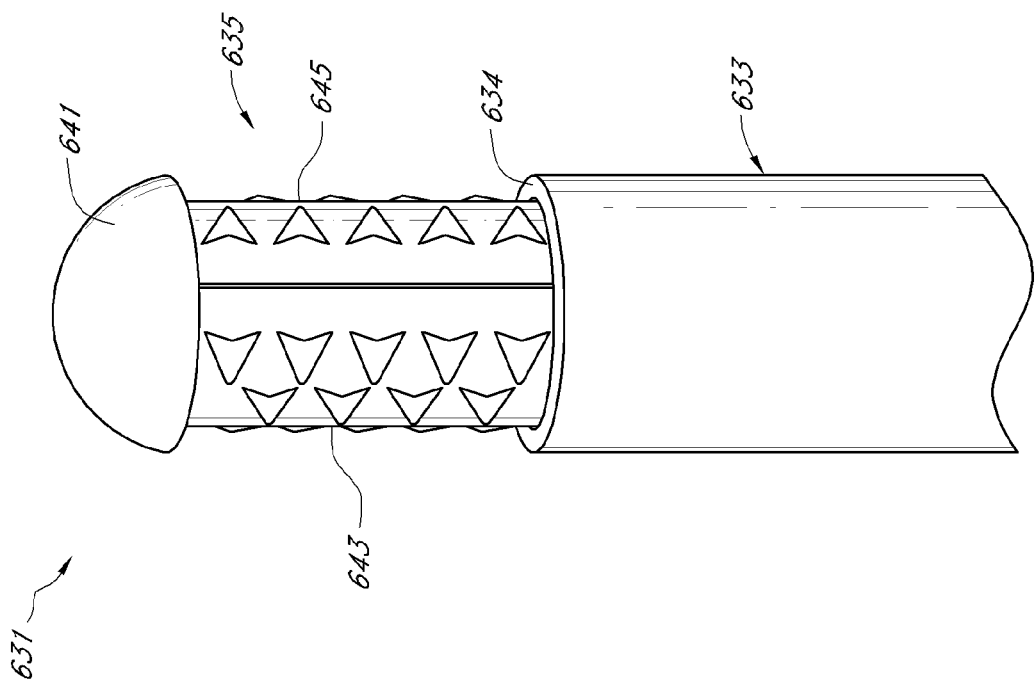

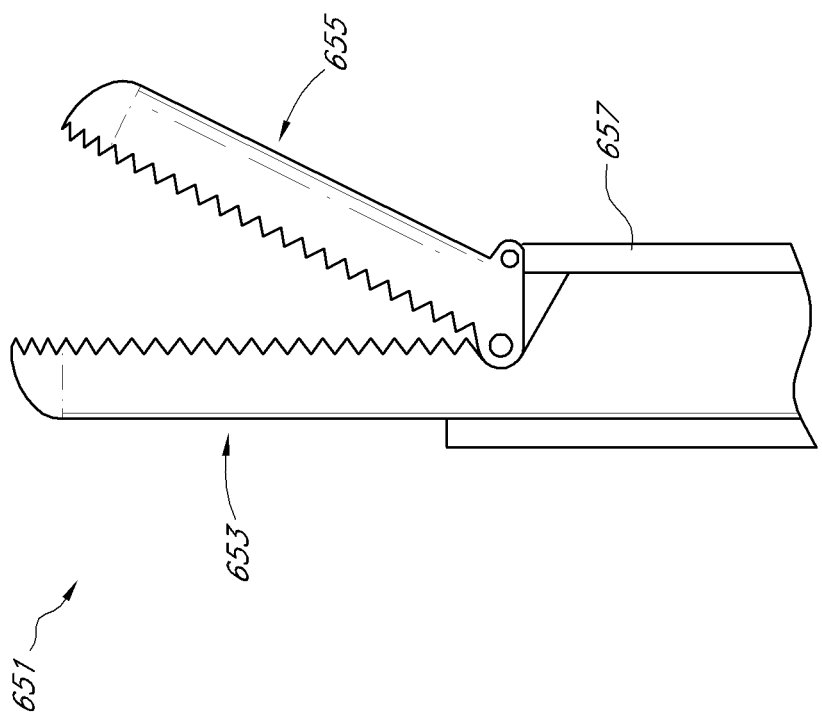
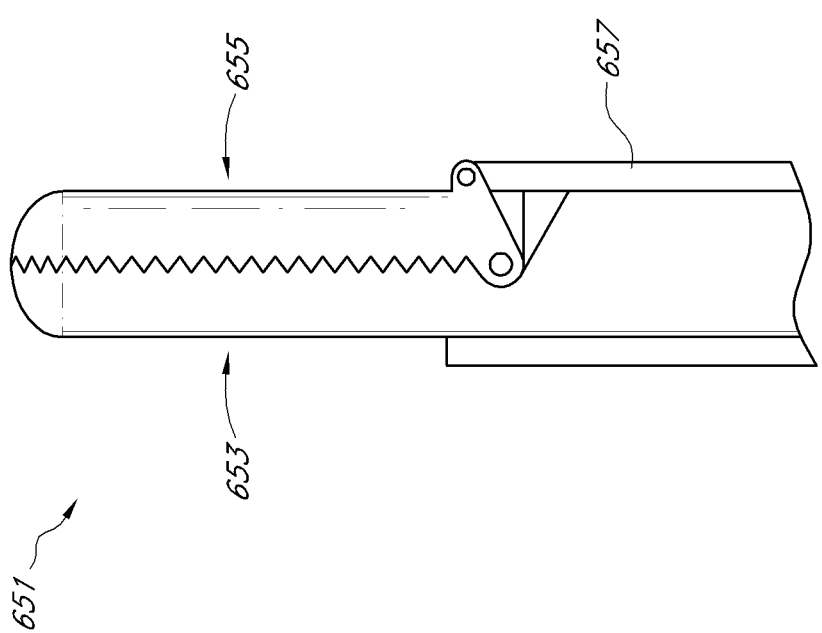
Fig. 22(b)
Fig. 22(a)

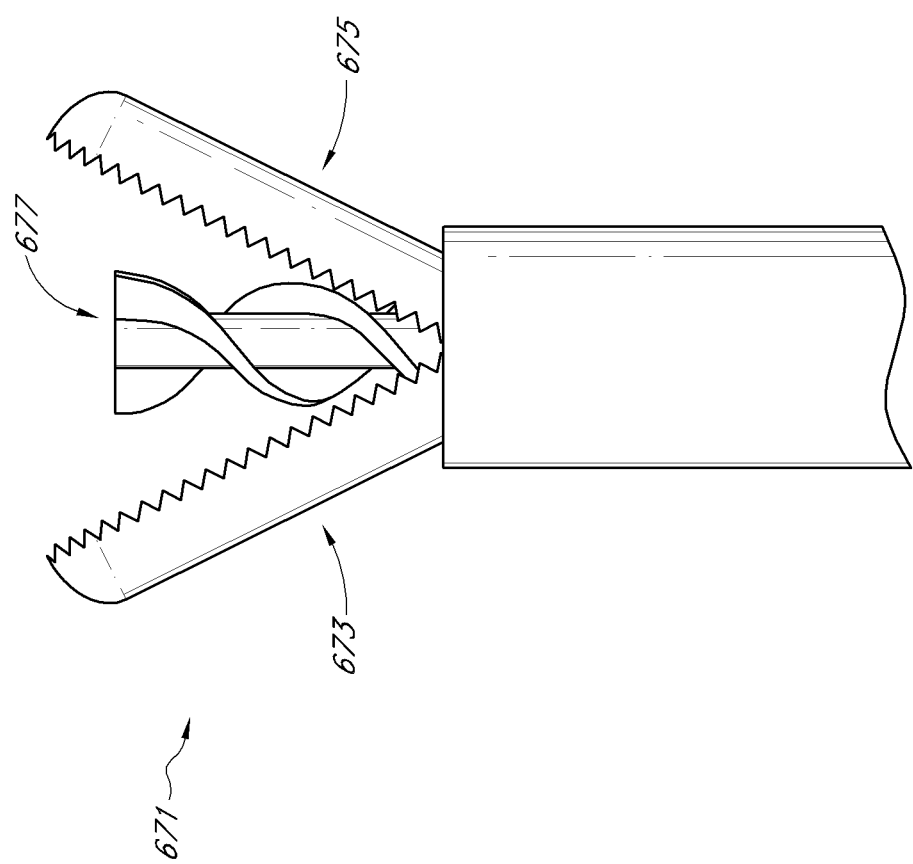

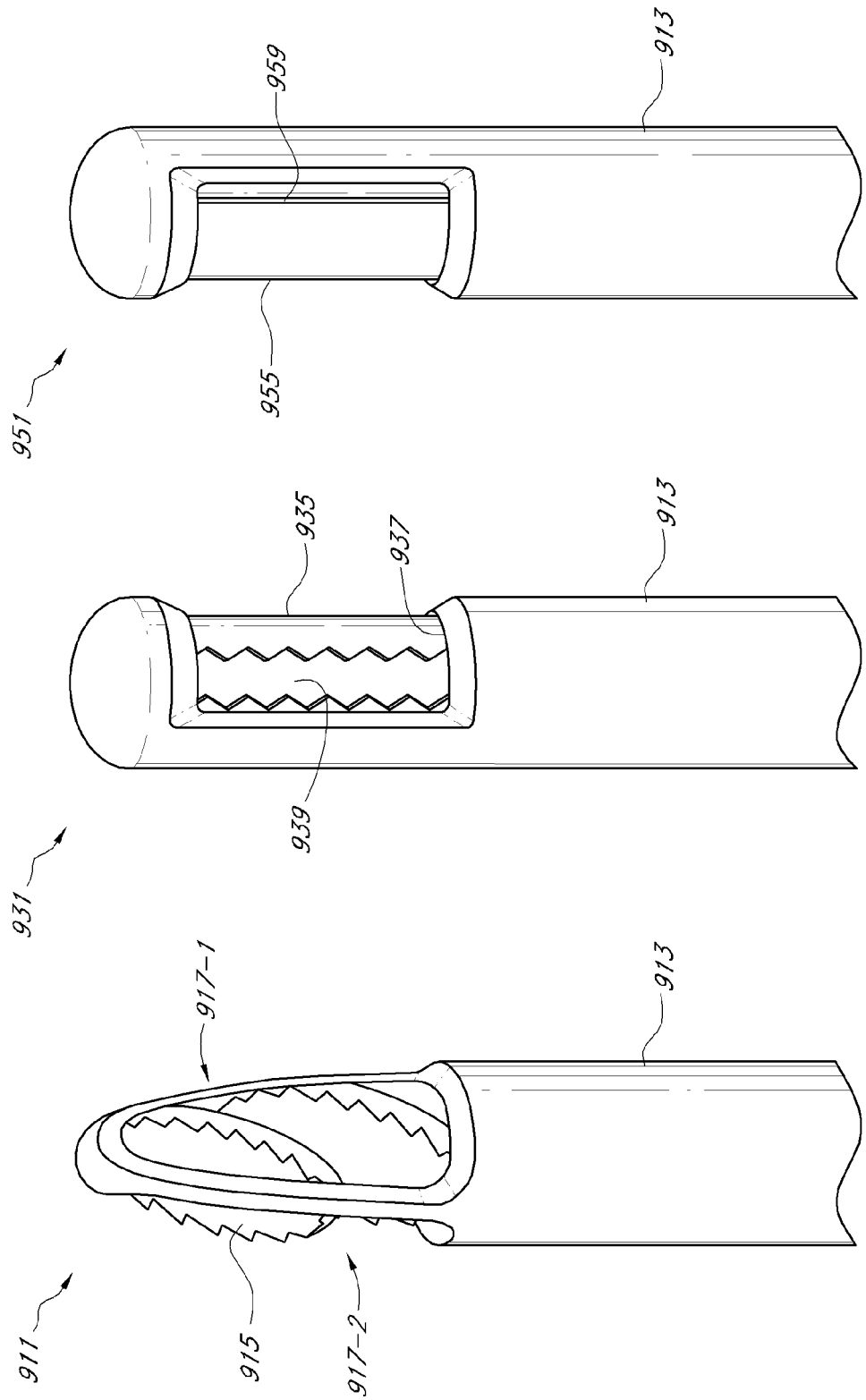

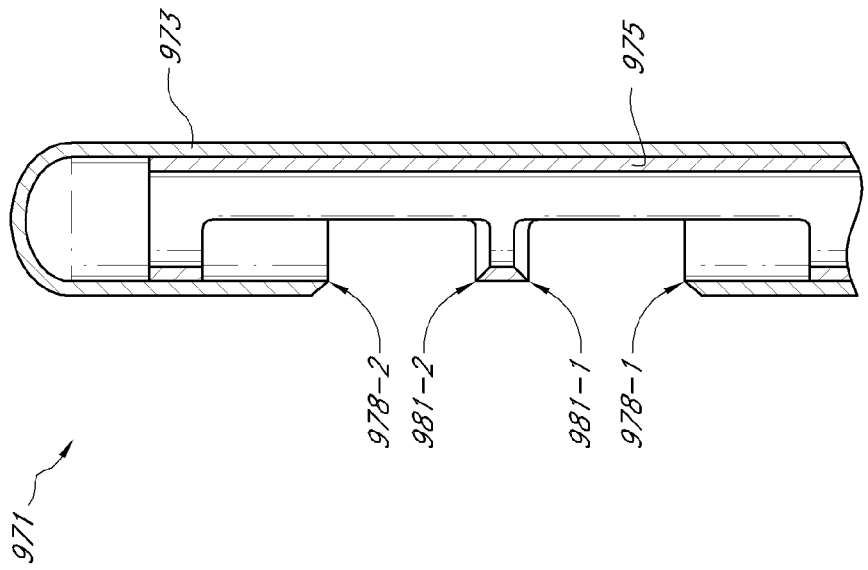
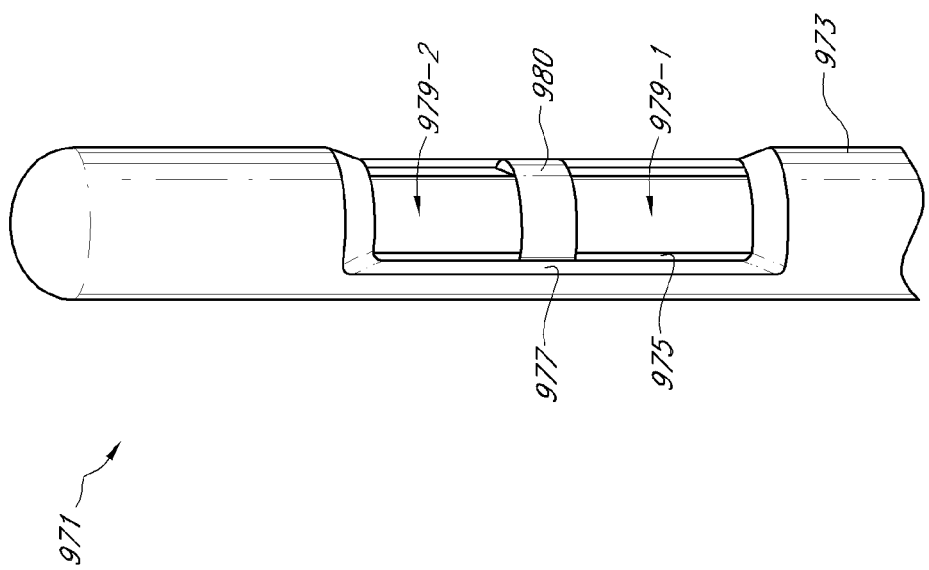

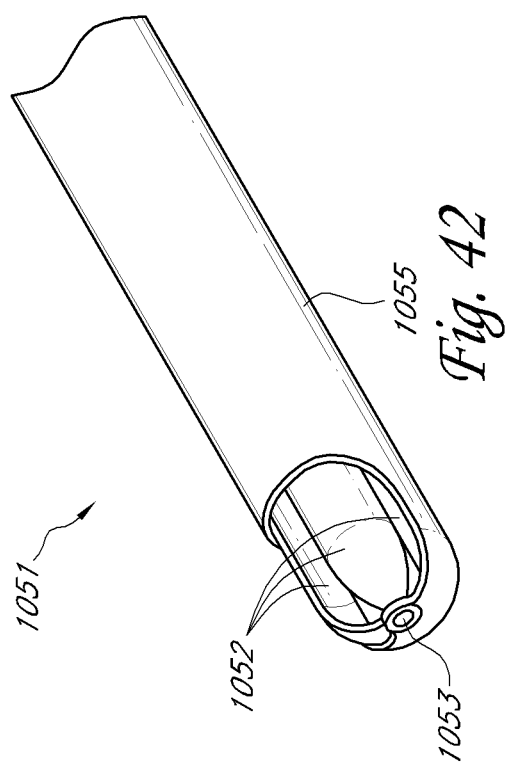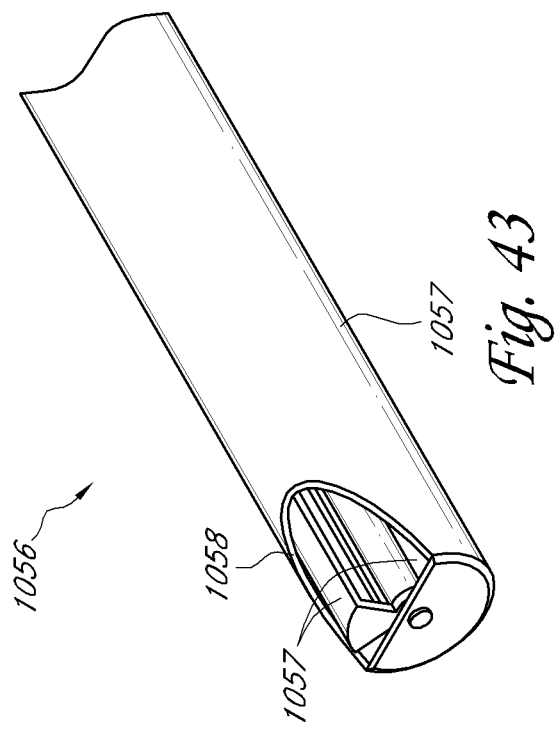

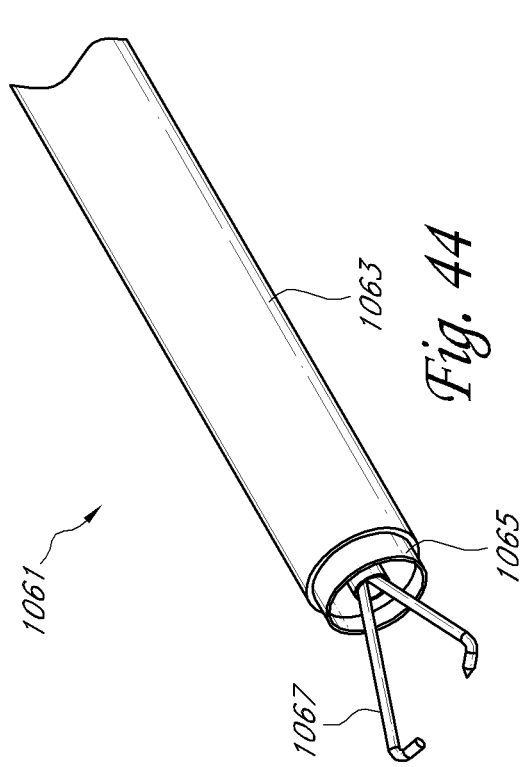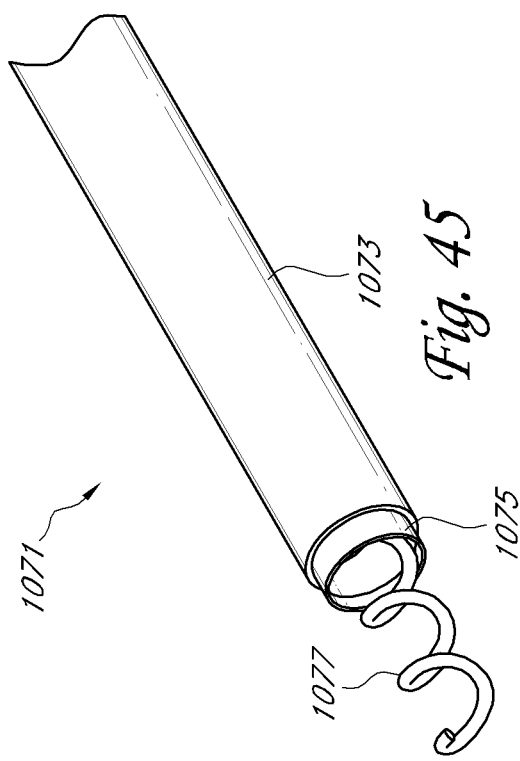

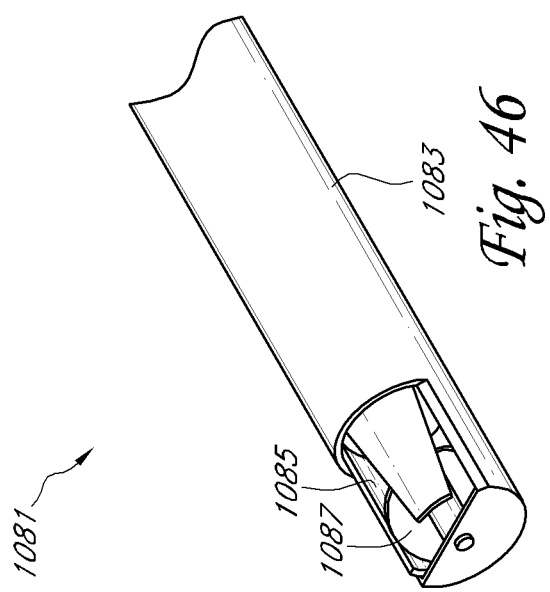

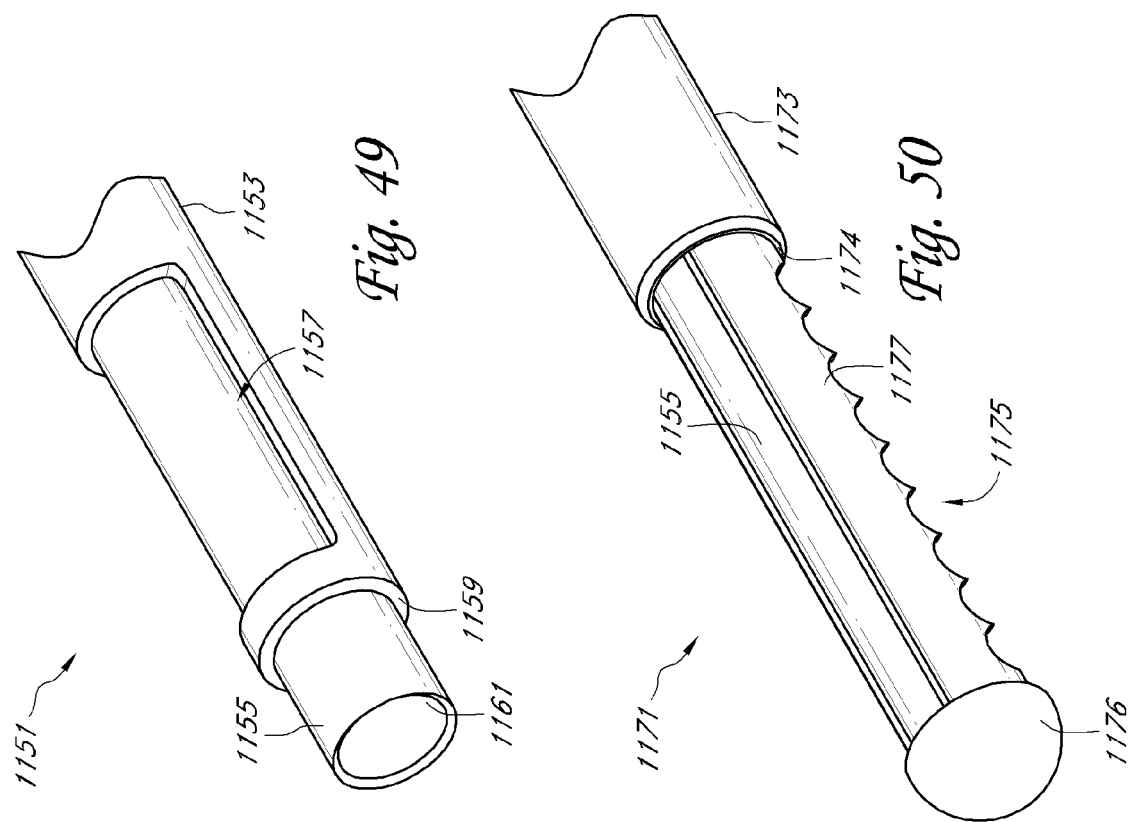

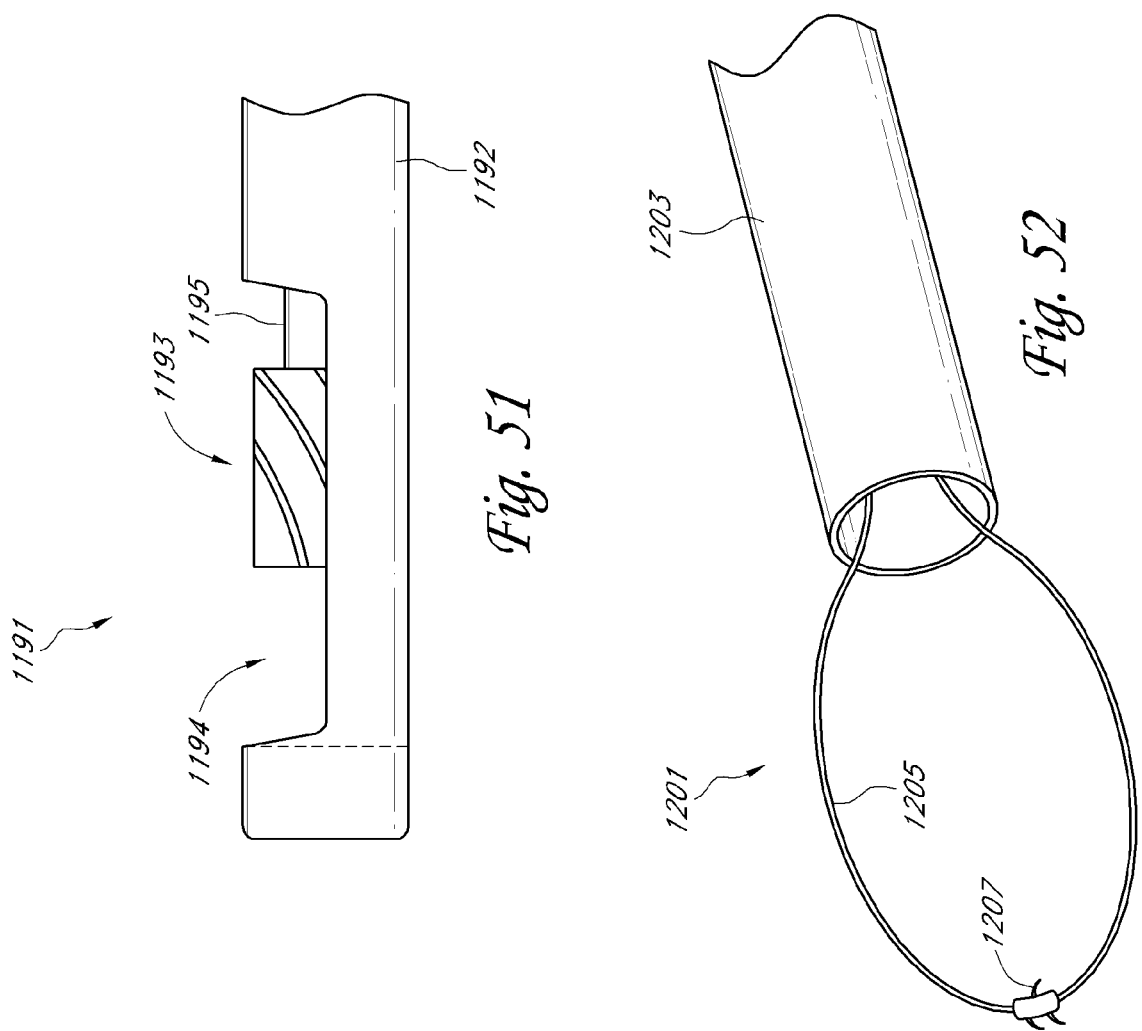

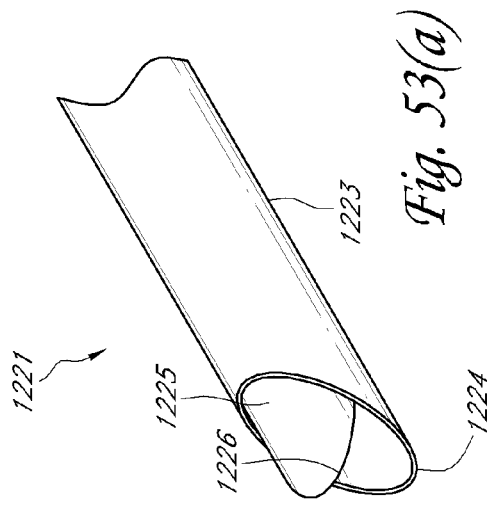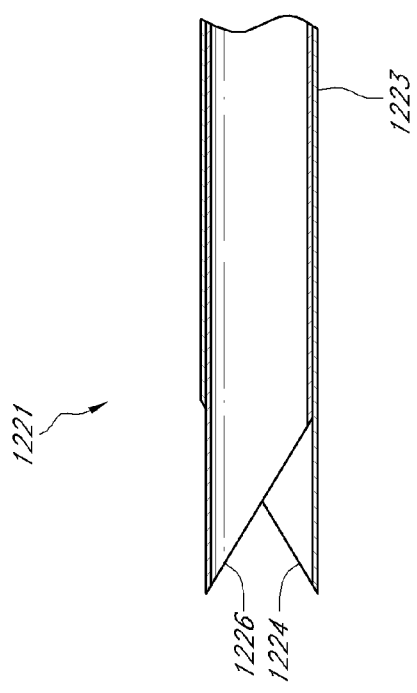
Fig. 53(a)
Fig. 53(b)

Test-Rotation Speeds—1000, 3000, 6000, 7500 rpm

| Duration (min) | Cutter # | Rotation Speed (RPM) | Translation Speed (cycles/sec) | Vacuum Pressure (mmHg) | Tissue Trap Weight (grams) | Cumulative Tissue Weight (grams) | Test Tissue Weight (grams) | Resection Rate (gm/min) | Fluid Vol. (cc) | Flow Rate (ml/min) | Clogs |
|---|---|---|---|---|---|---|---|---|---|---|---|
| 5:00 | 6 | 1000 | 2.8 | 600 | 24.7 | 0.8 | 0.8 | 0.2 | 1150 | 230 | 0 |
| 5:00 | 6 | 1000 | 2.8 | 600 | 27.6 | 3.7 | 2.9 | 0.6 | 2000 | 400 | 0 |
| 5:00 | 7 | 3000 | 2.8 | 600 | 29.3 | 5.4 | 5.4 | 1.1 | 1200 | 240 | 0 |
| 5:00 | 7 | 3000 | 2.8 | 600 | 34.7 | 10.8 | 5.4 | 1.1 | 1400 | 280 | 0 |
| 5:00 | 8 | 7600 | 2.8 | 600 | 30.2 | 6.3 | 6.3 | 1.3 | 2150 | 430 | 0 |
| 5:00 | 8 | 7600 | 2.8 | 600 | 37.6 | 13.7 | 7.4 | 1.5 | 1300 | 260 | 0 |
| 5:00 | 3 | 6000 | 2.8 | 600 | 34.7 | 10.8 | 10.8 | 2.2 | 1200 | 240 | 0 |
| 5:00 | 3 | 6000 | 2.8 | 600 | 44.3 | 20.4 | 9.6 | 1.9 | 900 | 180 | 0 |

Fig. 55

Test-Translation Speeds—1.2, 4.4 cps

| Duration (min) | Cutter # | Rotation Speed (RPM) | Translation Speed (cycles/sec) | Vacuum Pressure (mmHg) | Tissue Trap Weight (grams) | Cumulative Tissue Weight (grams) | Test Tissue Weight (grams) | Resection Rate (gm/min) | Fluid Vol. (cc) | Flow Rate (ml/min) | Clogs |
|---|---|---|---|---|---|---|---|---|---|---|---|
| 5:00 | 1A | 6000 | 4.4 | 600 | 35.9 | 12.0 | 12.0 | 2.4 | 1050 | 210 | 0 |
| 1:00 | 1A | 6000 | 4.4 | 600 | N/A | N/A | N/A | N/A | N/A | N/A | 1 |
| 5:00 | 1A | 6000 | 4.4 | 600 | 40.6 | 16.7 | 4.7 | 0.9 | 1700 | 340 | 0 |
| 5:00 | 1A | 6000 | 1.2 | 600 | 25.0 | 1.1 | 1.1 | 0.2 | N/A | N/A | 1 |
| 5:00 | 1A | 6000 | 1.2 | 600 | 32.5 | 8.6 | 8.6 | 1.7 | 700 | 140 | 0 |
| 5:00 | 1A | 6000 | 1.2 | 600 | 40.4 | 16.5 | 7.9 | 1.6 | 1150 | 230 | 0 |

Fig. 56

Test-Vacuum Pressure-300, 450 mmHg

| Duration (min) | Cutter # | Rotation Speed (RPM) | Translation Speed (cycles/sec) | Vacuum Pressure (mmHg) | Tissue Trap Weight (grams) | Cumulative Tissue Weight (grams) | Test Tissue Weight (grams) | Resection Rate (gm/min) | Fluid Vol. (cc) | Flow Rate (ml/min) | Clogs |
|---|---|---|---|---|---|---|---|---|---|---|---|
| 5:00 | 10 | 6000 | 2.8 | 450 | 39.0 | 15.1 | 15.1 | 3.0 | 700 | 140 | 0 |
| 1:00 | 10 | 6000 | 2.8 | 450 | 44.5 | 20.6 | 5.5 | 1.1 | 800 | 160 | 0 |
| 5:00 | 2 | 6000 | 2.8 | 300 | 28.3 | 4.4 | 4.4 | 0.9 | 950 | 190 | 0 |
| 5:00 | 2 | 6000 | 2.8 | 300 | 32.5 | 8.6 | 4.2 | 0.8 | 950 | 190 | 0 |

Fig. 57

METHOD, SYSTEM AND DEVICE FOR TISSUE REMOVAL

CROSS-REFERENCE TO RELATED APPLICATIONS

The present application claims the benefit under 35 U.S.C. 119(e) of U.S. Provisional Patent Application Ser. No. 60/910,618, filed Apr. 6, 2007, U.S. Provisional Patent Application Ser. No. 60/910,625, filed Apr. 6, 2007, and U.S. Provisional Patent Application Ser. No. 60/986,912, filed Nov. 9, 2007 all of which are incorporated herein by reference.

BACKGROUND OF THE INVENTION

The present invention relates generally to methods, systems and devices for the removal of tissue and relates more particularly to methods, systems, and devices well-suited for the removal of uterine fibroids and other abnormal gynecological tissues.

It is believed that uterine fibroids occur in a substantial percentage of the female population, perhaps in at least 20 to 40 percent of all women. Uterine fibroids are well-defined, non-cancerous tumors that are commonly found in the smooth muscle layer of the uterus. In many instances, uterine fibroids can grow to be several centimeters in diameter and may cause symptoms like menorrhagia (prolonged or heavy menstrual bleeding), pelvic pressure or pain, and reproductive dysfunction.

Current treatments for uterine fibroids include pharmacological therapy, hysterectomy, uterine artery embolization, and hysteroscopic resection. Pharmacological therapy typically involves the administration of NSAIDS (non-steroidal anti-inflammatory drugs), estrogen-progesterone combinations, and GnRH (gonadotropin releasing hormone) analogues. However, current pharmacological therapies are largely ineffective and merely palliative. By comparison, a hysterectomy involves the surgical removal of the uterus from a patient. For this reason, a hysterectomy represents a highly effective way of ridding a patient of uterine fibroids. As a result, several hundred thousand hysterectomies are typically performed annually in the United States to treat uterine fibroids. However, despite their widespread use, hysterectomies also possess certain disadvantages, such as a loss of fertility, sexual dysfunction, and the risks commonly associated with a major surgical procedure, such as hemorrhaging, lesions, infections, pain and prolonged recovery. Uterine artery embolization involves inserting a catheter into a femoral artery and then guiding the catheter to a uterine fibroid artery. Small particles are then injected from the catheter into the fibroid artery, blocking its blood supply and causing it to eventually shrink and die. Although this procedure is less invasive than a hysterectomy, it often results in pain-related, post-surgical complications. Moreover, the physicians that are trained to perform uterine artery embolization are typically interventional radiologists, as opposed to physicians trained specifically to take care of gynecological problems, whereas the physicians trained specifically to take care of gynecological problems typically do not possess the skill to perform catheter-based uterine artery embolization.

Hysteroscopic resection typically involves inserting a hysteroscope (i.e., an imaging scope) into the uterus through the vagina, i.e., transcervically, and then cutting away the fibroid from the uterus using a device delivered to the fibroid by the hysteroscope. Hysteroscopic resections typically fall into one of two varieties. In one variety, an electrocautery device in the form of a loop-shaped cutting wire is fixedly mounted on the distal end of the hysteroscope—the combination of the hysteroscope and the electrocautery device typically referred to as a resectoscope. The transmission of electrical current to the uterus with a resectoscope is typically monopolar, and the circuit is completed by a conductive path to the power unit for the device through a conductive pad applied to the patient's skin. In this manner, tissue is removed by contacting the loop with the part of the uterus wall of interest. Examples of such devices are disclosed, for example, in U.S. Pat. No. 5,906,615, inventor Thompson, issued May 25, 1999.

In the other variety of hysteroscopic resection, an electromechanical cutter is inserted through a working channel in the hysteroscope. Tissue is then removed by contacting the cutter, which typically has a rotating cutting instrument, with the part of the uterus wall of interest. Examples of the electromechanical cutter variety of hysteroscopic resection are disclosed in, for example, U.S. Pat. No. 7,226,459, inventors Cesarini et al., issued Jun. 5, 2007; U.S. Pat. No. 6,032,673, inventors Savage et al., issued Mar. 7, 2000; U.S. Pat. No. 5,730,752, inventors Alden et al., issued Mar. 24, 1998; U.S. Patent Application Publication No. US 2006/0047185 A1, inventors Shener et al., published Mar. 2, 2006; and PCT International Publication No. WO 99/11184, published Mar. 11, 1999, all of which are incorporated herein by reference.

In both of the above-described varieties of hysteroscopic resection, prior to fibroid removal, the uterus is typically distended to create a working space within the uterus. (Such a working space typically does not exist naturally in the uterus because the uterus is a flaccid organ. As such, the walls of the uterus are typically in contact with one another when in a relaxed state.) The conventional technique for creating such a working space within the uterus is to administer a fluid to the uterus through the hysteroscope under sufficient pressure to cause the uterus to become distended. Examples of the fluid used conventionally to distend the uterus include gases like carbon dioxide or, more commonly, liquids like water or certain aqueous solutions (e.g., a saline solution or a sugar-based aqueous solution). Where resection is effected using a resectoscope, it is typically necessary that the distending fluid not be current-conducting so that electricity is not conducted to undesired locations. However, because the distending fluid is administered under pressure (which pressure may be as great as 120 mm Hg or greater), there is a risk, especially when tissue is cut, that the distending fluid may be taken up by a blood vessel in the uterus, i.e., intravasation, which uptake may be quite harmful to the patient. Because excess intravasation can lead to death, it is customary to monitor the fluid uptake on a continuous basis using a scale system.

Nevertheless, despite the aforementioned risks of intravasation, with proper monitoring of fluid uptake, hysteroscopic resection is a highly effective and safe technique for removing uterine fibroids. However, one shortcoming with hysteroscopic resection is that it typically requires that anesthesia be administered to the patient. This is because conventional resectoscopes typically have a diameter in excess of 7 mm and because conventional hysteroscopes of the type through which mechanical cutter-type devices are inserted typically have a diameter of about 9 mm. By contrast, the cervix typically cannot be dilated to a diameter greater than about 5.5 mm without causing considerable discomfort to the patient. As a result, due to the need for anesthesia, hysteroscopic resection is typically performed in a hospital operating room and, as a result, bears a large cost due to the setting and the support personnel required.

SUMMARY OF THE INVENTION

The present invention provides a novel method, system and device for tissue removal. The method, system and device as described above may be used, for example, to remove uterine fibroids and other abnormal gynecological tissues.

According to one aspect of the invention, there is provided a tissue removal device, the tissue removal device comprising (a) a housing; (b) an outer tube, the outer tube being fixed to the housing and extending distally therefrom, the outer tube including a resection window; (c) an inner tube disposed within the outer tube, the inner tube being slidable and rotatable relative to the outer tube, the inner tube comprising a distal end; and (d) a motor assembly for rotating the inner tube relative to the outer tube and, at the same time, for translationally oscillating the inner tube relative to the outer tube so that the distal end of the inner tube moves back and forth across the resection window, wherein said rotating and oscillating movements are independently controllable.

In accordance with another aspect of the present invention, there is provided a method of fluid management during a procedure at a site in a hollow organ. The method comprises the steps of accessing the hollow organ with an elongate tubular device, and introducing fluid into the hollow organ. A vacuum is applied to remove fluid through the tubular device, and a procedure is performed at the site. The device is configured such that the fluid is removed through the tubular device at a rate of no more than about 300 ml/min when the vacuum is greater than about 400 mm Hg.

The procedure comprises removing tissue at a rate of at least about 1.5 gm/min, and the procedure may be accomplished removing tissue through a lumen having a cross sectional area of no greater than about 12.0 square millimeters.

In accordance with a further aspect of the present invention, there is provided a method of removing tissue from a treatment site. The method comprises the steps of providing an elongate tubular device having at least one aspiration lumen and at least one tissue removal element. The tissue removal element is positioned at the treatment site, and activated to sever tissue. Vacuum is applied to remove severed tissue through the device. The device is configured such that severed tissue is removed at a rate of at least about 1.8 gm/min and the device has an outside diameter of no more than about 3.5 mm. The applying a vacuum step may comprise applying a vacuum of at least about 350 mm Hg.

Additional aspects, features and advantages of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts:

FIGS. 2(a) through 2(d) are bottom exploded perspective, top exploded perspective, bottom partially exploded, and fragmentary, partly in section, side views, respectively, of the morcellator assembly shown in FIG. 1;

FIG. 5(f) is a fragmentary perspective view, shown in section, of a further alternate embodiment of the inner tubular member of the morcellator assembly of FIGS. 2(a) through 2(d);

FIGS. 6(a) and 6(b) are fragmentary longitudinal section views of another embodiment of a tissue removal device constructed according to the teachings of the present invention;

FIGS. 8(a) and 8(b) are perspective and enlarged fragmentary perspective views, respectively, of a further embodiment of a tissue removal device constructed according to the teachings of the present invention;

FIG. 9 is a fragmentary perspective view of a further embodiment of a tissue removal device constructed according to the teachings of the present invention;

FIG. 10 is a fragmentary perspective view of a further embodiment of a tissue removal device constructed according to the teachings of the present invention;

FIG. 11 is a fragmentary perspective view, broken away in part, of a further embodiment of a tissue removal device constructed according to the teachings of the present invention;

FIG. 12 is a fragmentary perspective view of a further embodiment of a tissue removal device constructed according to the teachings of the present invention;

FIGS. 13(a) and 13(b) are fragmentary perspective and fragmentary side views, respectively, of a further embodiment of a tissue removal device constructed according to the teachings of the present invention;

FIG. 14 is a fragmentary perspective view of a further embodiment of a tissue removal device constructed according to the teachings of the present invention;

FIG. 17 is a fragmentary perspective view of a further embodiment of a tissue removal device constructed according to the teachings of the present invention;

FIG. 20 is a fragmentary perspective view of a further embodiment of a tissue removal device constructed according to the teachings of the present invention;

FIGS. 21(a) and 21(b) are fragmentary perspective views of a further embodiment of a tissue removal device constructed according to the teachings of the present invention, the tissue removal device being shown with its cutting element in its distal position prior to being expanded and in its distal position after being expanded, respectively;

FIGS. 22(a) and 22(b) are fragmentary perspective views of a further embodiment of a tissue removal device constructed according to the teachings of the present invention, the tissue removal device being shown with its cutting element in closed and open positions, respectively;

FIG. 23 is a fragmentary perspective view of a further embodiment of a tissue removal device constructed according to the teachings of the present invention;

FIGS. 25(a) and 24(b) are fragmentary perspective views of a further embodiment of a tissue removal device constructed according to the teachings of the present invention, the tissue removal device being shown with its cutting element in closed and open positions, respectively;

FIG. 35 is a fragmentary perspective view of a further embodiment of a tissue removal device constructed according to the teachings of the present invention;

FIG. 36 is a fragmentary perspective view of a further embodiment of a tissue removal device constructed according to the teachings of the present invention;

FIG. 37 is a fragmentary perspective view of a further embodiment of a tissue removal device constructed according to the teachings of the present invention;

FIGS. 38(a) and 38(b) are fragmentary perspective and longitudinal section views, respectively, of a further embodiment of a tissue removal device constructed according to the teachings of the present invention;

FIG. 42 is a fragmentary perspective view of a further embodiment of a tissue removal device constructed according to the teachings of the present invention;

FIG. 43 is a fragmentary perspective view of a further embodiment of a tissue removal device constructed according to the teachings of the present invention;

FIG. 44 is a fragmentary perspective view of a further embodiment of a tissue removal device constructed according to the teachings of the present invention;

FIG. 45 is a fragmentary perspective view of a further embodiment of a tissue removal device constructed according to the teachings of the present invention;

FIG. 46 is a fragmentary perspective view of a further embodiment of a tissue removal device constructed according to the teachings of the present invention;

FIG. 49 is a fragmentary perspective view of a further embodiment of a tissue removal device constructed according to the teachings of the present invention;

FIG. 50 is a fragmentary perspective view of a further embodiment of a tissue removal device constructed according to the teachings of the present invention;

FIG. 51 is a fragmentary side view of a further embodiment of a tissue removal device constructed according to the teachings of the present invention;

FIG. 52 is a fragmentary perspective view of a further embodiment of a tissue removal device constructed according to the teachings of the present invention;

FIGS. 53(a) and 53(b) are fragmentary perspective and fragmentary section views, respectively, of further embodiment of a tissue removal device constructed according to the teachings of the present invention.

FIG. 55 reports the results of a series of experiments in which vacuum pressure and translation speed were maintained constant, and cutter rotational speeds were varied.

FIG. 56 reports data from a series of experiments in which rotational speed was maintained at a constant, vacuum pressure was maintained at a constant, and translation speeds were varied.

FIG. 57 reports data from a series of experiments in which rotation speed was maintained constant, translation speed was maintained constant and vacuum pressure was varied.

DETAILED DESCRIPTION OF THE PREFERRED EMBODIMENT

The present invention is described below primarily in the context of instruments and procedures optimized for performing one or more therapeutic or diagnostic gynecologic or urologic procedures such as the removal of uterine fibroids or other abnormal uterine tissue. However, the morcellators and related procedures of the present invention may be used in a wide variety of applications throughout the body, through a variety of access pathways.

For example, the morcellators of the present invention can be optimized for use via open surgery, less invasive access such as laparoscopic access, or minimally invasive procedures such as via percutaneous access. In addition, the devices of the present invention can be configured for access to a therapeutic or diagnostic site via any of the body's natural openings to accomplish access via the ears, nose, mouth, and via trans rectal, urethral and vaginal approach.

In addition to the performance of one or more gynecologic and urologic procedures described in detail herein, the systems, methods, apparatus and devices of the present invention may be used to perform one or more additional procedures, including but not limited to access and tissue manipulation or removal from any of a variety of organs such as the bladder, lung, stomach, bowel, esophagus, oral cavity, rectum, nasal sinus, Eustachian tubes, heart, gall bladder, arteries, veins, and various ducts. Routes of access include but are not limited to trans-cervical; trans-vaginal-wall; trans-uteral; transvesicle; trans-urethral; and other routes.

Figure 1:
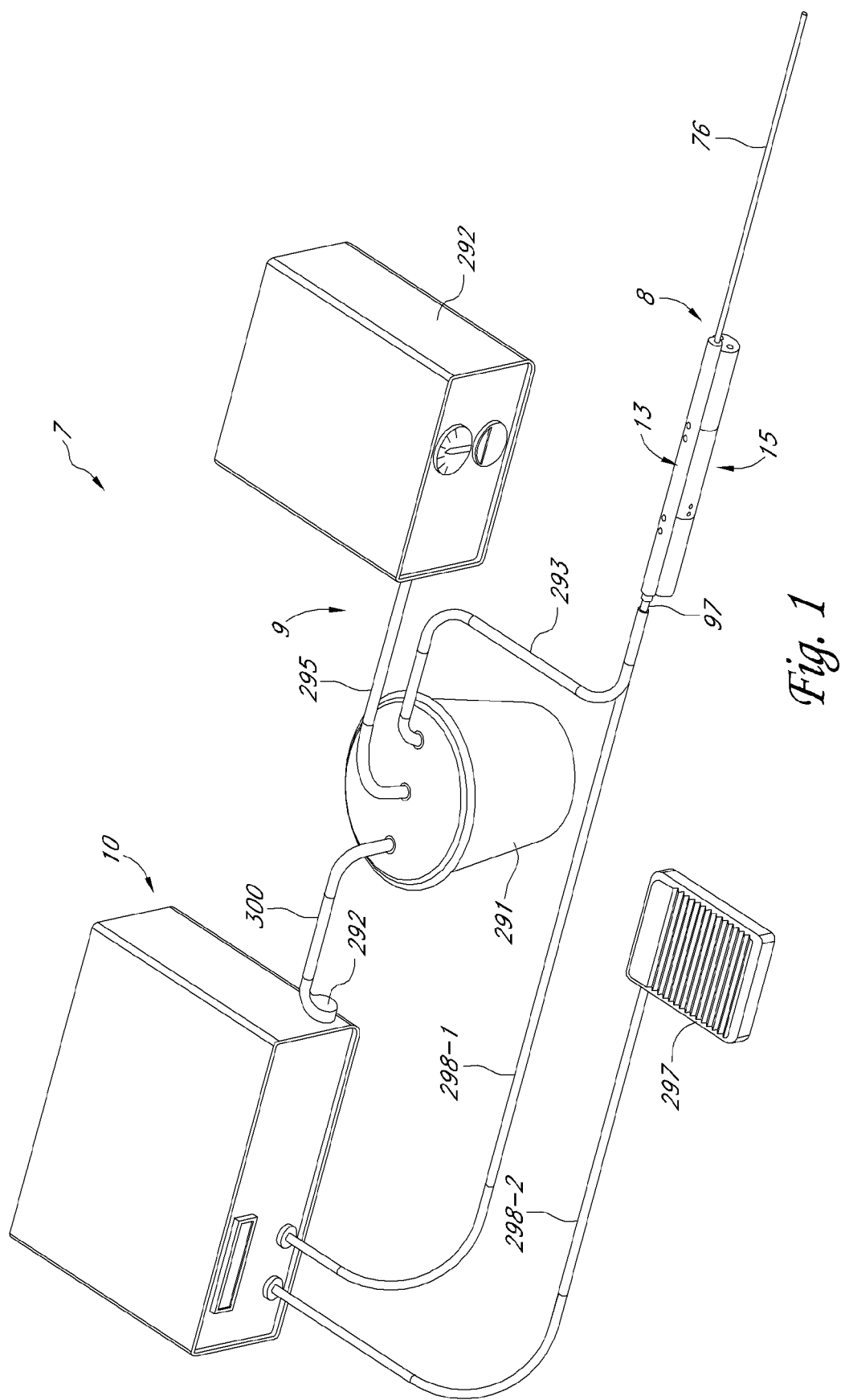
FIG. 1 is a perspective view of one embodiment of a tissue removal system constructed according to the teachings of the present invention.
Figure 2A:
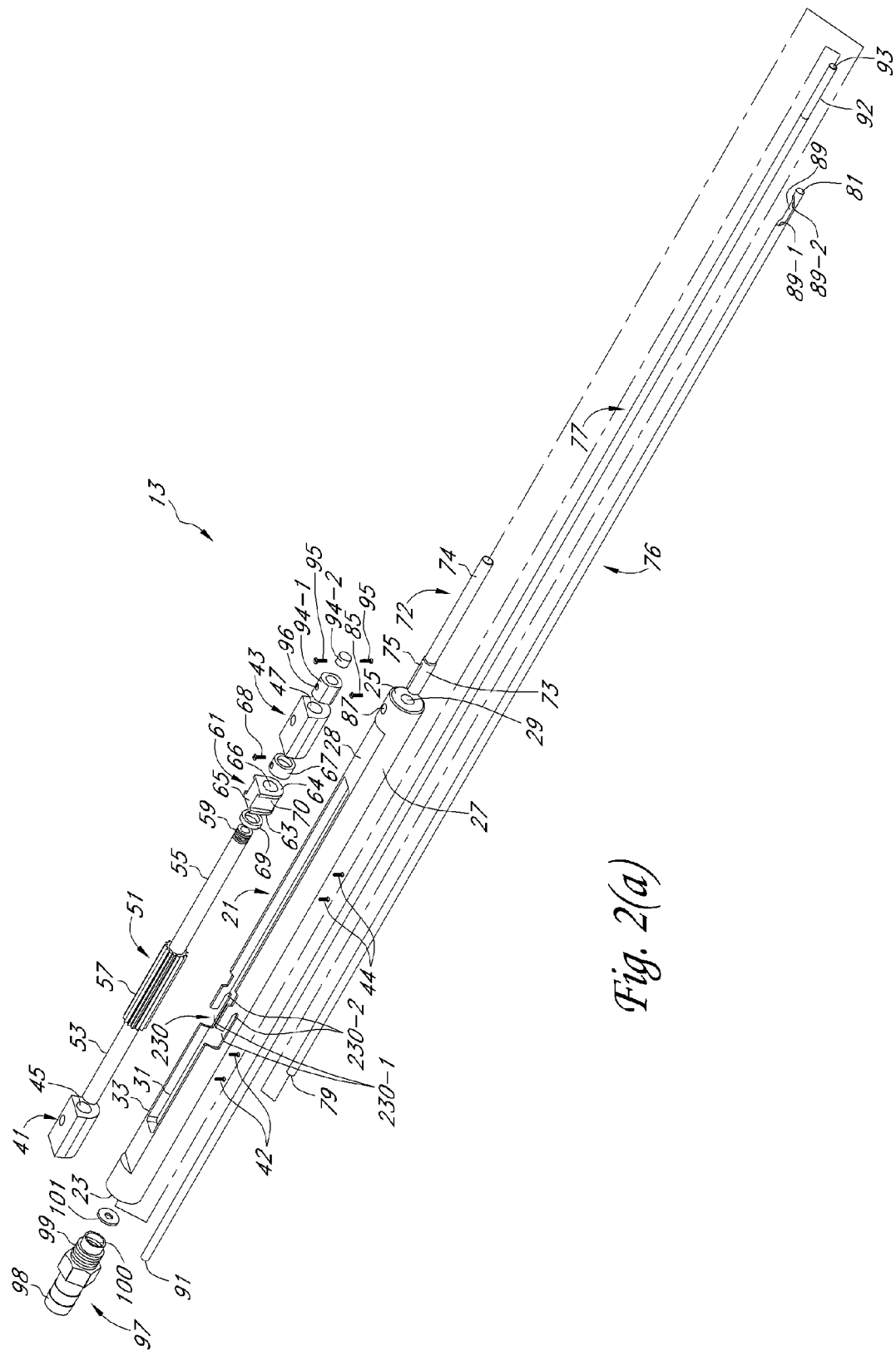
Figure 2B:
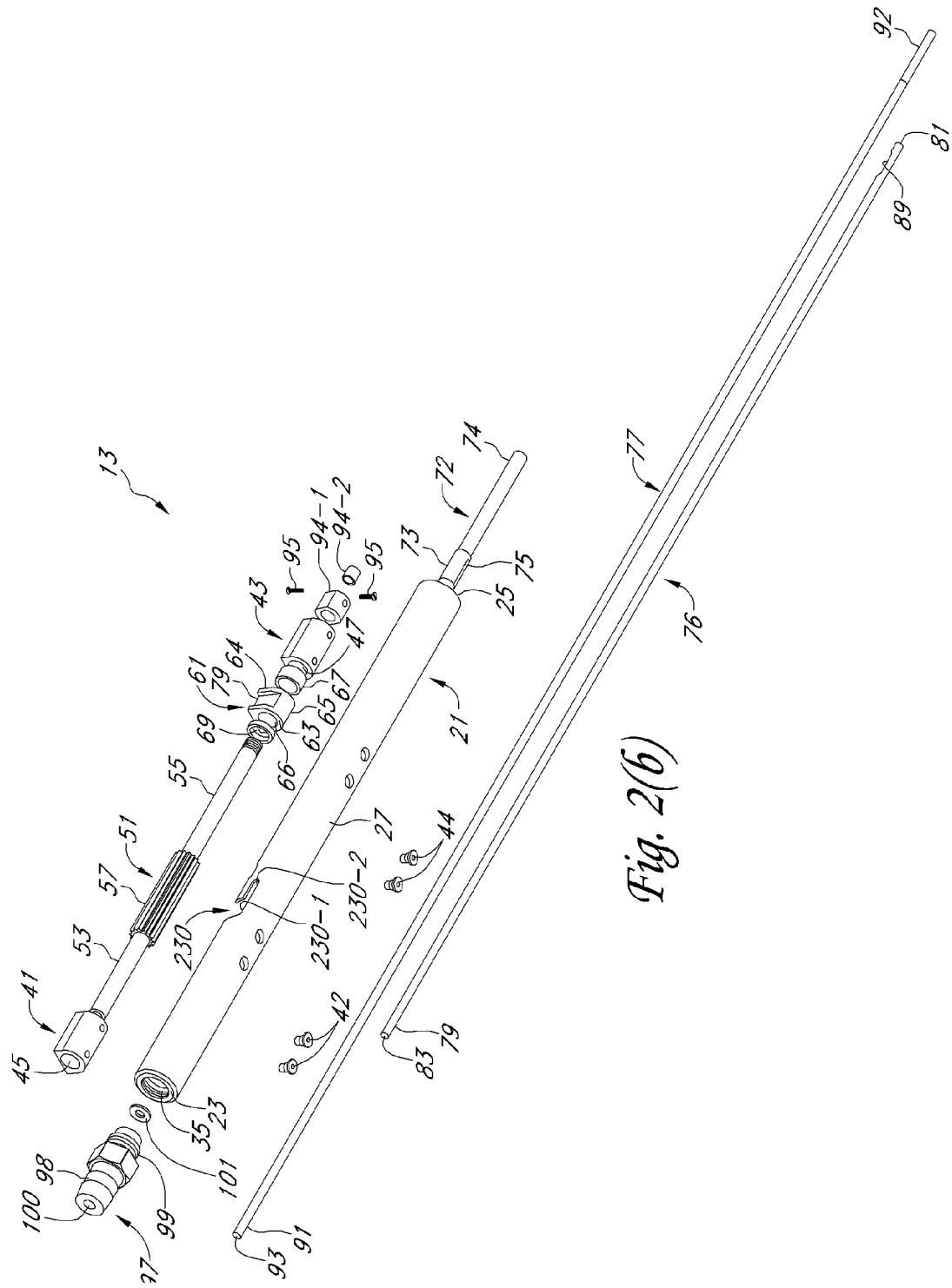
Figure 2D:
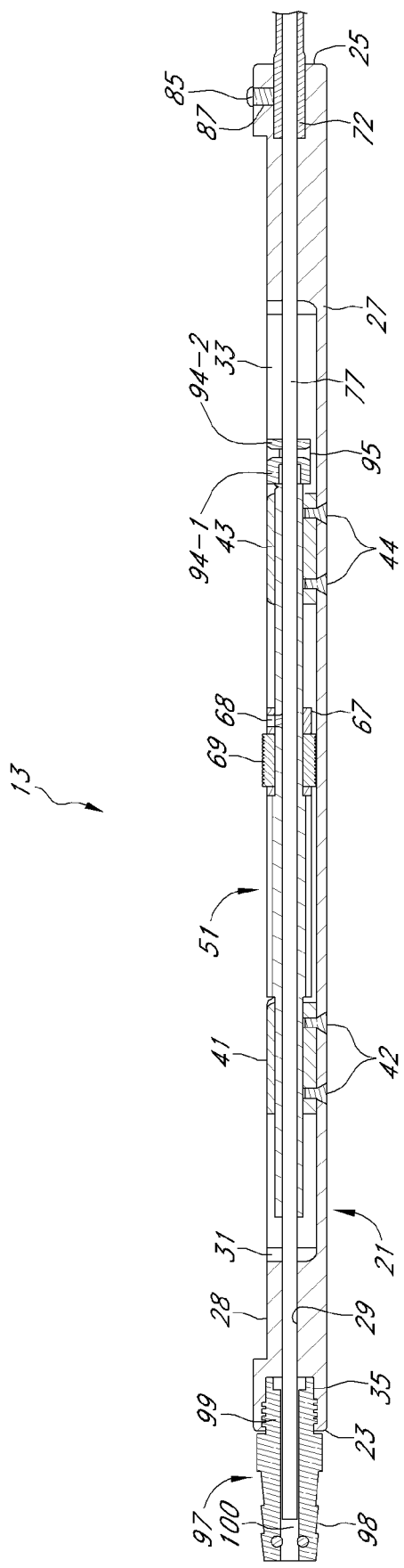

Referring now to FIG. 1, there is shown a perspective view of one embodiment of a tissue removal system, the tissue removal system being constructed according to the teachings of the present invention and being represented generally by reference numeral 7.

System 7 is particularly well-suited for removing uterine fibroids and other abnormal gynecological tissues. However, it should be understood that system 7 is not limited to such a use and may be used in other anatomies that may be apparent to those of ordinary skill in the art.

System 7 may comprise a tissue removal device 8, a vacuum assembly 9, and a control unit 10.

Tissue removal device 8, in turn, may comprise a morcellator assembly 13 and a drive assembly 15, morcellator 13 being removably mounted on drive assembly 15 in the manner described further below.

Referring now to FIGS. 2(a) through 2(d), morcellator assembly 13 may be seen in greater detail. Morcellator assembly 13 may comprise a housing 21. Housing 21, which may be an elongated unitary structure made of a rigid polymer or metal, may be a generally tubular member shaped to include a proximal end 23, a distal end 25, and a side wall 27. Side wall 27 may be generally cylindrical, with a portion 28 of its bottom surface being beveled. A longitudinal lumen 29 may extend from proximal end 23 to distal end 25. An intermediate portion 31 of lumen 29 may be expanded in diameter and may be accessible through an opening 33 in side wall 27. A proximal portion 35 of lumen 29 extending distally from proximal end 23 to a point spaced proximally from intermediate portion 31 may be expanded in diameter and may be internally threaded.

Morcellator assembly 13 may additionally comprise a pair of tubular bushings 41 and 43. Bushing 41, which may be a unitary structure made of a rigid polymer or metal, may be seated within intermediate portion 31 of lumen 29, near its proximal end, and may be fixedly secured to housing 21 with screws 42. Bushing 43, which may be a unitary structure made of a rigid polymer or metal, may be seated within intermediate portion 31 of lumen 29, near its distal end, and may be fixedly secured to housing 21 with screws 44. Bushing 41 may be shaped to include a bore 45, and bushing 43 may be shaped to include a bore 47, bores 45 and 47 being coaxially aligned with lumen 29 of housing 21.

Morcellator assembly 13 may further comprise an elongated shaft 51. Shaft 51, which may be a unitary structure made of brass or another suitable rigid metal or polymer, may be shaped to include a proximal portion 53, a distal portion 55, an intermediate portion 57, and a longitudinal bore 59. Proximal portion 53 of shaft 51 may be slidably mounted in bore 45 of bushing 41 and may be sized to freely rotate therewithin. Distal portion 55 of shaft 51 may be slidably mounted in bore 47 of bushing 43 and may be sized to freely rotate therewithin. Intermediate portion 57 of shaft 51 may be positioned between bushings 41 and 43 and may be in the shape of a gear having an enlarged external diameter relative to proximal portion 53 and distal portion 55.

Morcellator assembly 13 may further comprise a translational coupling block 61. Block 61, which may be a unitary structure made of a rigid polymer or metal, may be a tubular member shaped to include a proximal end 63, a distal end 64, a side wall 65, and a longitudinal bore 66. Block 61 may be coaxially mounted over proximal portion 53 of shaft 51, with bore 66 being sized relative to proximal portion 53 so that proximal portion 53 may freely rotate within bore 66. Side wall 65 of block 61 may be shaped to correspond generally to the shape of intermediate portion 31 of lumen 29. In this manner, block 61 may be kept rotationally stationary within housing 21. Block 61 may be translationally fixed relative to shaft 51 with a retaining ring 67 inserted coaxially over proximal portion 53 and secured to proximal portion 53 with a set screw 68. A washer 69 may be inserted coaxially over proximal end 53 of shaft 51 between distal end 63 of block 61 and intermediate portion 57 of shaft 51 to prevent any wear caused by contact between intermediate portion 57 against distal end 63 of block 61 as intermediate portion 57 rotates. Side wall 65 of block 61 may further be shaped to include a waist 70 of reduced external diameter. In this manner, with block 61 coaxially mounted over proximal portion 53 of shaft 51, a pair of slots 71-1 and 71-2 may be formed between block 61 and housing 21.

Morcellator assembly 13 may further comprise a strain relief member 72. Strain relief member 72, which may be a unitary structure made of a rigid polymer or metal, may be a tubular member shaped to include a proximal portion 73 and a distal portion 74. Proximal portion 73 may be slightly greater in diameter than distal portion 74 and may include a bifurcating slot 75. Proximal portion 73 of strain relief member 72 may be disposed within the distal portion of lumen 29, with distal portion 74 of strain relief member 72 extending distally from distal end 25 of housing 21 for a short distance, such as, for example, approximately 2 inches.

Should the device be used in an operating room setting where general anesthesia is available, the diameter of the outer tubular member 76 can be can be increased to maximize tissue removal. The outer tubular member 76 would have a diameter generally less than about 12 mm, preferably less than about 11 mm, and for certain applications less than 10 mm. Depending upon the particular clinical application, morcellators can readily be constructed in accordance with the present invention having an outer diameter of no more than about 9 mm, in some applications less than 8 about mm, preferably less than 7 mm, and more preferably less than 6 mm where OD is desirably minimized.

Morcellator assembly 13 may further comprise a cutting mechanism. In the present embodiment, the cutting mechanism may comprise an outer tubular member 76 and an inner tubular member 77, inner tubular member 77 moving rotationally and, at the same time, oscillating translationally relative to outer tubular member 76 in the manner to be described further below. Outer tubular member 76, which may be a unitary structure made of stainless steel or another similarly suitable material, may be shaped to include an open proximal end 79, a closed distal end 81, and a lumen 83 extending from open proximal end 79 to a point just prior to closed distal end 81. Member 76 may be coaxially mounted within strain relief member 72, with proximal end 79 of member 76 disposed within proximal portion 73 of strain relief member 72 and with distal end 81 of member 76 extending distally beyond distal portion 74 of strain relief member 72 for an extended distance, such as, for example, five inches. The combination of proximal end 79 of member 76 and proximal portion 73 of strain relief member 72 may be securely retained in housing 21 using a screw 85 inserted through an opening 87 in housing 21, screw 85 pressing proximal portion 73 of strain relief member 72 tightly against proximal end 79 of member 76.

Outer tubular member 76 may be further shaped to include a resection window 89 into which tissue may be captured and drawn, window 89 being located proximate to distal end 81, such as, for example, 0.25 inch from distal end 81. Window 89 may be shaped to include a proximal end 89-1 and a distal end 89-2. Proximal end 89-1 may slope gradually proximally, and distal end 89-2 may slope gradually distally. More specifically, window 89 may have a length of approximately 0.55 inch, proximal end 89-1 may be a radial end having a radius of curvature of, for example, 0.085 inch, and distal end 89-2 may be a radial end having a radius of curvature of, for example, 0.150 inch. Window 89 may extend over a substantial portion of the circumference of tubular member 76, such as, for example, about 60% of the circumference.

Outer tubular member 76 may have an outer diameter less than about 5.5 mm. However, in order to reduce the risk of injury to the patient and in order to obviate the need for anesthesia to be administered to the patient, outer tubular member 76 preferably has an outer diameter less than about 5 mm, more preferably less than 4 mm, even more preferably less than 3 mm, and still even more preferably less than 2 mm.

Inner tubular member 77, which may be an elongated unitary structure made of stainless steel or another similarly suitable material, may be shaped to include a proximal end 91, a distal end 92, and a longitudinal lumen 93. Distal end 92 may be shaped to include an external bevel, such as, for example, an external bevel of approximately 20 degrees. An intermediate portion of tubular member 77 may be received within bore 59 of shaft 51 and may be fixedly coupled to shaft 51 for translational and rotational movement therewith using a retaining ring 94-1, a slotted sleeve 94-2 and a pair of set screws 95. The proximal portion of ring 94-1 may be screwed onto the distal end of shaft 51, with the distal portion of ring 94-1 extending over member 77. Sleeve 94-2 may be inserted coaxially between member 77 and ring 94-1, and set screws 95 may be inserted through a transverse opening 96 in retaining ring 94-1 to couple ring 94-1 and sleeve 94-2 to member 77. Tubular member 77 may have a suitable length so that, when tubular member 77 is in a fully retracted (i.e., proximal) position, proximal end 91 of tubular member 77 may extend proximally a short distance from proximal end 23 of housing 21 and distal end 92 of tubular member 77 may be withdrawn sufficiently to permit tissue to enter window 89. At the same time, tubular member 77 may have a length so that, when tubular member 77 is in a fully advanced (i.e., distal) position, distal end 92 of tubular member 77 may be positioned distally of distal end 89-2 of window 89.

Morcellator assembly 13 may further comprise a fitting 97. Fitting 97, which may be a unitary structure made of a rigid polymer or metal, may be a tubular member shaped to include a proximal portion 98, a distal portion 99 and a longitudinal lumen 100. Proximal portion 98, which may be barbed, may be coupled through a length of tubing to vacuum assembly 9. Distal portion 99 of fitting 97 may be externally threaded for mating engagement with proximal portion 35 of housing 21. Lumen 100 of fitting 97 may be dimensioned to slidably receive proximal end 91 of tubular member 77. An O-ring 101 may be disposed within lumen 100 to provide a seal around tubular member 77.

Figure 3A:
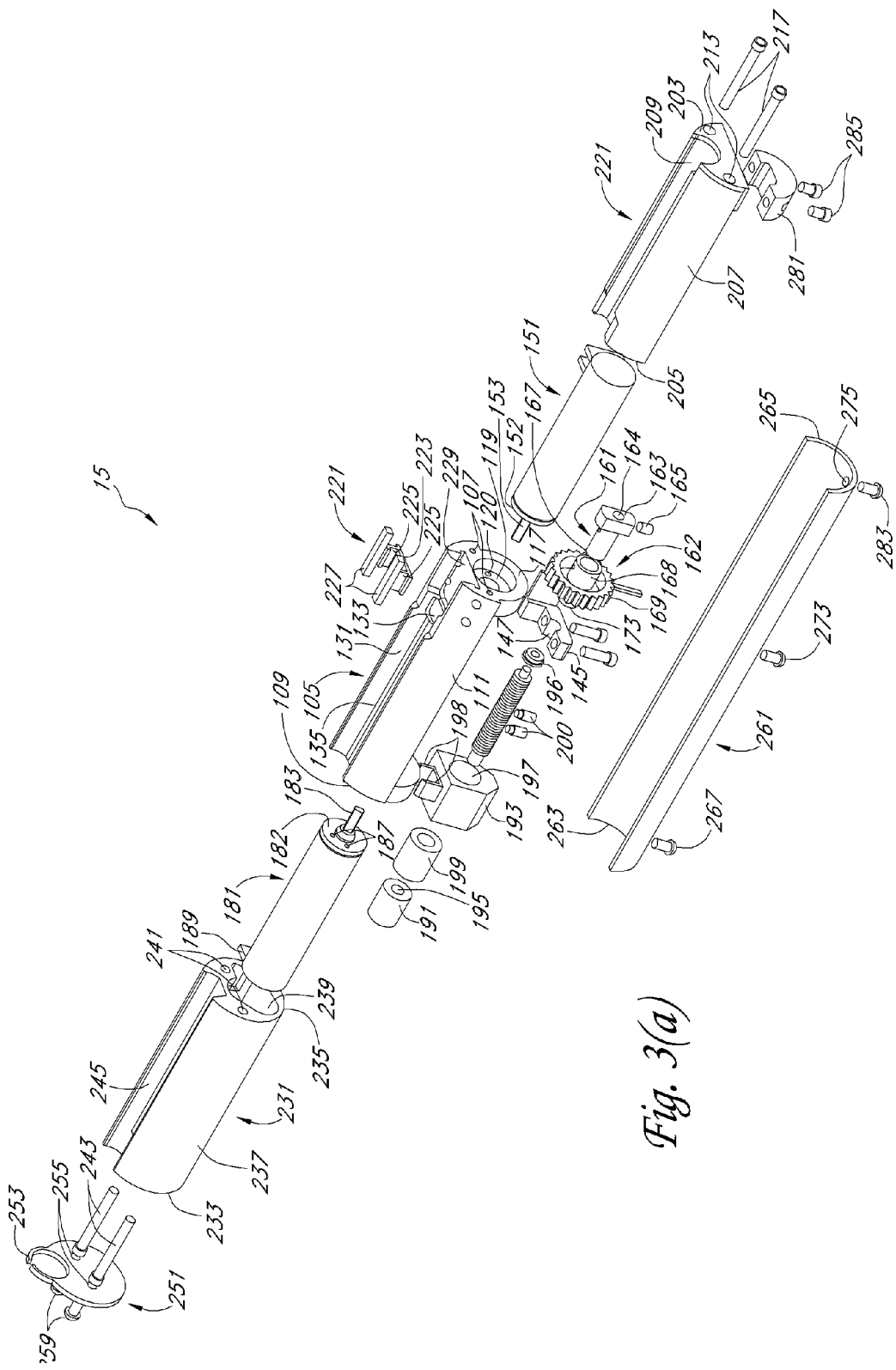
FIGS. 3(a) and 3(b) are partially exploded top perspective and partially exploded bottom perspective views, respectively, of the drive assembly shown in FIG. 1.
Figure 3B:
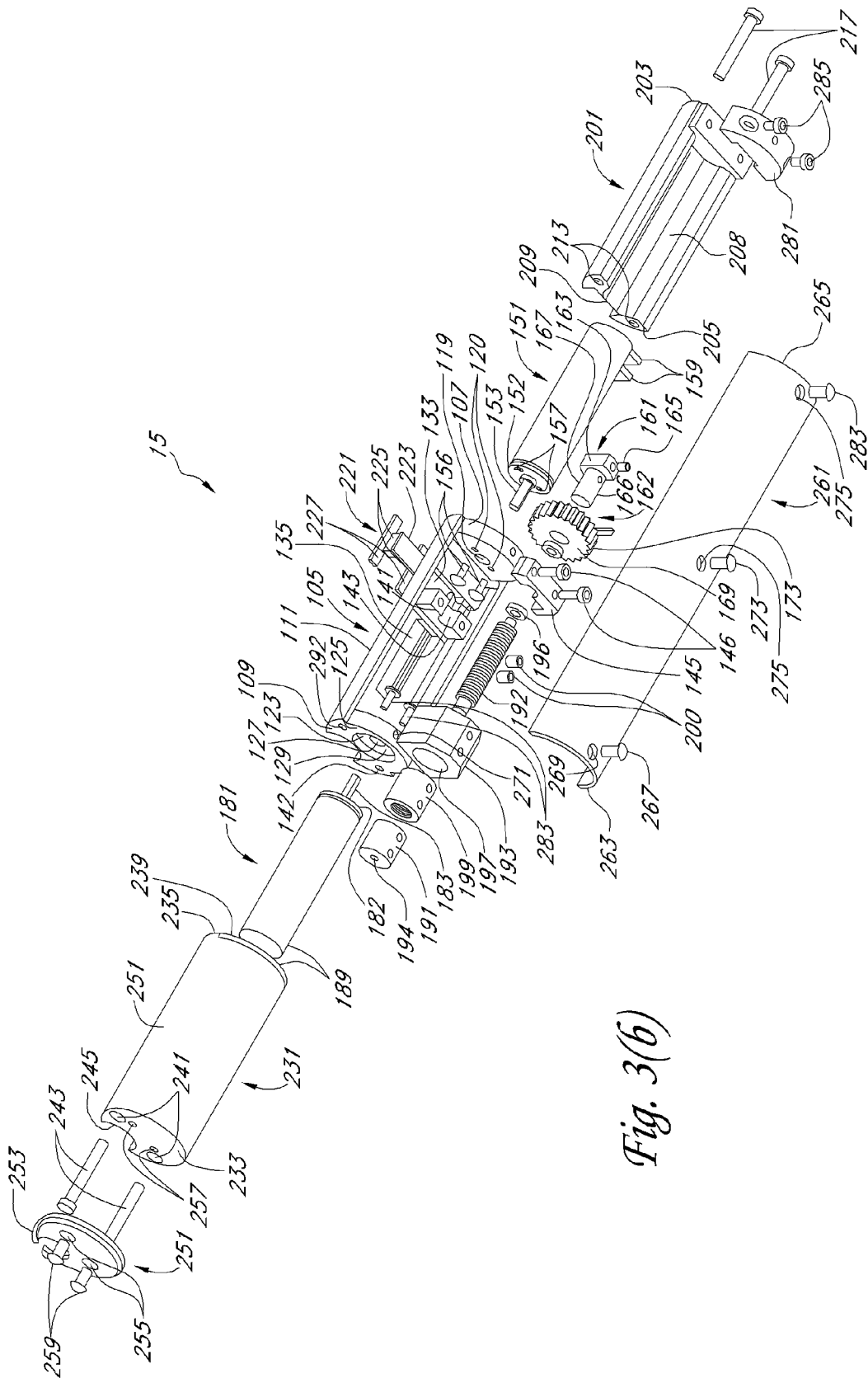
Figure 4A:
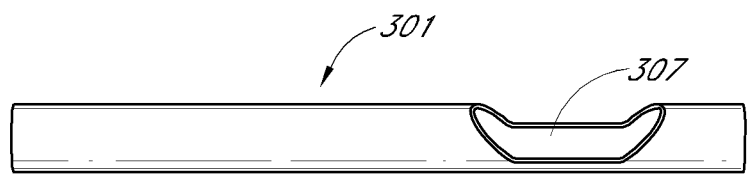
FIGS. 4(a) through 4(e) are fragmentary perspective views of alternate embodiments of the outer tubular member of the morcellator assembly of FIGS. 2(a) through 2(d)
Figure 4B:
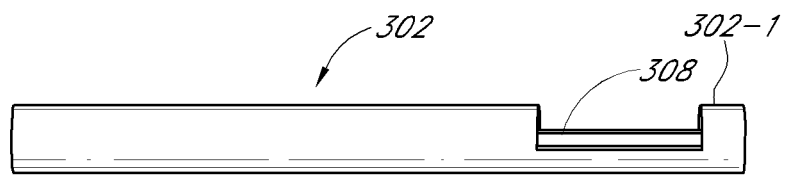
Figure 4C:
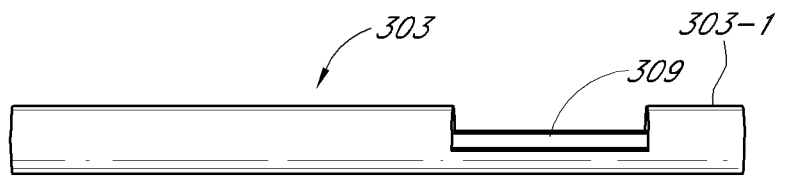
Figure 4D:
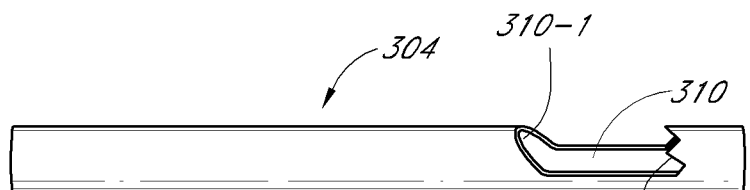
Figure 4E:
Figure 5A:
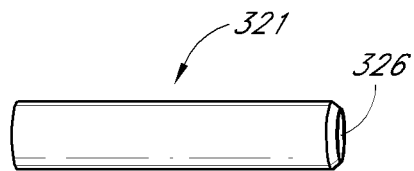
FIGS. 5(a) through 5(e) are fragmentary perspective views of alternate embodiments of the inner tubular member of the morcellator assembly of FIGS. 2(a) through 2(d)
Figure 5B:
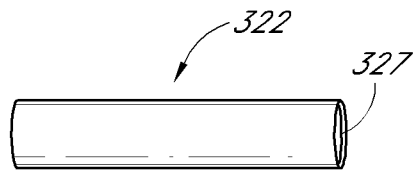
Figure 5C:
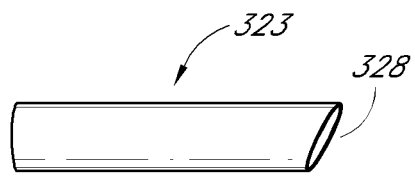
Figure 5D:
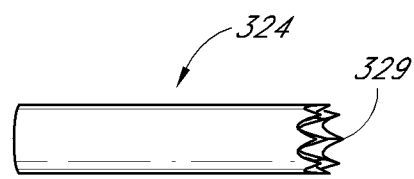
Figure 5E:
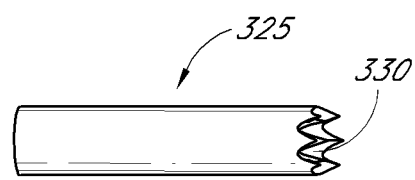

Referring now to FIGS. 3(a) and 3(b), drive assembly 15 may be seen in greater detail. Drive assembly 15 may include a main body 105. Main body 105, which may be a unitary structure made of a rigid polymer or metal, may be a generally trough-shaped member shaped to include a distal end 107, a proximal end 109, and a side wall 111. Distal end 107 may be generally circular and may include a distal surface that includes a central portion 115 and a peripheral portion 117. Central portion 115 may be recessed relative to peripheral portion 117. A central transverse opening 119 may be provided in central portion 115, and a pair of smaller transverse openings 120 may be provided in central portion 115 on opposite sides of central opening 119. Proximal end 109 may be generally circular and may include a proximal surface that includes a central portion 123 and a peripheral portion 125. Central portion 123 may be recessed relative to peripheral portion 125. A central transverse opening 127 may be provided in central portion 123, and a pair of smaller transverse openings 129 may be provided in central portion 123 on opposite sides of central opening 127. Side wall 111 may extend from distal end 107 to proximal end 109 but only over about the top half of their respective circumferences. A longitudinal groove 131 may be provided along the outer surface of side wall 111 to receive a corresponding portion of housing 21 of morcellator assembly 13. Groove 131 may include a first transverse slot 133 extending though side wall 111 and a second transverse slot 135 extending through side wall 111. First transverse slot 133 may be spaced a short distance from distal end 107 and may be oriented generally circumferentially relative to side wall 111. Second transverse slot 135 may be spaced a short distance from proximal end 109 and from first transverse slot 133 and may be oriented generally longitudinally relative to side wall 111. The inner surface of side wall 111 may additionally be shaped to include a block 141 located between first transverse slot 133 and second transverse slot 135. Block 141 may be shaped to include an exterior groove 143 on its bottom surface, groove 143 extending parallel to second transverse slot 135. A bracket 145, which may be a unitary structure made of a rigid polymer or metal, may be secured to the bottom surface of block 141 with a pair of screws 146. Bracket 145 may be shaped to include a groove 147 on its top surface that is complementarily shaped to groove 143, with grooves 143 and 147 jointly defining a channel of generally cylindrical shape.

Drive assembly 15 may additionally comprise a mechanism for driving rotational movement of inner tubular member 77. Such a mechanism may comprise a first motor 151. Motor 151, in turn, may comprise a first end 152 having a shaft 153 extending therefrom. First end 152 may be received within central portion 115 of distal end 107 of body 105 and may be secured thereto with screws 156 inserted through openings 120 and into complementary openings 157 in first end 152 of motor 151. With motor 151 thus secured to distal end 107, shaft 153 may extend through central transverse opening 119 and may freely rotate therewithin. Cables 159 may be used to connect motor 151 to control unit 10.

In addition, the aforementioned mechanism for driving rotational movement of inner tubular member 77 may further comprise a coupling block 161 and a gear 162. Coupling block 161, which may be a unitary structure made of a rigid polymer or metal, may be shaped to include a distal base 163 and a proximal post, the proximal post extending proximally from base 163. Base 163 may be shaped to include a cavity 164 accessible from its distal end into which shaft 153 of motor 151 may be received and secured with a screw 165, thereby mechanically coupling shaft 153 to block 161. The proximal post may be shaped to include a distal portion 166 of increased diameter and a proximal portion 167 of decreased diameter. Gear 162, which may be a unitary member made of a rigid polymer or metal, may be shaped to include a distal tube 168 and a proximal toothed wheel 169. Tube 168 may be coaxially mounted on portion 166 of block 161 and mechanically coupled thereto with a screw 170. Wheel 169 may be positioned so that a portion of wheel 169 extends through slot 133 for engagement with intermediate portion 57 of shaft 51. In this manner, rotation of wheel 169 causes the rotation of shaft 51. Proximal portion 167 of post 165, which may extend proximally a short distance beyond wheel 169, may be seated within a bearing 173, bearing 173 being seated within the distal end of the channel jointly defined by block 141 and bracket 145.

Drive assembly 15 may further comprise a mechanism for driving oscillating translational movement of inner tubular member 77. Such a mechanism may comprise a second motor 181. Motor 181, in turn, may comprise a first end 182 having a shaft 183 extending therefrom. First end 182 may be received within central portion 123 of proximal end 109 of body 105 and may be secured thereto with screws 186 inserted through openings 129 and into complementary openings 187 in first end 182 of motor 181. With motor 181 thus secured to proximal end 109, shaft 183 may extend through central transverse opening 127 and may freely rotate therewithin. A cable 189 may be used to connect motor 181 to control unit 10.

In addition, the aforementioned mechanism for driving oscillating translational movement of inner tubular member 77 may further comprise a coupling block 191, a threaded bolt 192, and a carriage 193. Coupling block 191, which may be a unitary structure made of a rigid polymer or metal, may be shaped to include a proximal opening 194 and a distal opening 195. Proximal opening 194 may be dimensioned to securely receive shaft 183 of motor 181, thereby mechanically coupling shaft 183 to block 191. Distal opening 195 may be dimensioned to securely receive the proximal end of threaded bolt 192, thereby mechanically coupling bolt 192 to block 191. The distal end of bolt 192 may be seated within a bearing 196, which, in turn, may be seated within the proximal end of the channel jointly defined by block 141 and bracket 145. Carriage 193, which may be a unitary structure made of a rigid polymer or metal, may be shaped to include a bore 197 and a pair of upwardly extending tines 198. A rigid collar 199 may be fixedly mounted within bore 197 of carriage 193 using a pair of screws 200. Collar 199 may be internally threaded to engage bolt 192. In this manner, as bolt 192 rotates, carriage 193 moves translationally along the longitudinal axis of bolt 192, with proximal or distal translational movement of carriage 193 effected by the clockwise or counterclockwise rotation, respectively, of bolt 192. Carriage 193 may be mechanically coupled for translational movement to shaft 51 by tines 198, with tines 198 extending through slot 135 of body 105 and being received within slots 71-1 and 71-2 of morcellator assembly 13.

As can be appreciated from the above description, the speed at which inner tubular member 77 rotates and the speed at which inner tubular member 77 oscillates translationally are separately and independently controlled, with the rotation of inner tubular member 77 being controlled by motor 151 and with the oscillating translation of inner tubular member 77 being controlled by motor 181.

Drive assembly 15 may further comprise a body 201. Body 201, which may be a unitary structure made of a rigid polymer or metal, may be shaped to include a distal end 203, a proximal end 205, a side wall 207, and a cavity 208. Distal end 203 may be generally semi-circular in shape, and proximal end 205 may be generally semi-annular in shape. Side wall 207 may be semi-annular in transverse cross-section and may extend from distal end 203 to proximal end 205. A longitudinal groove 209, similar in shape to groove 131 of body 105, may be provided along the top, outer surface of side wall 207 to receive a corresponding portion of housing 21 of morcellator assembly 13. Cavity 208 may be dimensioned to receive motor 151. A pair of longitudinal lumens 213 may be provided in body 201, lumens 213 extending through distal end 203, proximal end 205, and side wall 207. Lumens 213 may be aligned with corresponding threaded cavities 215 in body 105 so that proximal end 205 of body 201 and may be fixed to distal end 107 of body 105 using screws 217 inserted through body 201 and into cavities 215.

Drive assembly 15 may further comprise a locking clip 221. Locking clip 221, which may be a unitary structure made of a rigid polymer or metal, may be shaped to include a base 223, a pair of parallel legs 225, and a pair of parallel feet 227. Legs 225 may extend upwardly from base 223, with legs 225 being spaced inwardly a short distance from the ends of base 223. Feet 227 may extend transversely from legs 225. Base 223 may be received within a matingly-shaped recess 229 provided on body 105 and may be securely retained within recess 229 by securing body 201 to body 105. With clip 221 thus mounted on body 105, legs 225 extend upwardly beyond body 105 and may be inserted into corresponding L-shaped slots 230 in housing 21 of morcellator assembly 13. In this manner, clip 221 may be used to reversibly and lockably couple drive assembly 15 to morcellator assembly 13. More specifically, to lockably couple drive assembly 15 to morcellator assembly 13, one may insert feet 227 into the proximal portions 230-1 of slots 230 and may then slide feet 227 distally to the distal portions 230-2 of slots 230. To uncouple drive assembly 15 from morcellator 13, feet 227 may be slid proximally from distal portions 230-2 to proximal portions 230-1 and may then be removed from slots 230.

Drive assembly 15 may further comprise a body 231. Body 231, which may be a unitary structure made of a rigid polymer or metal, may be a generally cylindrical member shaped to include a proximal end 233, a distal end 235, and a side wall 237. A cavity 239 may extend proximally from distal end 235, cavity 239 being dimensioned to receive substantially all but first end 182 and shaft 183 of motor 181. A pair of longitudinal lumens 241 may be provided in body 231, lumens 241 extending through proximal end 233, distal end 235, and side wall 237. Lumens 241 may be aligned with corresponding threaded cavities 242 in body 105 so that distal end 235 of body 231 may be fixed to proximal end 109 of body 105 using screws 243 inserted through body 231 and into cavities 242. A groove 245 may extend longitudinally from proximal end 233 to distal end 235 along the top surface of side wall 237. Groove 245 may be aligned with groove 131 of body 105 in order to receive a corresponding portion of housing 21 of morcellator assembly 13.

Drive assembly 15 may further comprise an endplate 251. Endplate 251, which may be a unitary structure made of a rigid polymer or metal, may be a generally disc-shaped structure shaped to include a retaining loop 253 at its top. Retaining loop 253 may be dimensioned to receive the proximal end of housing 21 of morcellator assembly 13. A pair of openings 255 may be provided in endplate 251. Openings 255 may be aligned with corresponding threaded cavities 257 in body 231 so that endplate 241 may be fixed to proximal end 233 of body 231 using screws 259 inserted through endplate 241 and into cavities 257.

Drive assembly 15 may further comprise a cover 261. Cover 261, which may be a unitary structure made of a rigid polymer or metal, may be in the shape of a half-pipe having a proximal end 263 and a distal end 265. Cover 261 may be dimensioned to complement side walls 111 and 207 of bodies 105 and 201, respectively. In addition, cover 261 may be fixed to body 105 with a screw 267 inserted through an opening 269 in cover 261 and into a corresponding cavity 271 in proximal end 109 of body 105 and with a screw 273 inserted through an opening 275 in cover 261 and into a corresponding cavity 277 in distal end 107 of body 105. Additionally, cover 261 may be fixed to body 201 by joining cover 261 to a block 281 using a screw 283 and by joining block 281 to distal end 203 of body 201 using a pair of screws 285.

Referring back now to FIG. 1, vacuum assembly 9 may include a specimen collection container 291 and a vacuum source 292. The distal end of an evacuation tube 293 may be inserted over fitting 97 and may be secured thereto by a friction fit, and the proximal end of evacuation tube 293 may be coupled to a first port 294 of container 291. The distal end of a tube 295 may be coupled to a second port 296 of container 291, and the proximal end of tube 295 may be coupled to vacuum source 292. In this manner, vacuum source 292 may be used to apply suction to device 8, and any withdrawn tissue, liquids or similar matter suctioned through device 8 may be collected in container 291.

Control unit 10, which may be coupled to a source of electricity, such as an AC wall outlet, using a power cord (not shown), may include electronics (not shown) for controlling the operation of motors 151 and 181 using a cable 298-1 connected to cables 159 and 189. A foot pedal 297 may be coupled to control unit 10 by a cable 298-2 and may be used as a power switch to selectively activate or de-activate motors 151 and 181. Control unit 10 may further include a vacuum sensor 299, which may be coupled to container 291 by a tube 300, so that the pressure within container 291 may be monitored by control unit 10. In this manner, a sudden increase in vacuum pressure may indicate that a clog has occurred. The presence of a clog may be indicated via an alarm (not shown) located on control unit 10. The detection of a clog is often a clear indication that the further operation of device 8 may only aggravate the clogging situation and that a cessation of tissue removal may be necessary. Control unit 10 may be configured to synchronize actuation of drive assembly 15 with actuation of vacuum source 292. In this manner, turning on drive assembly 15 will turn on vacuum source 292 at the same time. Correspondingly, vacuum source 292 may be deactivated whenever drive assembly 15 is turned off.

In use, the distal end of a hysteroscope may be inserted transcervically into a patient, and a suitable fluid may be conducted through the inlet fluid port of the hysteroscope into the uterus until the uterus is distended. Observation of the uterus and detection of fibroids or other abnormal gynecological tissues may then be performed using the visualization channel of the hysteroscope. The distal ends of outer tubular member 76 and inner tubular member 77 may be inserted through a working channel of the hysteroscope and into the uterus, with the remainder of system 7 remaining proximal to the hysteroscope. Device 8 may then be manipulated so that window 89 of outer tubular member 76 may be positioned in proximity to the fibroid or other targeted tissue. Next, vacuum source 292 may be operated so as to cause suction to be applied to inner tubular member 77, thereby drawing tissue into outer tubular member 76 through window 89. In addition, motors 151 and 181 may be operated so as to cause inner tubular member 77 simultaneously to rotate and to oscillate back and forth translationally within outer tubular member 76, thereby causing the tissue drawn through window 89 to be cut. The cut tissue may then be suctioned from the patient through inner tubular member 77 by means of the aforementioned suction and, thereafter, collected in container 291. Once the fibroids or other targeted tissues have thus been removed from the patient, vacuum source 292 and motors 151 and 181 may be turned off, device 8 may be withdrawn from the hysteroscope, and the hysteroscope may be withdrawn from the patient. Morcellator assembly 13 may then be detached from drive assembly 15 and disconnected from vacuum source 292. Morcellator assembly 13 may be designed to be a single use device and, if so, may be disposed of after being used on a patient. By contrast, drive assembly 15 may be used on a number of different patients prior to its disposal, with a different morcellator assembly 13 preferably being used with each patient.

It should be noted that, although the above-discussion contemplates inserting device 8 through the working channel of a hysteroscope, one may insert device 8 transcervically into the uterus without the use of a hysteroscope. In such a situation, fluid may be administered transcervically to the uterus by a fluid dispensing device in order to distend the uterus, and, thereafter, observation of the uterus may be accomplished, for example, by ultrasonic imaging using an ultrasonic probe inserted transcervically into the uterus. Such an ultrasonic probe may be separate from device 8 or may be integrated into device 8. Alternatively, imaging of the uterus may be performed by MRI imaging.

Although one may vary one or more of the speed of rotational movement of inner tubular member 77, the frequency of oscillating translational movement of inner tubular member 77, the advance ratio of inner tubular member 77 (i.e., the ratio of the speed at which tubular member 77 oscillates translationally to the speed at which tubular member 77 rotates), and the magnitude of suction provided by vacuum source 292, particularly good results have been achieved under the following conditions: speed of rotation of tubular member 77—at least 1100 rpm, more preferably at least 5000 rpm, even more preferably approximately 6000 rpm; frequency of oscillating translational movement of tubular member 77—at least 1.5 cycles/second, more preferably at least 2.5 cycles/second, even more preferably about 4 cycles/second; advance ratio of preferably less than 0.25, more preferably less than 0.15; and vacuum pressures in the range of 300 to 650 mmHg. Preferably, the above parameters are selected to achieve a rate of tissue removal of at least 1.5 gm/min while outer tubular member 76 has an outer diameter of no greater than about 3.0 mm.

As can be appreciated, as suction is applied to inner tubular member 77, some of the distension fluid located in the uterus may incidentally be withdrawn from the uterus through inner tubular member 77. This loss of distension fluid from the uterus may be undesirable if it interferes with maintenance of the uterus in an adequately distended state. Preferably, system 7 is constructed and operated so that, with a vacuum in excess of 300 mmHg, a volume of no more than about 300 cc/min of fluid is removed. This may involve, for example, applying suction only at specific times, for example, when motors 151 and 181 are actuated.

In general, morcellators may be built in accordance with the present invention to have a lower outside diameter or crossing profile than current commercial products such as the Smith & Nephew Hysteroscopic Morcellator, but at the same time accomplish a higher tissue resection rate. In addition, morcellators in accordance with the present invention may be operated at a significantly higher vacuum while managing total fluid flow within acceptable limits.

For example, the cross sectional area of the aspiration lumen in morcellators in accordance with the present invention will typically be no more than about 12.0 square millimeters, and often nor more than about 10.0 square millimeters. In certain embodiments, a cross sectional area of the aspiration lumen will be no more than about 8.0 millimeters squared, and, for certain applications, the area will be no more than about 7.5 square millimeters.

The tissue resection rate is generally at least about 1.5 gm/min, and often at least about 1.8 gm/min. In certain embodiments, the tissue resection rate is at least about 2.0 gm/min, and, in one embodiment, 2.2 or more gm/min.

In all of the foregoing embodiments, morcellators in accordance with the present invention may be constructed to have a fluid usage of no more than about 350 ml/min. In many embodiments, fluid usage of no more than about 300 ml/min or no more than about 275 ml/min may be constructed.

Applied vacuum to the morcellators of the present invention will generally be in the range of from about 200 to about 800 mm Hg. The morcellator will typically be run at a vacuum of at least about 350 mm Hg, and, often at least about 500 mm Hg.

In one embodiment of the present invention, the cross sectional area of the aspiration lumen was about 7.1 mm$^2$, and yielded a tissue resection rate of about 1.4 gm/min, under vacuum of approximately 600 mm Hg.

In general, procedures accomplished in accordance with the present invention will require no more than about 10 minutes, and preferably, no more than about 8 or 9 minutes of active morcellation. During that time, total fluid (e.g. saline) introduced into the uterus will generally be no greater than about 12 liters, and, preferably no greater than about 10 liters or 8 liters. Distension fluid will preferably be maintained at a low enough pressure and short enough time to keep the total saline intravasation below 2.5 liters.

In a typical procedure in accordance with the present invention, utilizing a morcellator having an outside diameter of 3 mm, the fluid flow rate for aspiration of saline through the morcellator is approximately 260 ml/min (e.g. within the range of from about 240 to about 280 ml/min). Thus, in a ten minute procedure, approximately 2.6 liters of saline is aspirated through the morcellator. In that same procedure, the tissue resection rate is typically in excess of about 2 gm/min.

In a comparative experiment, a device manufactured in accordance with the present invention was compared to the performance of a reciprocating hysteroscopic morcellator, from Smith and Nephew. Over a series of experiments with the predicate device, the vacuum was maintained on average in the 200 to 270 mm Hg range, morcellator speed was approximately 1100 rpm, tissue resection rate was approximately 1.4 gm/min, the fluid flow rate through the morcellator was approximately 247 ml/min, and the outside diameter of the morcellator was 4.0 mm.

The device constructed in accordance with the present invention was operated at a vacuum of 600 mm Hg, a speed of about 6000 rpm, to produce a resection rate of approximately 2.2 gm/min and an aspiration flow rate of about 266 ml/min through the morcellator. The outside diameter of the device was 3 mm.

The morcellator in accordance with the present invention thus produced a significantly higher resection rate, through a smaller outside diameter morcellator, at a roughly comparable flow rate of aspirated saline. In order to increase the resection rate of the predicate device, the vacuum must be significantly increased. For example, when the vacuum pressure in the predicate system was increased to about 670 mm Hg, the tissue cutting improved to 3.5 gm/min but fluid flow rate jumped to 540 ml/min.

One challenge with increased fluid flow rate which is responsive to increased vacuum is that the replacement fluid must be infused into the procedure site at an equal rate. In order to infuse fluid at a sufficient rate to allow the predicate device to function at a higher vacuum, the diameter of the already larger predicate morcellator must be increased. Applicants have determined that the use of the morcellator disclosed herein, with an outside diameter of no more than about 3 mm, in combination with the optic system, allows the dilatation of the cervix be limited to no more than about 5.5 mm. This enables conducting the procedure under a local anesthesia. Increasing the diameter of the morcellator to accommodate the higher infusion rate as well as the already larger outside diameter of the predicate system is believed to cross the anesthesia threshold and appears to impose the need or desirability for conducting the procedure under a general anesthetic. Applicants believe it to be a significant benefit for many patients to be able to avoid general anesthesia.

In another embodiment (not shown), system 7 may further include means for providing an audible indication to the user that motors 151 and/or 181 are being operated. Such an audible indication may be provided by a current detector coupled both to motors 151 and/or 181 and to an audible signal generator, wherein the signal generator may emit a beeping tone or other sound to indicate that motors 151 and/or 181 are in use. Alternatively, an audible indication that motor 151 is in use may be provided by an interference nub provided, for example, on distal tube 168 of gear 162, said interference nub being engageable with a pivotally-mounted flipper arm so that rotation of tube 168 may cause vibration of the flipper arm. Preferably, a sound chamber is provided in such a device to magnify the vibrations of the flipper arm to provide an audible sound. The audible sound will preferably be greater than about 500 Hz in frequency and less than about 10,000 Hz so that its tone may be easily recognized.

In another embodiment (not shown), system 7 may further include a current flow sensor for monitoring the electrical current required to operate motors 151 and/or 181. If a sudden change in current level is detected, for example, in the case of over-torque and under-torque conditions, respectively, a switch linked to the current flow sensor may be opened to shut down motors 151 and 181. The additional safety of controlling motor operation by detecting an unusual operating condition may enhance patient safety by informing the operator that the device was operating in an unsafe mode and should be inspected to ensure that no damage has occurred. The current detection capability will preferably suspend the motor operation should current drop below 10% or exceed 150% of its steady state operating value.

In another embodiment (not shown), system 7 may further include a timer that may be linked to the operation of motors 151 and/or 181 to provide a running total of the operating time of the tissue removal device. The timer may be reset each time drive assembly 15 is restarted to provide the running time for the current operation. By providing the operating time, the device may inform the user of the elapsed procedure time, thereby enabling the user to make judgments on the safety of continuing the procedure. This information may be valuable since, in many procedures, anesthesia or fluid intravasation limits are directly related to the operating time. Thus, recognition of the elapsed time will enable the user to terminate the procedure should the appropriate time limitation be reached.

In another embodiment (not shown), sensor 299 may be replaced with a flow sensor, such as an ultrasonic or laser transducer that can detect a change in the flow rate of fluid through the evacuation tube 293, whereby a sudden drop in fluid flow results in a change in signal properties from the transducer. Alternatively, a sensor may be used that comprises a scale that can detect the change in the weight of matter collected in specimen container 291, with a plateauing of weight indicating that flow has stopped. The presence of a clog may be indicated via an alarm, which may be an audible alarm and/or a visible alarm, e.g., a flashing LED. The audible alarm may comprise a chamber in fluid communication with vacuum source 292 wherein a change in pressure level or flow creates a pressure gradient strong enough to create a whistle or audible sound through the chamber.

In another embodiment (not shown), device 8 may be modified so that outer tubular member 76 may be angularly adjustable about its longitudinal axis relative to housing 21. This may be accomplished by fixedly mounting outer tubular member 76 on a hub that is rotatably mounted on housing 21. In this manner, outer tubular member 76 may be angularly adjusted so that resection window 89 may be positioned at a desired angular position. Preferably, means are provided to prevent the rotatable hub from freely spinning while the device is being used to resect tissue.

It should be noted that, although resection window 89 of outer tubular member 76 and distal end 92 of inner tubular member 77 are described above as possessing certain dimensions and/or geometries, the present invention is not limited to such dimensions and geometries and may encompass alternate dimensions and/or geometries. For example, the geometry of resection window 89 may be varied from a straight perpendicular edge to a more complicated parabolic profile. Two underlying principles guide the selection of the geometry. First, structural loading considerations will favor the use of gussets in the corners of the window to alleviate the stress concentrations observed at sharp corners under operating loads. Second, the highest bite efficiency will be obtained with the largest possible window opening. (As used herein, the term "bite efficiency" refers to the amount of material or tissue that can be removed with each stroke of a cutting edge.) Although these two considerations do confound each other, it is possible to define an optimum geometry. The guiding formulas for beam deflection and stress are non-linear in nature and thusly a non-linear geometry profile will reduce the deflections and stresses to acceptable levels. The non-linear profile produced by a parabolic shape will satisfy this constraint. A controlling parameter for the shape of a parabolic curve is the rho value. (As used herein, the term "rho" refers to the ratio of conic section lengths used to define the curvature of a parabolic shape.) The optimum value for rho for this application is preferably greater than 0.414, which defines a circle, and less than 1, which describes a perpendicular straight edge.

Radial ends of the window tend to engage subject tissues whose growth produces cylindrical or spherical entities far more effectively than conventional squared ends. The radial ends enhance the device's ability to create a vacuum seal against the tissue that enables a larger specimen to be drawn into the cutting window. The resulting larger specimens improve the bite efficiency whereby the largest possible specimens are captured each time the inner cutter is activated. High bite efficiency translates into reduced procedure time and the potential for complications associated with anesthesia, intravasation, etc.

The resection window preferably extends over approximately 30% to 80% of the circumference of the outer tube, i.e., "the open ratio." The open ratio will define combinations of inner tubes and outer tubes whereby the tissue specimen size is comparable to that of the tube opening. By maximizing the specimen size, the bite efficiency may be optimized whereby the largest possible specimens are captured each time the inner cutter is activated. High bite efficiency translates into reduced procedure time and the potential for complications associated with anesthesia, intravsation, etc.

Referring now to FIGS. 4(a) through 4(e), there are shown various fragmentary, perspective views of alternate embodiments to outer tubular member 76, the alternate outer tubular members being represented generally by reference numerals 301, 302, 303, 304 and 305, respectively. Members 301, 302, 303, 304 and 305 are similar in most respects to outer tubular member 76 and may be used in place thereof, the principal differences among the various members being in the size, shape and/or placement of their respective windows. More specifically, member 301 (FIG. 4(a)) may comprise a window 307 having a parabolic shape. Members 302 (FIG. 4(b)) and 303 (FIG. 4(c)) may comprise rectangularly-shaped windows 308 and 309, respectively, with window 309 differing from window 308 in that window 309 has a greater open ratio than window 308 and in that window 308 is positioned closer to distal end 302-1 of member 302 than window 309 is to distal end 303-1 of member 303. Member 304 (FIG. 4(d)) may comprise a window 310 having a sloped proximal end 310-1 and a jagged distal end 310-2. Member 305 (FIG. 4(e)) may comprise a window 311 having a straight proximal end 311-1 and a distal end 311-2 having a proximally-directed point 312.

Referring now to FIGS. 5(a) through 5(e), there are shown various fragmentary, perspective views of alternate embodiments to inner tubular member 77, the alternate inner tubular members being represented generally by reference numerals 321, 322, 323, 324 and 325, respectively. Members 321, 322, 323, 324 and 325 are similar in most respects to inner tubular member 77 and may be used in place thereof, the principal difference among the various members being in the shape of their respective distal ends. More specifically, member 321 (FIG. 5(a)) may comprise a distal end 326 having a rectangular shape with a 30 degree external bevel. Member 322 (FIG. 5(b)) may comprise a distal end 327 having a rectangular shape with an internal bevel. Member 323 (FIG. 5(c)) may comprise a distal end 328 having an angled shape with an external bevel. Member 324 (FIG. 5(d)) may comprise a jagged distal end 329 having eight teeth. Member 325 (FIG. 5(e)) may comprise a jagged distal end 330 having six teeth.

Referring now to FIG. 5(f), there is shown a fragmentary perspective view, shown in section, of another alternate embodiment to inner tubular member 77, said alternate inner tubular member being represented by reference numeral 331. Inner tubular member 331 may be similar in most respects to inner tubular member 77, with inner tubular member 331 differing principally from inner tubular member 77 in that inner tubular member 331 may comprise a proximal portion 333 of comparatively greater inner diameter and a distal portion 335 of comparatively lesser inner diameter. The expanded inner diameter of proximal portion 333 may permit matter to be drawn proximally through inner tubular member 331 with greater ease, thereby reducing the risk that inner tubular member 331 may become clogged.

Referring now to FIGS. 6(a) and 6(b), there are shown fragmentary longitudinal section views of another embodiment of a tissue removal device constructed according to the teachings of the present invention, said tissue removal device being represented by reference numeral 341.

Device 341 may be similar in most respects to device 8, device 341 differing principally from device 8 in that device 341 may comprise an inner tubular member 342, an outer tubular member 343, and a plug 344, instead of outer tubular member 76 and inner tubular member 77. Inner tubular member 342 may be identical to inner tubular member 77. Outer tubular member 343 may be similar in most respects to outer tubular member 76, with outer tubular member 343 differing principally from outer tubular member 76 in that outer tubular member 343 may comprise an open distal end 345. Plug 344, which may be fixedly mounted within distal end 345 of outer tubular member 343, may be shaped to include a mandrel 346. Mandrel 346 may extend proximally within lumen 347 of outer tubular member 343, terminating distally prior to window 348. (Window 348 may have the same dimensions and geometry as window 89 of outer tubular member 76.) Mandrel 346 may be dimensioned so that, when inner tubular member 342 is moved distally, distal end 349 of inner tubular member 342 may slide past the side wall 346-1 of mandrel 346, thereby shearing tissue located therebetween. In addition, because distal end 349 of inner tubular member 342 slides past an extended length of mandrel 346, mandrel 346 serves to push tissue down the lumen of inner tubular member 342 to ensure that the tissue is severed and that vacuum pressure can draw the tissue through inner tubular member 342. Furthermore, mandrel 346 may be shaped to include a longitudinal bore 350 aligned with the lumen 342-1 of inner tubular member 342. Bore 350 may serve to permit fluid to enter inner tubular member 342—even when inner tubular member 342 is in its most distal position. In this manner, tissue and other matter may be moved proximally through inner tubular member 342 by such fluid flow, thereby preventing inner tubular member 342 from becoming clogged. By minimizing clogging, the procedure time and the potential for complications associated with anesthesia, intravasation, etc. may be minimized.

Figure 7B:
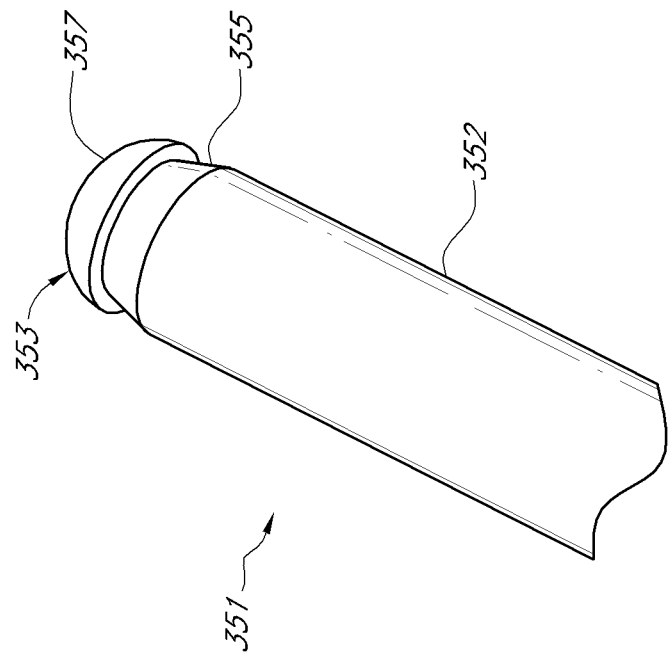
FIGS. 7(a) and 7(b) are fragmentary perspective views of a further embodiment of a tissue removal device constructed according to the teachings of the present invention.
Figure 7A:
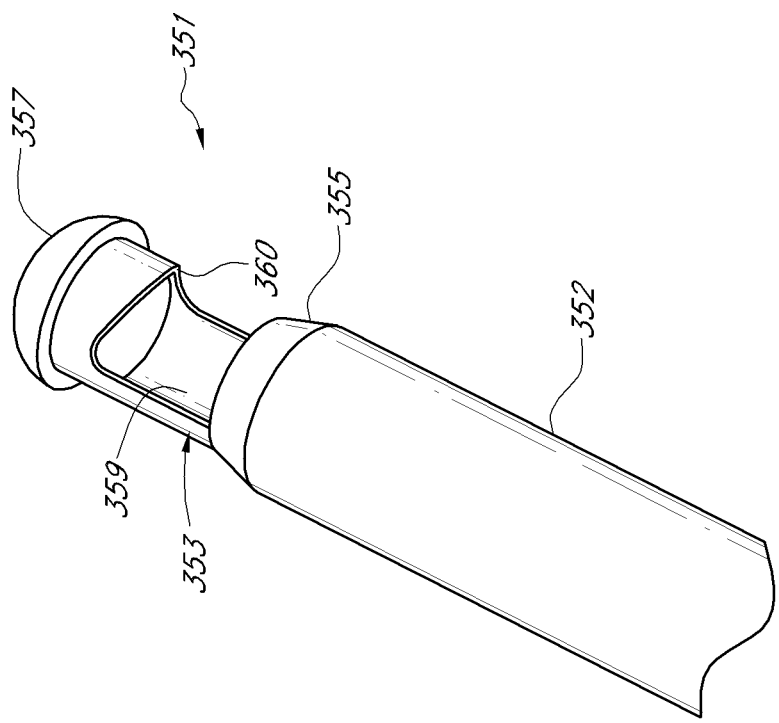

Referring now to FIGS. 7(a) and 7(b), there are shown fragmentary perspective views of a further embodiment of a tissue removal device constructed according to the teachings of the present invention, said tissue removal device being represented by reference numeral 351.

Device 351 may be similar in most respects to device 8, device 351 differing principally from device 8 in that device 351 may comprise an outer tubular member 352 and an inner tubular member 353. Outer tubular member 352, which may be similar in certain respects to outer tubular member 76 of device 8, may comprise a distal end 355 having an external bevel. Inner tubular member 353, which may be similar in certain respects to inner tubular member 77, may comprise a closed distal end 357 having a dome-shape and a resection window 359 spaced proximally a short distance in front of distal end 357. Window 359 may be shaped to comprise a sharpened distal end 360. In use, outer tubular member 352 may be stationary, and inner tubular member 353 may rotate relative to the longitudinal axis of outer tubular member 352 and, at the same time, may oscillate translationally in an independently controllable fashion between a distal position in which window 359 is positioned distally beyond outer tubular member 352 and a proximal position in which window 359 is positioned within outer tubular member 352. (In another embodiment, inner tubular member 353 may oscillate translationally without rotating.) As can be appreciated, when window 359 is positioned distally relative to outer tubular member 352, tissue may enter window 359. Thereafter, as window 359 may be drawn proximally into outer tubular member 352, the tissue that has entered window 359 may be cut between distal end 360 of window 359 and distal end 355 of outer tubular member 352. By shearing the tissue on the proximal stroke of inner tubular member 353, the tissue may be pushed down the lumen of inner tubular member 353 in the same direction that suction is being applied. The additional mechanical force provided by this cutting action may reduce the risk of clogging inner tubular member 353. Such a reduction in the risk of clogging may enhance the likelihood that the procedure may be completed as planned and reduce the need for follow-up procedures or delayed or canceled procedures.

Referring now to FIGS. 8(a) and 8(b), there are shown perspective and enlarged fragmentary perspective views, respectively, of a further embodiment of a tissue removal device constructed according to the teachings of the present invention, said tissue removal device being represented generally by reference numeral 381.

Tissue removal device 381 may be similar in many respects to device 8. However, one notable difference between the two devices may be that, whereas device 8 may comprise a cutting mechanism including outer tubular member 76 and inner tubular member 77, both of which may be straight, device 381 may comprise a cutting mechanism including an outer tubular member 383 and an inner tubular member 385, wherein outer tubular member 383 may include a bent region 387 and inner tubular member 385 may contain a corresponding compliant section 389. Outer tubular member 383 may be formed into the desired configuration using conventional tooling to provide a fixed bent angle. Alternatively, one may furnish the user with a forming tool that allows the user to form the outer tubular member into any desired angle to ease delivery of the device. The inner tubular member 385 may include a flexible drive shaft 391 located in the bent region. Flexible drive shaft 391 may be directed around the bent region 387 to transmit torque and translational motion. Such a configuration may enable device 381 to more closely mimic the angles of the cervix and uterus and, as a result, make introduction easier. The angled tip may also make direction of the cutting tip easier to direct, especially when trying to access the fallopian regions of the uterus. The tip may be rotated by rotating the entire device, or the device may be provided with a rotation knob 392 to permit the cutting mechanism to be rotated relative to the drive assembly. As can be appreciated, any reduction in the time required to direct the device towards the target pathology may reduce overall procedure duration and increase the probability of successful removal of the entire tissue specimen.

Referring now to FIG. 9, there is shown a fragmentary perspective view of a further embodiment of a tissue removal device constructed according to the teachings of the present invention, said tissue removal device being represented generally by reference numeral 401.

Tissue removal device 401 may be similar in many respects to device 8. However, one notable difference between the two devices may be that, whereas device 8 may comprise a cutting mechanism including outer tubular member 76 and inner tubular member 77, both of which may be straight and axially inflexible, device 401 may comprise a cutting mechanism including an outer tube having some axial flexibility and an inner tube having some axial flexibility, the inner tube being independently rotatable and translationally oscillatable within the outer tube. The outer tube may comprise an axially flexible tubular shaft 403 and a rigid tubular tip 405, tip 405 being fixed to the distal end of shaft 403. (Tip 405 may have an open distal end, which may be sealed with a plug 406.) The inner tube may comprise an axially flexible tubular shaft 407 and a rigid tubular tip 409, tip 409 being fixed to the distal end of shaft 407. Tubular tip 405 may have a shape similar to the distal portion of outer tubular member 76 so that shaft 403 and tip 405 may collectively have a shape corresponding generally to that of outer tubular member 76. Tubular tip 409 may have a shape similar to the distal end of inner tubular member 77 so that shaft 407 and tip 409 may collectively have a shape corresponding generally to that of inner tubular member 77. Each of shaft 403 and shaft 407 may be made of a suitable metal, such as Nitinol (nickel-titanium alloy) or Microflex hypo tubing, or may be made of a suitable polymeric material, such as TEFLON® polytetrafluoroethylene, polyamide, polyimide, polyetheretherketones etc.

Because of its flexible construction, device 401 may provide a cutting mechanism that more closely mimics the access angles of the body in places like the bladder, cervix and uterus. The ability to flex may reduce introduction forces and may reduce the probability of a perforation. In addition, any reduction in the time required to direct the cutting mechanism towards the target pathology may reduce overall procedure duration and increase the probability of successful removal of the entire targeted tissue.

Referring now to FIG. 10, there is shown a fragmentary perspective view of a further embodiment of a tissue removal device constructed according to the teachings of the present invention, said tissue removal device being represented generally by reference numeral 421. Device 421 may be similar in many respects to device 401, device 421 differing principally from device 401 in that device 421 may additionally comprise a pair of pull wires 422 and 423. Pull wires 422 and 423, which may be used to flex shaft 403 at a desired angle, may be fixed at their respective distal ends to shaft 403 and may be fixed at their respective proximal ends to a spring-torsioned, rotatable hub (not shown). Because of its own flexibility, shaft 407 will bend to accommodate the deflection of shaft 403.

Referring now to FIG. 11, there is shown a fragmentary perspective view, broken away in part, of a further embodiment of a tissue removal device constructed according to the teachings of the present invention, said tissue removal device being represented generally by reference numeral 430.

Device 430 may be similar in many respects to device 8, device 430 differing principally from device 8 in that device 430 may include, instead of outer tubular member 76 and inner tubular member 77, an inner tubular member 431, an outer tubular member 432, and a plug 433. Inner tubular member 431 may be identical to inner tubular member 331. Outer tubular member 432 may be similar to outer tubular member 76, except that outer tubular member 432 may include an open distal end. Plug 433, which may be a solid member fixed to outer tubular member 432, may include a proximal portion 435 of cylindrical shape snugly disposed within the lumen of outer tubular member 432 and a distal portion 437 of rounded shape extending distally from the distal end of outer tubular member 432. Proximal portion 435 may have a proximal surface 439 that is positioned to contact the distal end of inner tubular member 431 when inner tubular member 431 completes its distal stroke. Inner tubular member 431 may oscillate translationally or may rotate and oscillate translationally in an independently controllable fashion. In use, as inner tubular member 431 moves distally, the distal end of inner tubular member 431 engages tissue that may have entered window 440. When inner tubular member 431 reaches the end of its distal stroke, the distal end of inner tubular member 431 strikes proximal surface 439 of plug 433. This striking or chopping action of the distal end of inner tubular member 431 against proximal surface 439 creates a shear plane that results in tissue fibers and tags not being left behind when inner tubular member 431 thereafter moves through its proximal stroke. In this manner, the distal end of inner tubular member 431 and proximal surface 439 of plug 433 ensure that a clean cut is achieved. As a result, the risk for clogging may be minimized and the need for multiple strokes to cut the tissue may be reduced. Both of these benefits may improve the cutting efficiency, which, in turn, may greatly enhance the likelihood that the procedure may be completed as planned and may reduce the need for follow-up procedures or delayed or canceled procedures.

Referring now to FIG. 12, there is shown a fragmentary, perspective view of a further embodiment of a tissue removal device constructed according to the teachings of the present invention, said tissue removal device being represented by reference numeral 451.

Device 451 may be similar in many respects to device 430, with device 451 differing principally from device 430 in that device 451 may comprise an outer tubular member 453 and an electrocautery tip 455, instead of outer tubular member 432 and plug 433. Outer tubular member 453 may be similar to outer tubular member 432, except that outer tubular member 453 may be further provided with electrical leads 457 running through side wall 459 to couple tip 455 to a power source (not shown). Tip 455, which may be heated by current passing through leads 457, may be used to cauterize small arterial vessel bleeding that may incidentally occur while using device 451 to resect tissue. By minimizing such bleeding, tip 455 reduces the amount of blood that may fill the uterus and that may create visualization or blood loss concerns.

Referring now to FIGS. 13(a) and 13(b), there are shown fragmentary perspective and fragmentary side views, respectively, of a further embodiment of a tissue removal device constructed according to the teachings of the present invention, said tissue removal device being represented by reference numeral 471.

Device 471 may be similar in certain respects to device 8, with device 471 differing principally from device 8 in that device 471 may comprise a tubular member 473, instead of the combination of outer tubular member 76 and inner tubular member 77. Tubular member 473 may be similar in certain respects to outer tubular member 76, with tubular member 473 differing from outer tubular member 76 in that tubular member 473 may comprise a longitudinally-extending lumen 475 provided in a side wall 477. The proximal end (not shown) of lumen 475 may be optically coupled to the output end of a laser (not shown) so that laser light 479 may be transmitted distally across a resection window 480 provided in side wall 477, laser light 479 being capable of tissue resection. The proximal end (not shown) of tubular member 473 may be coupled to vacuum source 292 so that suction may be used to draw tissue through window 480, where it may be cut by laser light 479, and then to move the cut tissue proximally through tubular member 473.

Referring now to FIG. 14, there is shown a fragmentary perspective view of a further embodiment of a tissue removal device constructed according to the teachings of the present invention, the tissue removal device being represented generally by reference numeral 490.

Device 490 may be similar in most respects to device 471, with device 490 differing from device 471 in that device 490 may include a lumen 492 having a horseshoe-shape in transverse cross-section and in that device 490 may further include an optic fiber 494 positioned within lumen 492 for transmitting the laser light. Optic fiber 494 may be adapted to move back and forth between ends 496 and 498 of lumen 492 to provide a knife-like cutting action for tissue within window 497. Optic fiber 494 may be moved along the desired cutting arc within lumen 492 by coupling the proximal end (not shown) of fiber 494 to an articulating rotating cylinder or tube.

Figure 15B:
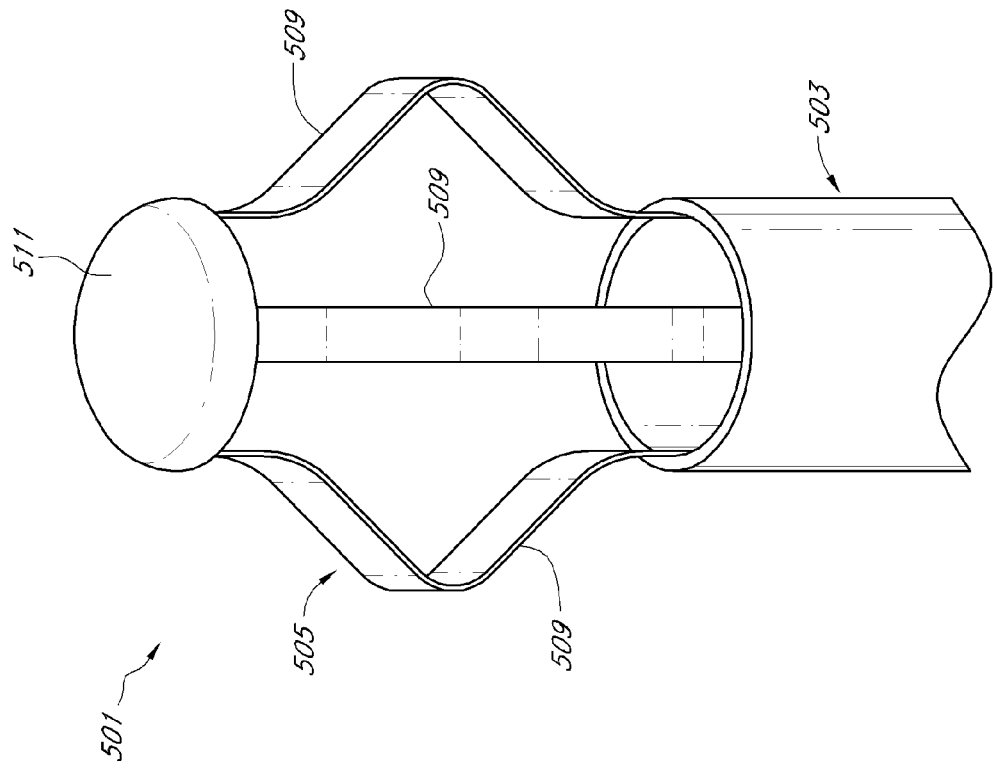
FIGS. 15(a) and 15(b) are fragmentary perspective views of a further embodiment of a tissue removal device constructed according to the teachings of the present invention, the tissue removal device being shown with its cutting member in its proximal and distal positions, respectively.
Figure 15A:
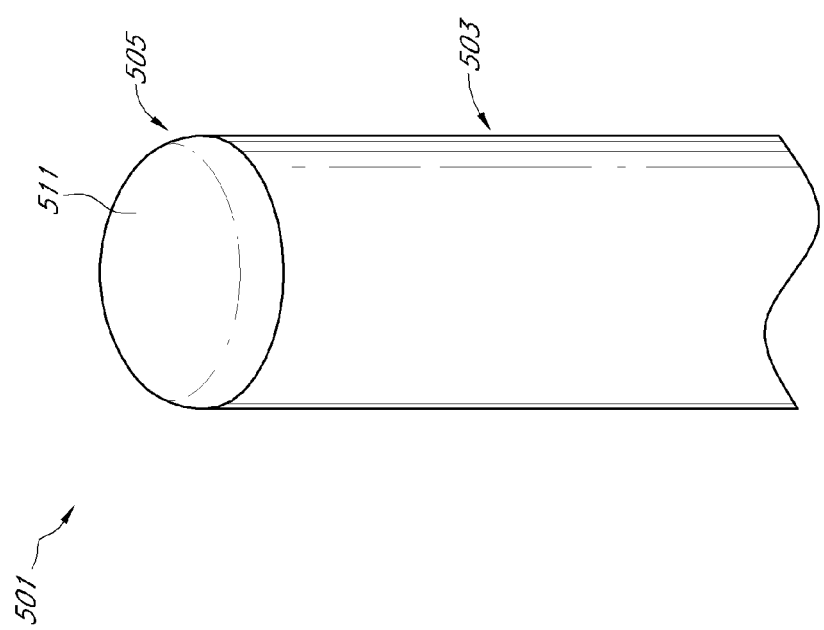

Referring now to FIGS. 15(a) and 15(b), there are shown fragmentary perspective views of a further embodiment of a tissue removal device constructed according to the teachings of the present invention, the tissue removal device being represented generally by reference numeral 501.

Device 501 may be similar in certain respects to device 351, with device 501 differing principally from device 351 in that device 501 may comprise the combination of an outer tubular member 503 and an inner cutting member 505, instead of the combination of outer tubular member 352 and inner tubular member 353. Outer tubular member 503 may be similar in most respects to outer tubular member 352, with outer tubular member 503 differing principally from outer tubular member 352 in that outer tubular member 503 may include a distal end 507 that is straight, as opposed to beveled. Inner cutting member 505 may comprise a plurality of outwardly biasing blades 509 fixed at their respective distal ends to a cap 511 so that inner cutting member 505 assumes a whisk-like structure when extended distally relative to outer member 503. Blades 509 and cap 511 may include an electrically-conductive material so that, by electrically coupling the proximal ends (not shown) of blades 509 to a suitable electrical power source (not shown), blades 509 and/or cap 511 may be used for electrocautery. (Such an arrangement may be made to be either by monopolar or bipolar.) In use, device 501 may be delivered transcervically to the uterus, preferably through the working channel of a hysteroscope, with inner cutting member 505 in its proximal position, i.e., with cap 511 against distal end 507 of outer tubular member 503 (FIG. 15(a)). While in this state, electricity may be transmitted to cap 511 so that cap 511 may be used to burn the tissue of interest. Alternatively, inner cutting member 505 may be moved distally relative to outer tubular member 503 to its extended position (FIG. 15(b)). While in this state, inner cutting member 505 may be rotated about its longitudinal axis so that blades 509 may cut tissue. Simultaneously, electricity may be transmitted to blades 509 and cap 511 for cauterization. Suction may be applied to the proximal end (not shown) of outer tubular member 503 to draw tissue into contact with blades 509 and to move resected tissue proximally through tubular member 503.

Figure 16B:
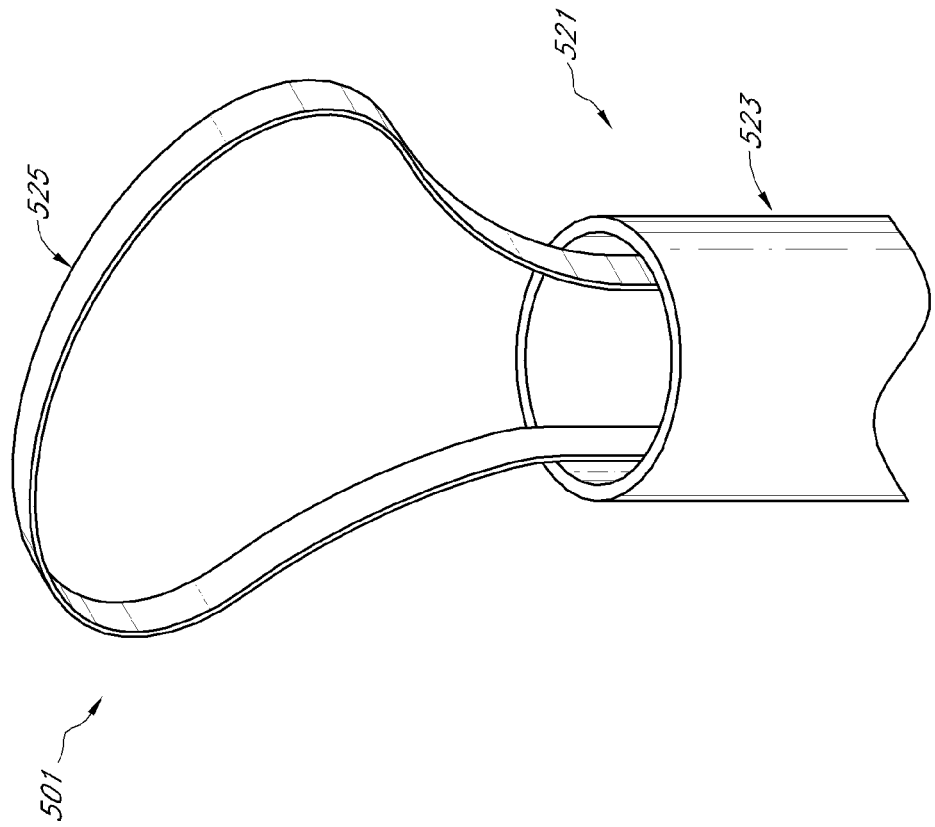
FIGS. 16(a) and 16(b) are fragmentary perspective views of a further embodiment of a tissue removal device constructed according to the teachings of the present invention, the tissue removal device being shown with its movable member in its proximal and distal positions, respectively.
Figure 16A:
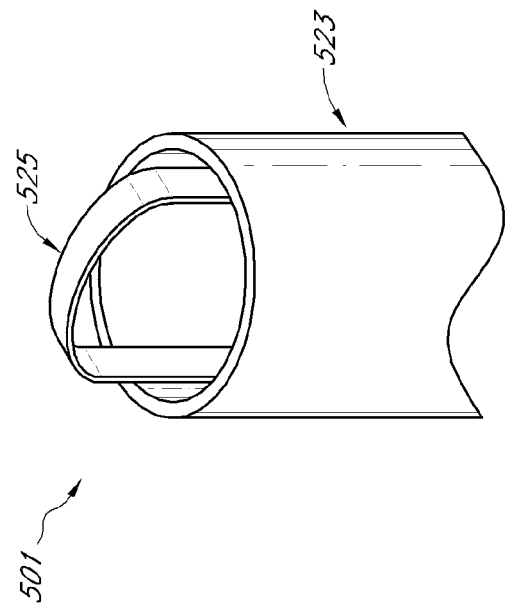

Referring now to FIGS. 16(a) and 16(b), there are shown fragmentary perspective views of a further embodiment of a tissue removal device constructed according to the teachings of the present invention, the tissue removal device being represented generally by reference numeral 521.

Device 521 may be similar in certain respects to device 501, with device 521 differing principally from device 501 in that device 521 may comprise the combination of a tubular member 523 and an outwardly-biasing loop 525 slidably mounted in tubular member 523, instead of the combination of outer tubular member 503 and inner cutting member 505. In use, device 521 may be delivered transcervically to the uterus, preferably through the working channel of a hysteroscope, with loop 525 in its proximal or retracted position within tubular member 523 (FIG. 16(a)). Next, loop 525 may be moved distally relative to tubular member 523, thereby allowing loop 525 to expand (FIG. 16(b)). With loop 525 thus expanded, loop 525 may be placed around the tissue of interest. Loop 525 may then be withdrawn into tubular member 523, with loop 525 drawing the surrounded tissue into tubular member 523. (If desired, loop 525 may also be made to be rotatable about the longitudinal axis of tubular member 523.) As the tissue is drawn past the distal end 527 of tubular member 523 by loop 525, the tissue is severed. Suction may be applied to the proximal end (not shown) of tubular member 523 to draw tissue into loop 525 and to move resected tissue proximally through tubular member 523.

Loop 525 may include electrically-conductive material and may be electrically coupled to an electrical power source for use in electrocautery. In another embodiment (not shown), device 521 may be modified to include a second loop, the two loops having opposite polarities to provide a bipolar electrocautery device. An advantage of a bipolar device, as opposed to a monopolar device, is that a bipolar device may be used with an electrically-conductive distension fluid, such as saline.

Referring now to FIG. 17, there is shown a fragmentary perspective view of a further embodiment of a tissue removal device constructed according to the teachings of the present invention, the tissue removal device being represented generally by reference numeral 541.

Device 541 may be similar in certain respects to device 521, with device 541 differing principally from device 521 in that device 541 may comprise the combination of a tubular member 543 and a grappling assembly 545 slidably mounted in tubular member 543, instead of the combination of tubular member 523 and loop 525. Grappling assembly 545 may comprise a rotatable shaft 547, a cap 549 mounted on the distal end of shaft 547, a plurality of fingers 551 extending downwardly at an angle from cap 549, an auger 553 coaxially inserted over and mechanically coupled to shaft 547, and a plurality of fingers 555 extending upwardly at an angle from auger 553. In use, device 541 may be delivered transcervically to the uterus, preferably through the working channel of a hysteroscope, with assembly 545 in its proximal or retracted position within tubular member 543, i.e., with cap 549 against the distal end 544 of tubular member 543. Next, assembly 545 may be moved distally relative to tubular member 543, and shaft 547 may be rotated. Fingers 551 and 555 may grab the tissue of interest, and assembly 545 may be retracted into tubular member 543. As the tissue is drawn past the distal end 544 of tubular member 543, the tissue is severed. Suction may be applied to the proximal end (not shown) of tubular member 543 to draw tissue towards fingers 551 and 555 and to move resected tissue proximally through tubular member 543. In addition, auger 553 may draw the resected tissue proximally through tubular member 543.

Figure 18B:
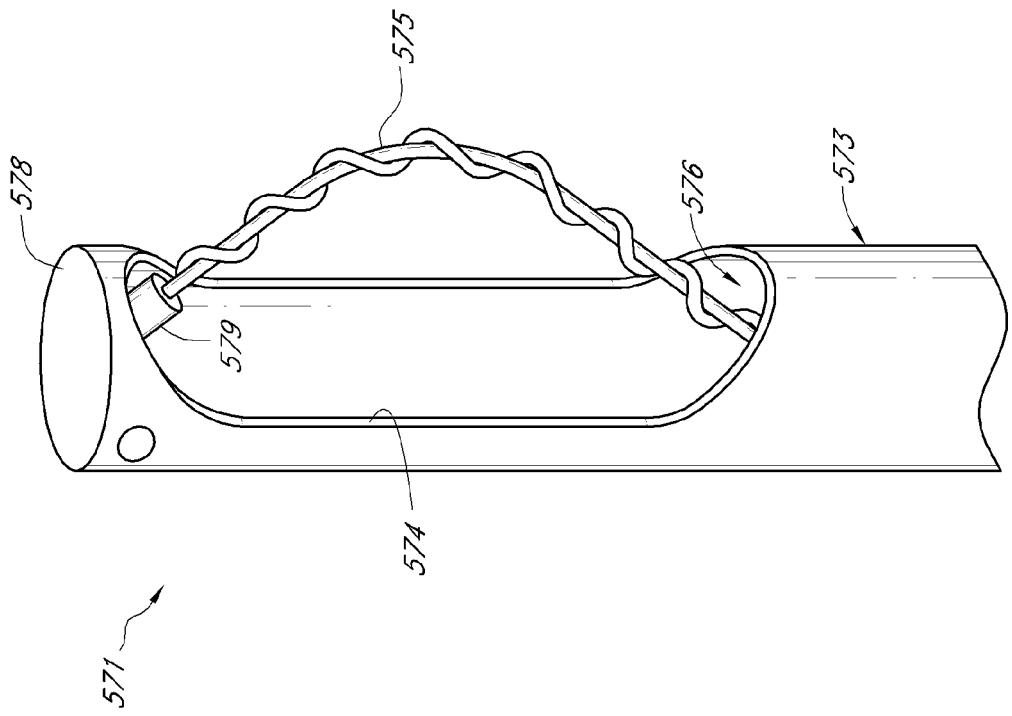
FIGS. 18(a) and 18(b) are fragmentary perspective views of a further embodiment of a tissue removal device constructed according to the teachings of the present invention, the tissue removal device being shown with its cutting element in its retracted and extended positions, respectively.
Figure 18A:
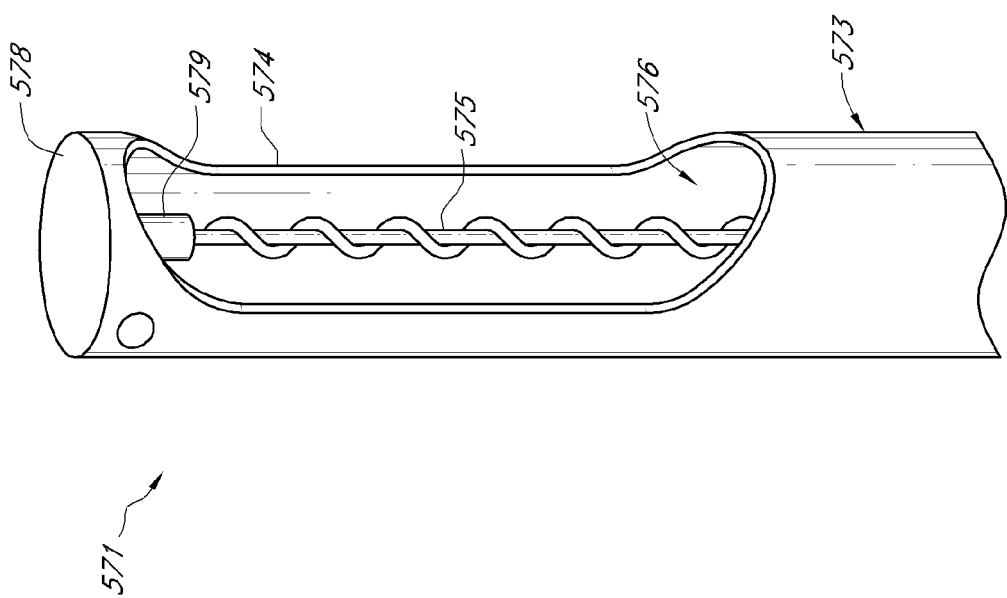

Referring now to FIGS. 18(a) and 18(b), there are shown fragmentary perspective views, respectively, of a further embodiment of a tissue removal device constructed according to the teachings of the present invention, said tissue removal device being represented by reference numeral 571.

Device 571 may be similar in certain respects to device 8, with device 571 differing principally from device 8 in that device 571 may comprise the combination of a tubular member 573 and a spiral cable 575, instead of the combination of outer tubular member 76 and inner tubular member 77. Tubular member 573, which may be similar to outer tubular member 76, may comprise a resection window 574 and a longitudinal lumen 576. Cable 575 may be disposed within lumen 576 of tubular member 573, with the distal end 579 of cable 575 fixed to the interior surface of the distal end 578 of tubular member 573. In use, device 571 may be delivered transcervically to the uterus, preferably through the working channel of a hysteroscope, with cable 575 pulled proximally to remain within lumen 576 (FIG. 18(*a*)). Next, the proximal end (not shown) of cable 575 may be moved distally, causing a portion of cable 575 to buckle outwardly through window 574. At the same time, cable 575 may be rotated about its longitudinal axis (FIG. 18(*b*)) to provide a cutting action. Suction may be applied to the proximal end (not shown) of tubular member 573 to draw tissue towards cable 575 and to move resected tissue proximally through tubular member 573.

Figure 19B:
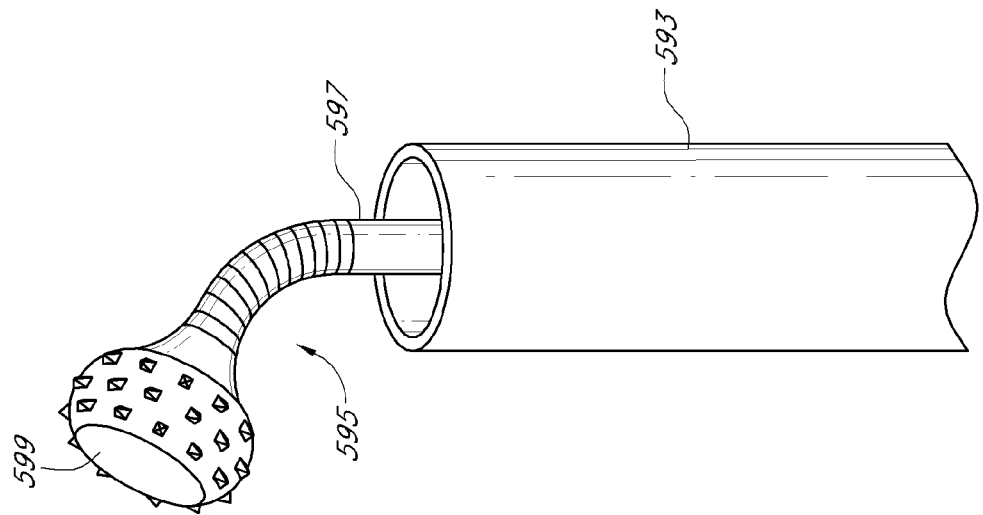
FIGS. 19(a) and 19(b) are fragmentary perspective views of a further embodiment of a tissue removal device constructed according to the teachings of the present invention, the tissue removal device being shown with its cutting element in its retracted and extended positions, respectively.
Figure 19A:
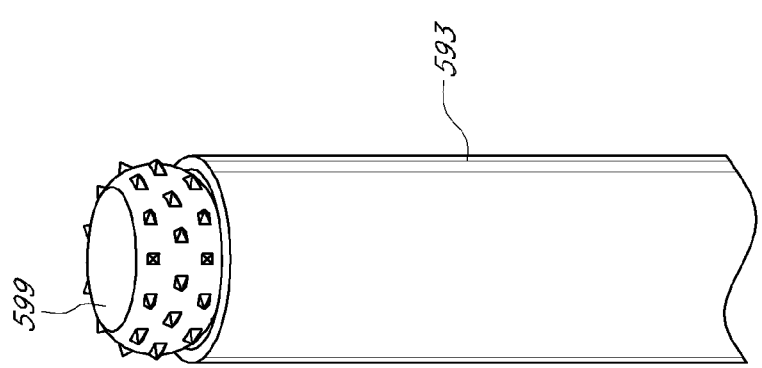

Referring now to FIGS. 19(*a*) and 19(*b*), there are shown fragmentary perspective views of a further embodiment of a tissue removal device constructed according to the teachings of the present invention, the tissue removal device being represented generally by reference numeral 591.

Device 591 may be similar in certain respects to device 521, with device 591 differing principally from device 521 in that device 591 may comprise the combination of a tubular member 593 and a cutter 595 slidably mounted in tubular member 593, instead of the combination of tubular member 523 and loop 525. Cutter 595, which may resemble a mace, may comprise a flexible shaft 597 and a spiked head 599. Head 599 may be coated with a material like tungsten carbide. In use, device 591 may be delivered transcervically to the uterus, preferably through the working channel of a hysteroscope, with head 599 in its proximal or retracted position against tubular member 593 (FIG. 19(*a*)). Next, shaft 597 may be moved distally in order to position head 599 away from tubular member 593, and shaft 597 may be rotated, causing head 599 to swing around in a circle (FIG. 19(*b*)) and cutting the tissue in contact therewith. (By adjusting the distance head 599 is spaced from tubular member 593, one may adjust the diameter of the circle in which head 599 moves.) Suction may be applied to the proximal end (not shown) of tubular member 593 to draw tissue into contact with head 599 and to move resected tissue proximally through tubular member 593.

Referring now to FIG. 20, there is shown a fragmentary perspective view of a further embodiment of a tissue removal device constructed according to the teachings of the present invention, the tissue removal device being represented generally by reference numeral 611.

Device 611 may be similar in certain respects to device 591, with device 611 differing principally from device 591 in that device 611 may comprise the combination of a tubular member 613 and a harpoon 615 slidably mounted in tubular member 613, instead of the combination of tubular member 593 and mace 595. Tubular member 613 may be similar to tubular member 593, except that tubular member 613 may comprise a serrated distal end 614. Harpoon 615 may comprise a rigid shaft 617 and a pointed head 619 disposed at the distal end of shaft 617. In use, device 611 may be delivered transcervically to the uterus, preferably through the working channel of a hysteroscope, with head 619 in its proximal or retracted position within tubular member 613. Next, shaft 617 may be moved distally until head 619 is inserted into the tissue T of interest. Head 619, together with the tissue attached thereto, may then be drawn back towards tubular member 613, whereby the tissue may be cut as it comes into contact with serrated distal end 614. Suction may be applied to the proximal end (not shown) of tubular member 613 to draw tissue into contact with head 619 and to move resected tissue proximally through tubular member 613.

Referring now to FIGS. 21(*a*) and 21(*b*), there are shown fragmentary perspective views of a further embodiment of a tissue removal device constructed according to the teachings of the present invention, the tissue removal device being represented generally by reference numeral 631.

Device 631 may be similar in certain respects to device 541, with device 631 differing principally from device 541 in that device 631 may comprise the combination of tubular member 633 and a grating assembly 635, instead of tubular member 543 and grappling assembly 545. Grating assembly 635 may comprise a pair of parallel shafts 637 and 639, the distal ends of which are fixed to a rounded cap 641. A grater 643 is hingedly mounted on shaft 637, and a grater 645 is hingedly mounted on shaft 639. In use, device 631 may be delivered transcervically to the uterus, preferably through the working channel of a hysteroscope, with cap 641 in its proximal position against the distal end 634 of tubular member 633. Next, assembly 635 may be moved distally relative to tubular member 633 (FIG. 21(*a*)). Next, assembly 635 may be rotated about its longitudinal axis, causing graters 643 and 645 to swing outwardly (FIG. 21(*b*)) and to grate the tissue of interest. Suction may be applied to the proximal end (not shown) of tubular member 633 to draw tissue towards graters 643 and 645 and to move resected tissue proximally through tubular member 633. When the procedure is complete, graters 643 and 645 may be swung back, and assembly 635 may be moved back to its proximal position. Device 631 may then be withdrawn from the patient.

Referring now to FIGS. 22(*a*) and 22(*b*), there are shown fragmentary perspective views of a further embodiment of a tissue removal device constructed according to the teachings of the present invention, the tissue removal device being represented generally by reference numeral 651.

Device 651 may be a generally tubular structure comprising a stationary jaw 653 and a movable jaw 655, movable jaw 655 being hingedly coupled to stationary 653 and being movable by means of a shaft 657. In use, device 651 may be delivered transcervically to the uterus, preferably through the working channel of a hysteroscope, with movable jaw 655 closed against stationary jaw 653 (FIG. 22(*a*)). Next, movable jaw 655 may be pivoted away from stationary jaw 653 to allow tissue to enter therebetween (FIG. 22(*b*)). Next, movable jaw 655 may be pivoted back towards stationary jaw 653 to cut the tissue positioned therebetween. Suction may be applied to the proximal end (not shown) of device 651 to draw tissue between jaws 653 and 655 and to move resected tissue proximally through device 651.

Referring now to FIG. 23, there is shown a fragmentary perspective view of a further embodiment of a tissue removal device constructed according to the teachings of the present invention, the tissue removal device being represented generally by reference numeral 671.

Device 671 may be similar in many respects to device 651, with device 671 differing principally from device 651 in that device 671 may comprise two movable jaws 673 and 675, instead of stationary jaw 653 and movable jaw 655, and in that device 671 may further comprise an auger 677 for use in moving tissue proximally within device 671.

Figure 24B:
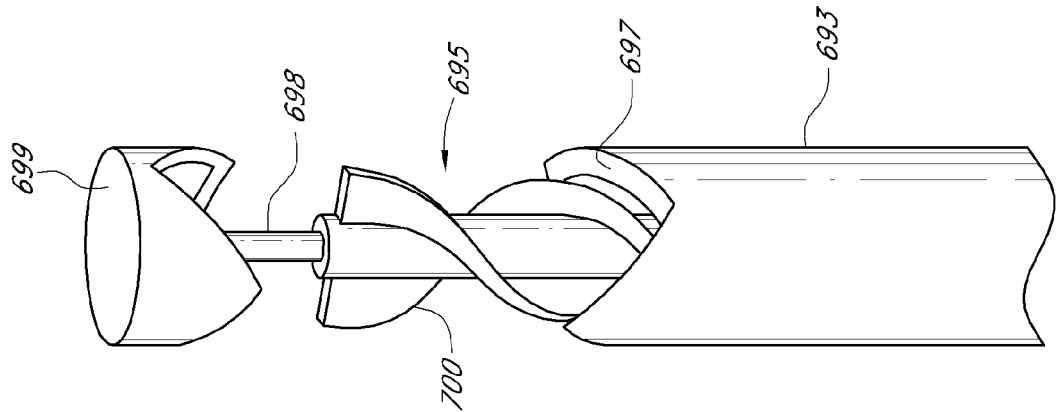
FIGS. 24(a) and 24(b) are fragmentary perspective views of a further embodiment of a tissue removal device constructed according to the teachings of the present invention, the tissue removal device being shown with its cutting element in partially open and fully open positions, respectively.
Figure 24A:
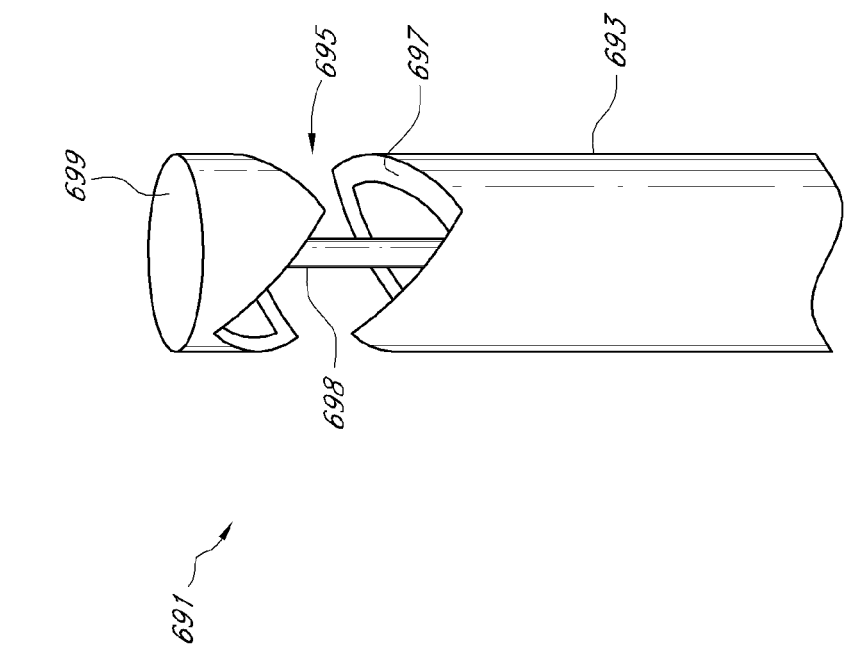

Referring now to FIGS. 24(*a*) and 24(*b*), there are shown fragmentary perspective views of a further embodiment of a tissue removal device constructed according to the teachings of the present invention, the tissue removal device being represented generally by reference numeral 691.

Device 691 may be similar in certain respects to device 541, with device 691 differing principally from device 541 in that device 691 may comprise the combination of a tubular member 693 and a grasping assembly 695 slidably mounted in tubular member 693, instead of the combination of tubular member 543 and grappling assembly 545. Tubular member 693 may be similar to tubular member 543, except that tubular member 693 may comprise a jagged distal end 697. Grasping assembly 695 may comprise a rotatable shaft 698, a cap 699 fixedly mounted on the distal end of shaft 698 and complementary in shape to distal end 697, and an auger 700 coaxially inserted over and mechanically coupled to shaft 698. In use, device 691 may be delivered transcervically to the uterus, preferably through the working channel of a hysteroscope, with assembly 695 in its proximal or retracted position, i.e., with cap 699 against the distal end 697 of tubular member 693. Next, assembly 695 may be moved distally relative to tubular member 693, and shaft 698 may be rotated (FIG. 24(b)). Assembly 695 may then be retracted towards tubular member 693, with tissue being grasped between cap 699 and jagged distal end 697. The tissue may then be severed as cap 699 mates with distal end 697. Suction may be applied to the proximal end (not shown) of tubular member 693 to draw tissue between cap 699 and distal end 697 and to move resected tissue proximally through tubular member 693. In addition, auger 700 may draw the resected tissue proximally through tubular member 693.

Figure 25B:
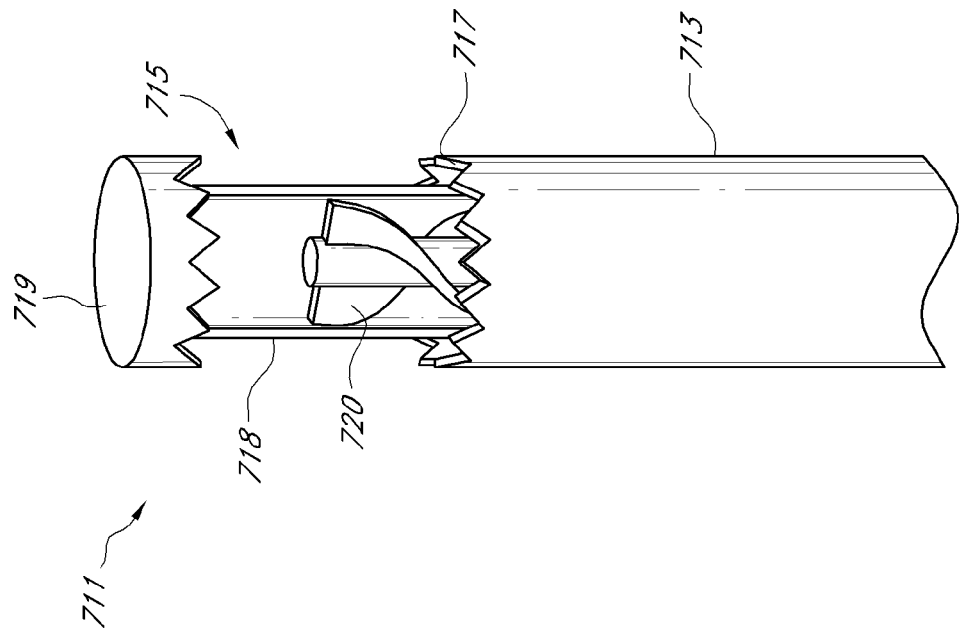
Figure 25A:
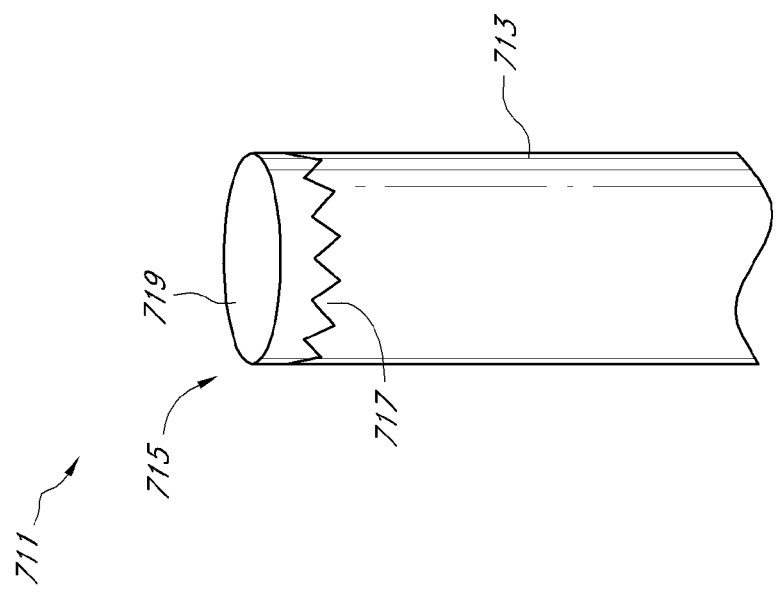

Referring now to FIGS. 25(a) and 25(b), there are shown fragmentary perspective views of a further embodiment of a tissue removal device constructed according to the teachings of the present invention, the tissue removal device being represented generally by reference numeral 711.

Device 711 may be similar in certain respects to device 691, with device 711 differing principally from device 691 in that device 711 may comprise the combination of a tubular member 713 and a grasping assembly 715 slidably mounted in tubular member 713, instead of the combination of tubular member 693 and grasping assembly 695. Tubular member 713 may be similar to tubular member 693, except that tubular member 713 may comprise a jagged distal end 717 having a greater number of teeth than distal end 697. Grasping assembly 715 may comprise a rotatable shaft 718 and a cap 719 fixedly mounted on the distal end of shaft 718, cap 719 being complementary in shape to distal end 717. In use, device 711 may be delivered transcervically to the uterus, preferably through the working channel of a hysteroscope, with assembly 715 in its proximal or retracted position, i.e., with cap 719 against the distal end 717 of tubular member 713 (FIG. 25(a)). Next, assembly 715 may be moved distally relative to tubular member 713, and shaft 718 may be rotated (FIG. 25(b)). Assembly 715 may then be retracted towards tubular member 713, with tissue being grasped between cap 719 and jagged distal end 717. The tissue may then be severed as cap 719 mates with distal end 717. Suction may be applied to the proximal end (not shown) of tubular member 713 to draw tissue between cap 719 and distal end 717 and to move resected tissue proximally through tubular member 713. In addition, an auger 720 may draw the resected tissue proximally through tubular member 713.

Figure 26:
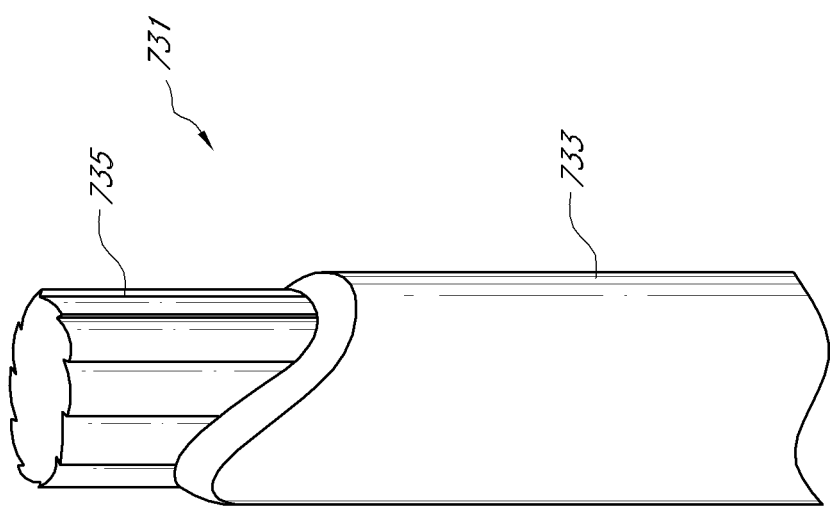
FIG. 26 is a fragmentary perspective view of a further embodiment of a tissue removal device constructed according to the teachings of the present invention, the tissue removal device being shown with its cutting element in its extended position.

Referring now to FIG. 26, there is shown a fragmentary perspective view of a further embodiment of a tissue removal device constructed according to the teachings of the present invention, the tissue removal device being represented generally by reference numeral 731.

Device 731 may be similar in certain respects to device 521, with device 731 differing principally from device 521 in that device 731 may comprise the combination of a tubular member 733 and a tubular milling cutter 735 slidably mounted in tubular member 733, instead of the combination of tubular member 523 and loop 525. In use, device 731 may be delivered transcervically to the uterus, preferably through the working channel of a hysteroscope, with cutter 735 in its proximal or retracted position within tubular member 733. Next, cutter 735 may be moved distally relative to tubular member 733, rotated about its longitudinal axis, and brought into contact with the tissue of interest, thereby severing the tissue. Suction may be applied to the proximal end (not shown) of tubular member 733 to draw tissue into cutter 735 and to move resected tissue proximally through cutter 735.

Figure 27B:
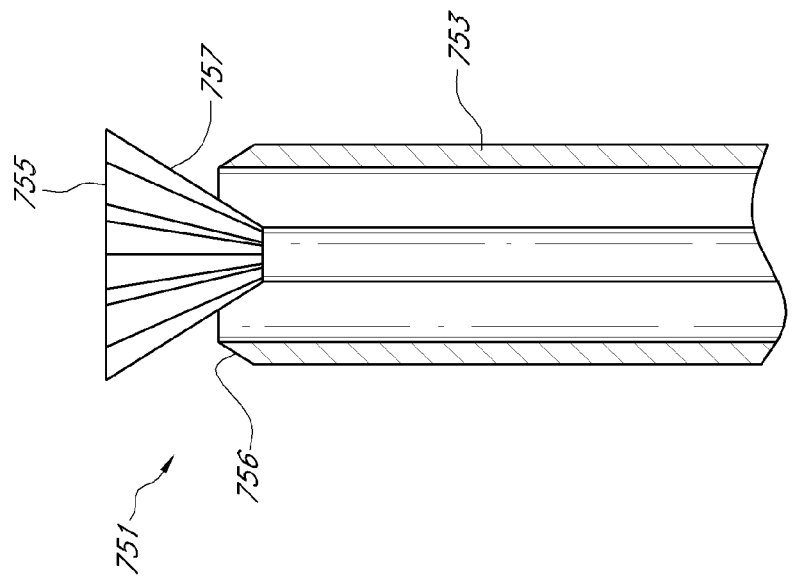
FIGS. 27(a) and 27(b) are fragmentary perspective and fragmentary side, partly in section, views, respectively, of a further embodiment of a tissue removal device constructed according to the teachings of the present invention, the tissue removal device being shown with its cutting element in its extended position.
Figure 27A:
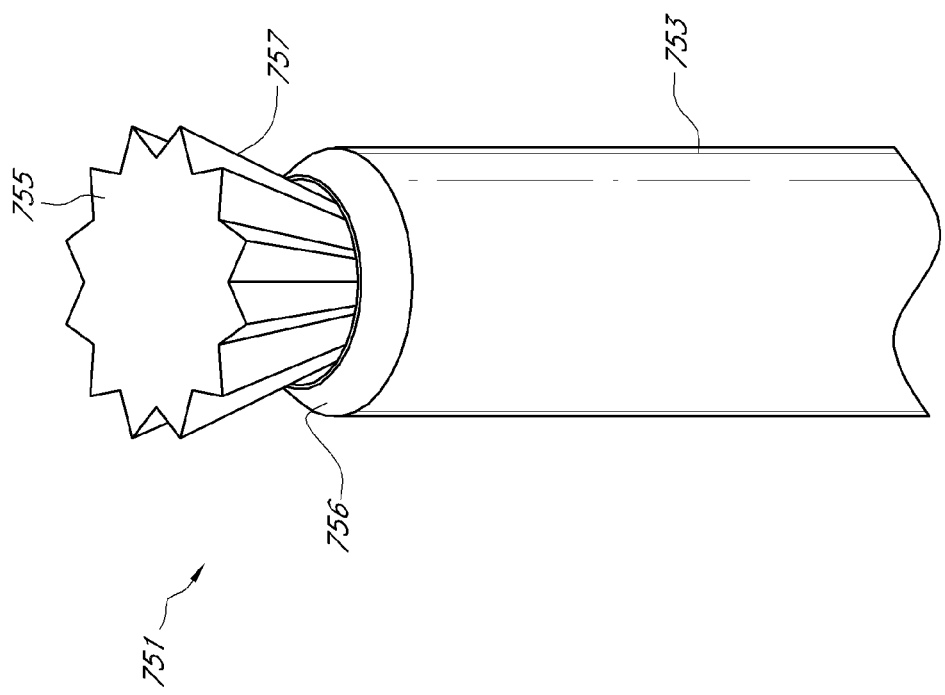

Referring now to FIGS. 27(a) and 27(b), there are shown fragmentary perspective and fragmentary side, partly in section, views, respectively, of a further embodiment of a tissue removal device constructed according to the teachings of the present invention, the tissue removal device being represented generally by reference numeral 751.

Device 751 may be similar in certain respects to device 731, with device 751 differing principally from device 731 in that device 751 may comprise the combination of a tubular member 753 and a tubular milling cutter 755 slidably mounted in tubular member 753, instead of the combination of tubular member 733 and tubular milling cutter 735. In particular, tubular member 753 may be similar to tubular member 733, except that tubular member 753 may comprise a distal end 756 having an external bevel. Cutter 755 may be similar to cutter 753, except that cutter 755 may comprise a beveled distal end 757. In use, device 751 may be delivered transcervically to the uterus, preferably through the working channel of a hysteroscope, with cutter 755 in its proximal position against tubular member 753. Next, tissue may be severed by contacting the tissue with cutter 755 while cutter is both rotated about its longitudinal axis and moved back and forth translationally. Suction may be applied to draw tissue into contact with cutter 755 and to remove resected tissue.

Figure 28:
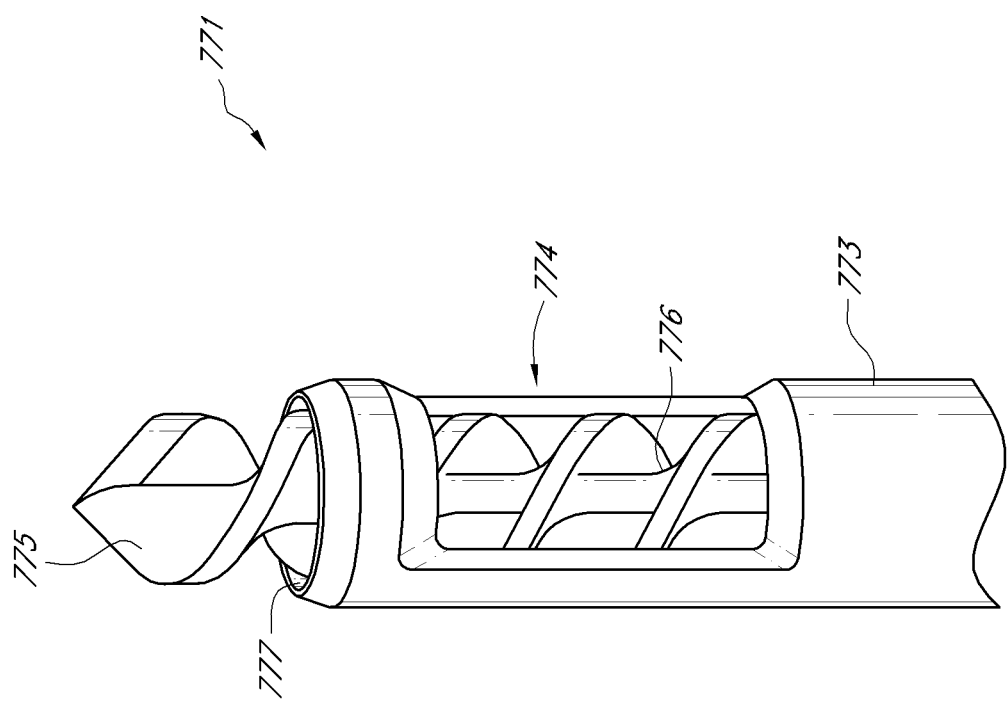
FIG. 28 is a fragmentary perspective view of a further embodiment of a tissue removal device constructed according to the teachings of the present invention, the tissue removal device being shown with its cutting element in its extended position.

Referring now to FIG. 28, there is shown a fragmentary perspective view of a further embodiment of a tissue removal device constructed according to the teachings of the present invention, the tissue removal device being represented generally by reference numeral 771.

Device 771 may be similar in certain respects to device 571, with device 771 differing principally from device 571 in that device 771 may comprise the combination of a tubular member 773 and a cutter 775, instead of the combination of tubular member 573 and cable 575. Tubular member 773, which may be similar to tubular member 573, may comprise a side window 774, a longitudinal lumen 776, and an open distal end 777. Cutter 775, which may comprise an auger, may be slidably disposed within lumen 776 of tubular member 773. In use, device 771 may be delivered transcervically to the uterus, preferably through the working channel of a hysteroscope, with cutter 775 positioned proximally within lumen 776. Next, tissue may be severed by moving cutter 775 distally beyond tubular member 773 and by bringing cutter 775 into contact with the tissue of interest while rotating cutter 775. Side window 774 may also be used for side cutting. Suction may be applied to the proximal end (not shown) of tubular member 773 to draw tissue towards cutter 775 and to move resected tissue proximally through tubular member 773. Resected tissue also may be moved through tubular member 773 by auger action.

Figure 29:
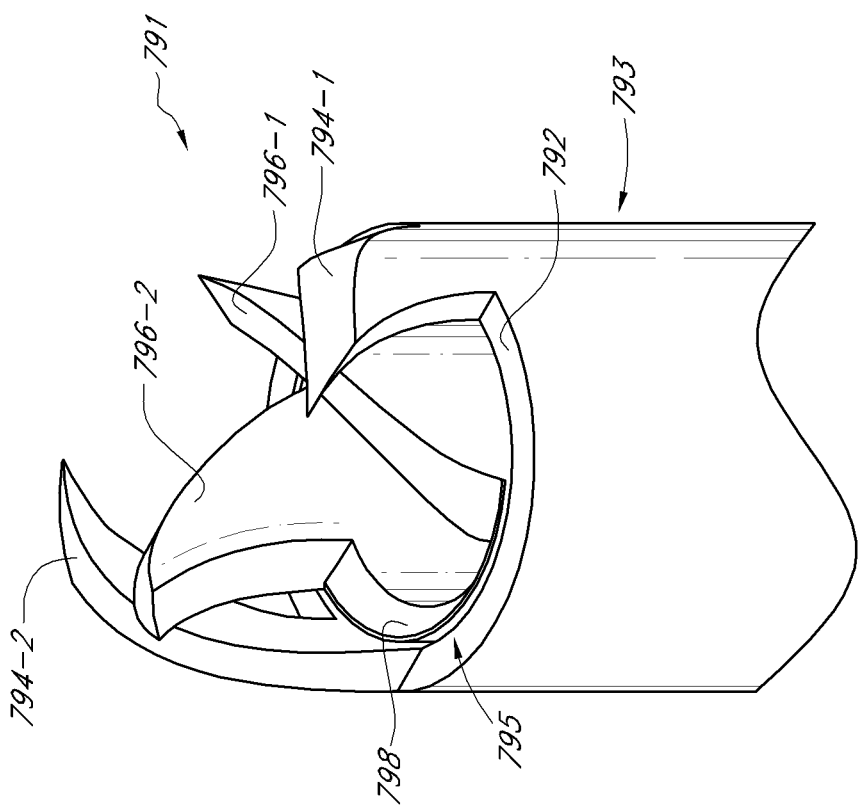
FIG. 29 is a fragmentary perspective view of a further embodiment of a tissue removal device constructed according to the teachings of the present invention.

Referring now to FIG. 29, there is shown a fragmentary perspective view of a further embodiment of a tissue removal device constructed according to the teachings of the present invention, the tissue removal device being represented generally by reference numeral 791.

Device 791 may be similar in certain respects to device 8, with device 791 differing principally from device 8 in that device 791 may comprise the combination of an outer tubular member 793 and an inner tubular member 795 rotatably mounted in tubular member 793, instead of the combination of outer tubular member 76 and inner tubular member 77. Tubular member 793 may be similar to tubular member 76, except that tubular member 793 may comprise a pair of curved blades 794-1 and 794-2 extending distally from its open distal end 792. Inner tubular member 795 may comprise a pair of curved blades 796-1 and 796-2 extending distally from its open distal end 798. In use, device 791 may be delivered transcervically to the uterus, preferably through the working channel of a hysteroscope, and brought into contact with the tissue of interest. Next, inner tubular member 795 is rotated relative to outer tubular member 793, causing tissue to be sheared in a scissor-like action as blades 796-1 and 796-2 slide past blades 794-1 and 794-2. Suction may be applied to the proximal end (not shown) of tubular member 793 to draw tissue into contact with blades 794 and blades 796 and to move resected tissue proximally through inner tubular member 795.

Figure 30:
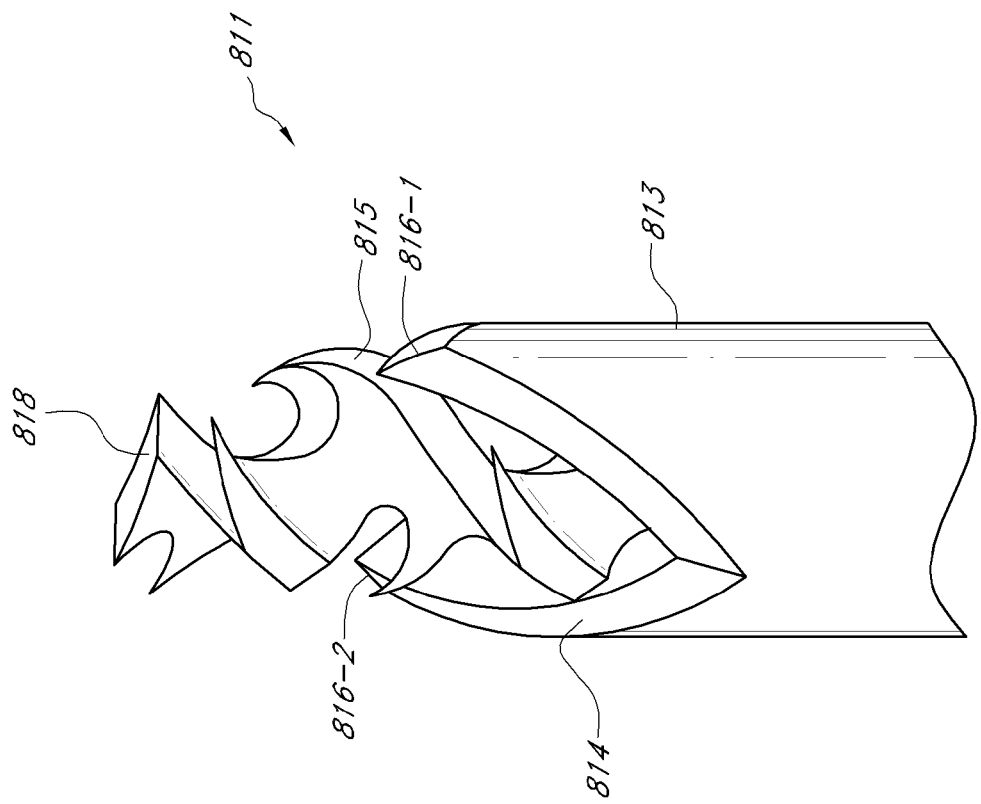
FIG. 30 is a fragmentary perspective view of a further embodiment of a tissue removal device constructed according to the teachings of the present invention.

Referring now to FIG. 30, there is shown a fragmentary perspective view of a further embodiment of a tissue removal device constructed according to the teachings of the present invention, the tissue removal device being represented generally by reference numeral 811.

Device 811 may be similar in certain respects to device 791, with device 811 differing principally from device 791 in that device 811 may comprise the combination of a tubular member 813 and a cutter 815 slidably mounted in tubular member 813, instead of the combination of outer tubular member 793 and inner tubular member 795. Tubular member 813 may be similar to tubular member 793, except that tubular member 813 may comprise a distal end 814 having a pair of sharpened points 816-1 and 816-2. Cutter 815, which may be rotated about its longitudinal axis, may comprise a jagged auger having a distal end 818. In use, device 811 may be delivered transcervically to the uterus, preferably through the working channel of a hysteroscope, with cutter 815 positioned in its proximal state, i.e., with distal end 818 within tubular member 813. Next, cutter 815 may be moved distally so that distal end 818 may be located distal to points 816-1 and 816-2. Cutter 815 may then be rotated as distal end 818 is brought into contact with the tissue of interest. Suction may be applied to the proximal end (not shown) of tubular member 813 to draw tissue into contact with cutter 818 and to move resected tissue proximally through tubular member 813.

Figure 31:
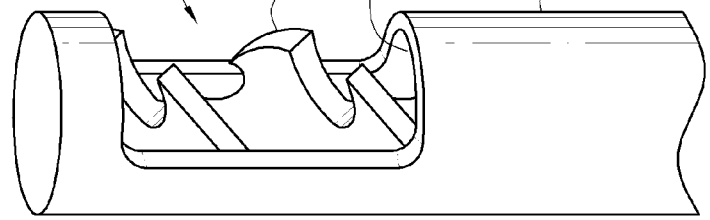
FIG. 31 is a fragmentary perspective view of a further embodiment of a tissue removal device constructed according to the teachings of the present invention.

Referring now to FIG. 31, there is shown a fragmentary perspective view of a further embodiment of a tissue removal device constructed according to the teachings of the present invention, the tissue removal device being represented generally by reference numeral 831.

Device 831 may be similar in certain respects to device 8, with device 831 differing principally from device 8 in that device 831 may comprise the combination of a tubular member 833 and a cutter 835 rotatably mounted in tubular member 833, instead of the combination of outer tubular member 76 and inner tubular member 77. Tubular member 833 may be similar to tubular member 76 and may comprise a side window 832 and a lumen 834. Cutter 835 may comprise a jagged auger. In use, device 831 may be delivered transcervically to the uterus, preferably through the working channel of a hysteroscope, and window 832 may be brought into contact with the tissue of interest. Next, cutter 835 may be rotated relative to tubular member 833, thereby causing tissue to be sheared and to be drawn, by auger action, proximally through lumen 834. Suction may be applied to the proximal end (not shown) of tubular member 833 to draw tissue through window 832 into contact with cutter 835 and to move resected tissue proximally through tubular member 833.

Figure 32:
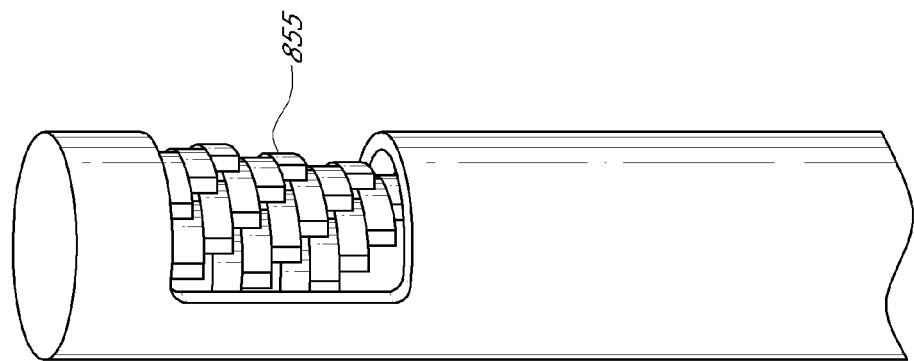
FIG. 32 is a fragmentary perspective view of a further embodiment of a tissue removal device constructed according to the teachings of the present invention.

A further embodiment of a tissue removal device is shown in FIG. 32 and is represented generally by reference numeral 851. Device 851 may be similar in most respects to device 831, with device 851 differing principally from device 831 in that device 851 may comprise a cutter 855, instead of cutter 835. Device 851 may be used in a similar fashion to device 831.

Figure 33:
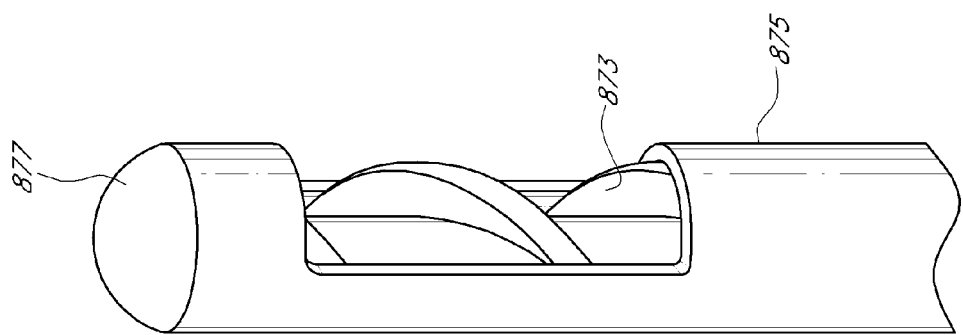
FIG. 33 is a fragmentary perspective view of a further embodiment of a tissue removal device constructed according to the teachings of the present invention.

A further embodiment of a tissue removal device is shown in FIG. 33 and is represented generally by reference numeral 871. Device 871 may be similar in most respects to device 831, with device 871 differing principally from device 831 in that device 871 may comprise a cutter 873, instead of cutter 835. In addition, device 871 may comprise a tubular member 875 and an electrocautery tip 877 that are similar to outer tubular member 453 and electrocautery tip 455, respectively, of device 451.

Figure 34:
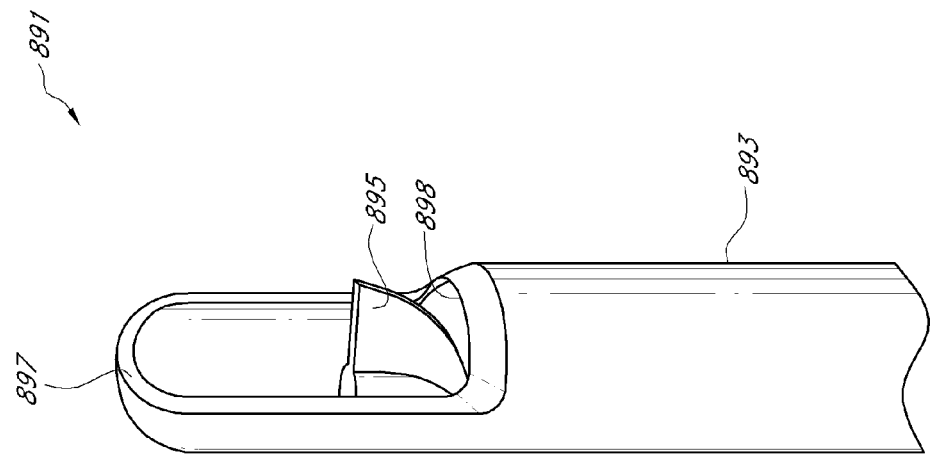
FIG. 34 is a fragmentary perspective view of a further embodiment of a tissue removal device constructed according to the teachings of the present invention.

A further embodiment of a tissue removal device is shown in FIG. 34 and is represented generally by reference numeral 891. Device 891 may be similar in certain respects to device 831, with device 891 differing principally from device 831 in that device 891 may comprise a tubular member 893 and a cutter 895, instead of tubular member 833 and cutter 835. Tubular member 893 may comprise a window 897 having a proximal cutting edge 898. Device 891 may be used in a similar fashion to device 831.

A further embodiment of a tissue removal device is shown in FIG. 35 and is represented generally by reference numeral 911. Device 911 may be similar in certain respects to device 831, with device 911 differing principally from device 831 in that device 911 may comprise a tubular member 913 and a serrated cutter 915, instead of tubular member 833 and cutter 835. Tubular member 913 may comprise a pair of windows 917-1 and 917-2 having sharp edges. Device 911 may be used in a similar fashion to device 831.

A further embodiment of a tissue removal device is shown in FIG. 36 and is represented generally by reference numeral 931. Device 931 may be similar in certain respects to device 8, with device 931 differing principally from device 8 in that device 931 may comprise an outer tubular member 933 and an inner tubular member 935, instead of outer tubular member 76 and inner tubular member 77. Outer tubular member 933 may be similar to outer tubular member 76, except that outer tubular member 933 may comprise a window 937 having sharp edges. Inner tubular member 935 may be similar to inner tubular member 77, except that inner tubular 935 may include a serrated slot 939 extending proximally a short distance from its distal end. Inner tubular member 935 may be rotated in one direction relative to outer tubular member 933 to cut tissue between slot 939 and window 937. Alternatively, inner tubular member 935 may be rotated in an oscillating fashion so that serrated slot 939 is alternately drawn past both side edges of window 937.

A further embodiment of a tissue removal device is shown in FIG. 37 and is represented generally by reference numeral 951. Device 951 may be similar in most respects to device 931, with device 951 differing principally from device 931 in that device 951 may comprise an inner tubular member 955, instead of inner tubular member 935. Inner tubular member 955 differs principally from inner tubular member 935 in that inner tubular member 955 includes a sharpened slot 959, as opposed to a serrated slot. Device 951 may be used in a similar fashion to device 931.

A further embodiment of a tissue removal device is shown in FIGS. 38(a) and 38(b) and is represented generally by reference numeral 971. Device 971 may be similar in certain respects to device 8, with device 971 differing principally from device 8 in that device 971 may comprise an outer tubular member 973 and an inner tubular member 975, instead of outer tubular member 76 and inner tubular member 77. Outer tubular member 973 may comprise a window 977 having sharpened proximal and distal ends 978-1 and 978-2, respectively. Inner tubular member 975, which may oscillate translationally relative to outer tubular member 973 but not rotate relative to outer tubular member 973, may include a pair of windows 979-1 and 979-2 separated by a band 980 having sharpened edges 981-1 and 981-2. In use, as inner tubular member 975 moves translationally relative to outer tubular member 973, tissue present between edges 981-1 and 981-2 of band 980 and ends 978-1 and 978-2 of window 977 may be cut. The cut tissue is then drawn into inner tubular member 975 through windows 979-1 and 979-2 and removed proximally through inner tubular member 975 by suction.

Figure 39:
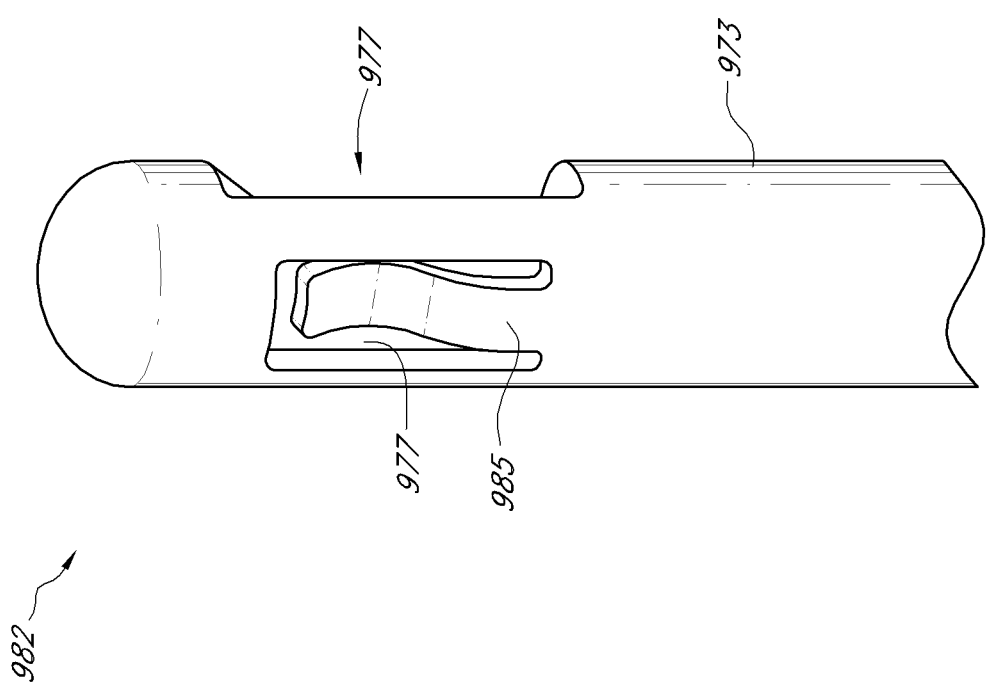
FIG. 39 is a fragmentary perspective view of a further embodiment of a tissue removal device constructed according to the teachings of the present invention.

As can be appreciated, the efficiency of cutting in devices like device 971 may be impaired if the complementary cutting surfaces, e.g., edges 981-1 and 981-2 of band 980 and ends 978-1 and 978-2 of window 977 in device 971, do not have tight tolerances. One solution to this problem is illustrated in FIG. 39, which shows a tissue removal device 982 that may comprise an outer tubular member 983 having an integral spring tab 985 to bias inner tubular member 975 towards window 977. In another embodiment (not shown), the outer tubular member may be crimped inwardly near window 977.

Figure 40:
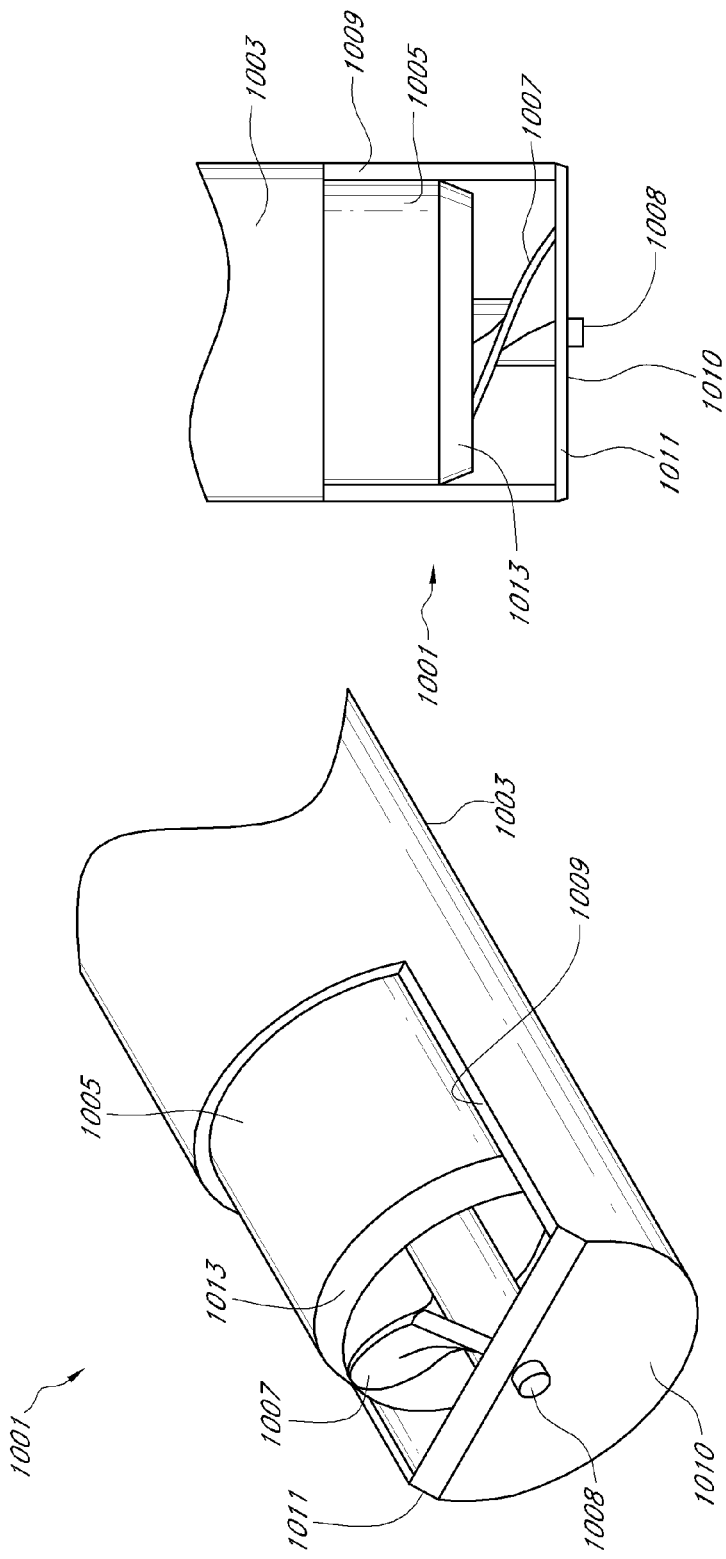
FIGS. 40(a) and 40(b) are fragmentary perspective and fragmentary side views, respectively, of a further embodiment of a tissue removal device constructed according to the teachings of the present invention.

Referring now to FIGS. 40(a) and 40(b), there are shown fragmentary perspective and fragmentary side views, respectively, of a further embodiment of a tissue removal device constructed according to the teachings of the present invention, the tissue removal device being represented generally by reference numeral 1001.

Device 1001 may be similar in certain respects to device 8, with device 1001 differing principally from device 8 in that device 1001 may comprise the combination of an outer tubular member 1003, an inner tubular member 1005 and an auger 1007, instead of the combination of outer tubular member 76 and inner tubular member 77. Outer tubular member 1003 may comprise a window 1009 extending proximally a short distance from its distal end 1010. The distal edge 1011 of window 1009 may be beveled to provide a cutting surface. Inner tubular member 1005, which may be rotatably, but not slidably, disposed within outer tubular member 1003, may comprise an open distal end 1013 having an external bevel. Distal end 1013 of inner tubular member 1005 may be spaced from distal end 1010 of outer tubular member 1003 by approximately 0.25 mm to 1.5 mm. Auger 1007, which may be rotatably, but not slidably, disposed within inner tubular member 1005, may comprise a distal end 1008 rotatably mounted on distal end 1010 of outer tubular member 1003. Inner tubular member 1005 and auger 1007 may be rotated at different speeds relative to each other, with inner tubular member 1005 preferably rotated at about 30 to 3000 rpm, and inner tubular member 1005 preferably rotated at about 30 to 300 rpm. Inner tubular member 1005 may be rotated either clockwise or counterclockwise. Device 1001 may be operated without using a vacuum, with auger 1007 serving to move severed tissue and other matter proximally through inner tubular member 1005.

Figure 41:
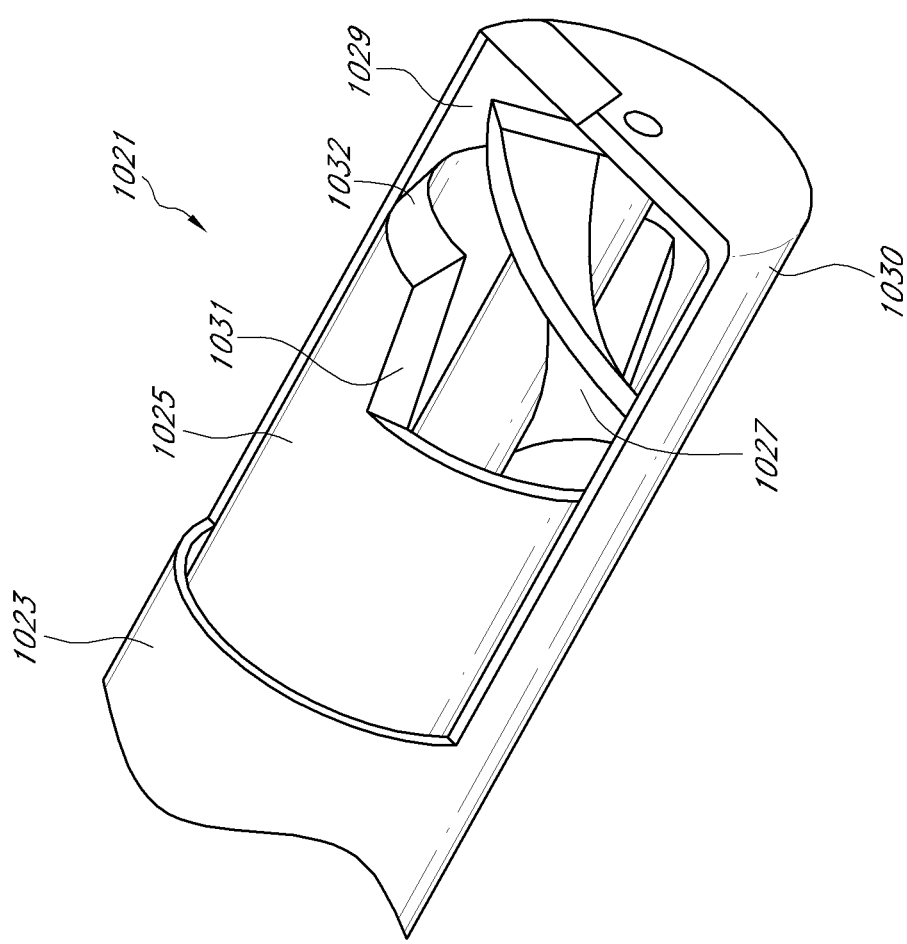
FIG. 41 is a fragmentary perspective view of a further embodiment of a tissue removal device constructed according to the teachings of the present invention.

An alternate embodiment to tissue removal device 1001 is shown in FIG. 41 and is represented generally by reference numeral 1021. Device 1021 may differ principally from device 1001 in that device 1021 may comprise an outer tubular member 1023, an inner tubular member 1025 and an auger 1027, instead of outer tubular member 1003, inner tubular member 1005, and auger 1007. Outer tubular member 1023 may differ from outer tubular member 1003 in that outer tubular member 1023 may include a window 1029 having a distal edge 1030. Inner tubular member 1025 may differ from inner tubular member 1005 in that inner tubular member 1025 may include a cutting window 1031 extending proximally a short distance from its distal end 1032. Auger 1027 may differ in shape from auger 1007. Auger 1027 and inner tubular member 1025 may rotate in the same or opposite directions.

Further alternate embodiments to device 1001 are shown in FIGS. 42 through 46. More specifically, in FIG. 42, there is shown a tissue removal device 1051, which may differ primarily from device 1001 in that inner tubular member 1005 and auger 1007 of device 1001 may be replaced with a plurality of blades 1052 and a shaft 1053, respectively, blades 1052 being coupled to shaft 1053 for rotation within an outer tubular member 1055 to provide a whisk-like cutting action. In FIG. 43, there is shown a tissue removal device 1056 that may be similar to device 1051, except for the shape of its blades 1057 and for the shape of the window 1058 of its outer tubular member 1057. In FIG. 44, there is shown a tissue removal device 1061 that may comprise an outer tubular member 1063, a rotatable inner tubular member 1065, and a retractable pincher-type grasper 1067. In FIG. 45, there is shown a tissue removal device 1071 that may comprise an outer tubular member 1073, a rotatable inner tubular member 1075, and a retractable corkscrew-type grasper 1077. In FIG. 46, there is shown a tissue removal device 1081 that may comprise an outer tubular member 1083, a rotatable inner tubular member 1085, and an auger 1087.

Figure 47:
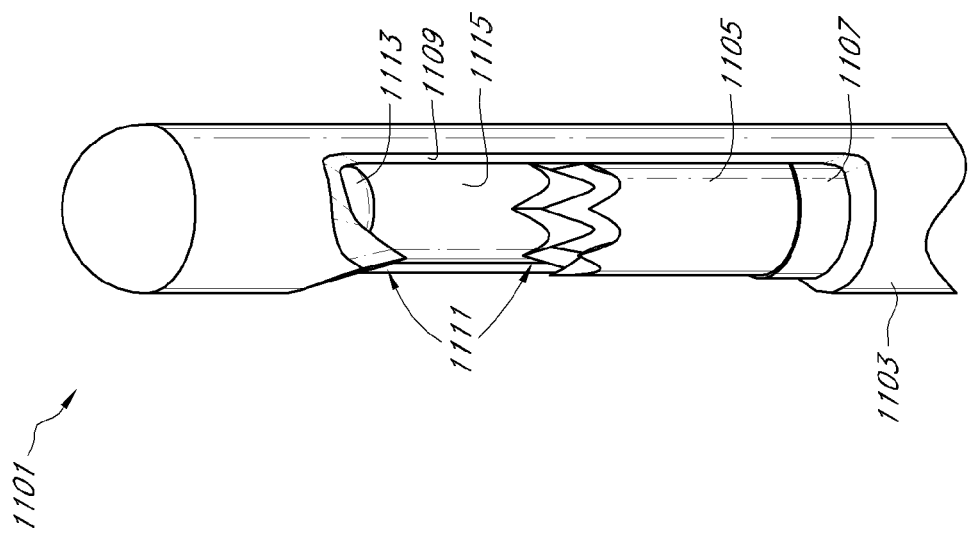
FIG. 47 is a fragmentary perspective view of a further embodiment of a tissue removal device constructed according to the teachings of the present invention.

Referring now to FIG. 47, there is shown a fragmentary perspective view of a further embodiment of a tissue removal device constructed according to the teachings of the present invention, the tissue removal device being represented generally by reference numeral 1101.

Device 1101 is similar in many respects to device 8, with device 1101 differing principally from device 8 in that device 1101 may comprise the combination of an outer tubular member 1103, an inner tubular member 1105, and a shield 1107, instead of an outer tubular member 76 and an inner tubular member 77. Outer tubular member 1103 may be similar to outer tubular member 76, except that outer tubular member 1103 may comprise a window 1109 shaped to include a pointed tip 1111 at its distal edge and may further comprise a block 1113 disposed within its lumen 1115 to provide a chopping surface against which inner tubular member 1105 may strike. Inner tubular member 1105 may be shaped to include a jagged distal end 1117. Shield 1107 may be slidably mounted within outer tubular member 1103 to permit the size of window 1109 to be adjusted. Device 1101 may be operated similarly to device 8.

Figure 48:
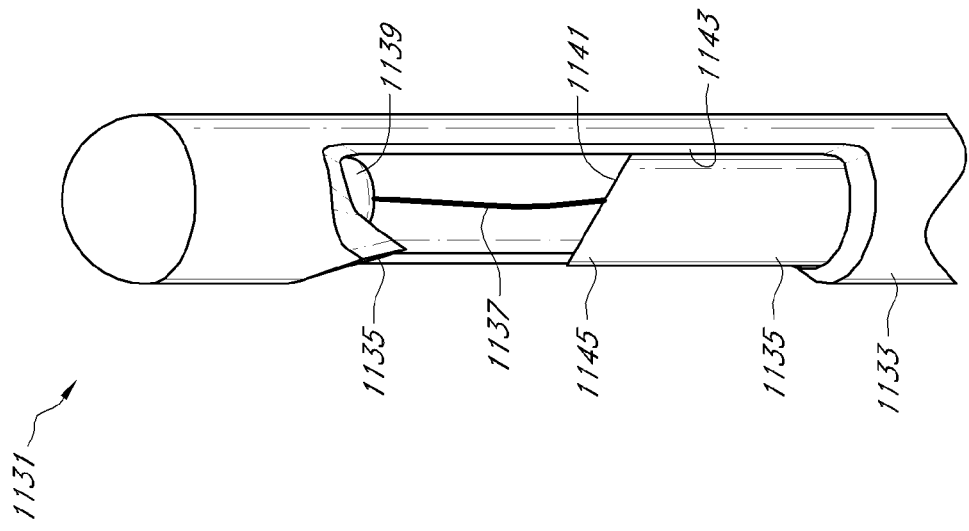
FIG. 48 is a fragmentary perspective view of a further embodiment of a tissue removal device constructed according to the teachings of the present invention.

A further embodiment of a tissue removal device is shown in FIG. 48 and is represented generally by reference numeral 1131. Device 1131 may be similar in certain respects to device 971, with device 1131 differing principally from device 971 in that device 1131 may comprise an outer tubular member 1133 and an inner tubular member 1135, instead of outer tubular member 973 and inner tubular member 975. Outer tubular member 1133 may be similar to outer tubular member 973, except that outer tubular member 1133 may comprise an outwardly-biased pivotable pawl 1135 coupled to a pull-wire 1137 and may further comprise a block 1139 disposed within a lumen 1141 to provide a chopping surface against which inner tubular member 1135 may strike. Pawl 1135 may be used to grasp tissue, which may then be pulled in towards a window 1143 by pulling on pull-wire 1137. Inner tubular member 1135, which may oscillate translationally but may not rotate, may comprise a beveled distal end 1145.

Further embodiments of a tissue removal device according to the present invention are shown in FIGS. 49 through 54. More specifically, in FIG. 49, there is shown a fragmentary perspective view of a tissue removal device 1151. Device 1151 may comprise an outer tubular member 1153 and an inner tubular member 1155. Outer tubular member 1153 may comprise a side window 1157 and an open distal end 1159. Inner tubular member 1155, which may comprise an open distal end 1161 having an internal bevel, may be rotatable within outer tubular member 1153. At the same time that it rotates, inner tubular member 1155 may oscillate back and forth so that distal end 1161 moves between a proximal position in front of window 1157 and a distal position distal to distal end 1159. In this manner, device 1151 may be used to cut tissue using window 1157 or using only the distal end 1161 of inner tubular member 1155.

In FIG. 50, there is shown a fragmentary perspective view of a tissue removal device 1171. Device 1171 may comprise an outer tubular member 1173 and a cutting assembly 1175. Outer tubular member 1173 may comprise an open distal end 1174. Cutting assembly 1175 may be slidably mounted in outer tubular member 1173 and may include a distal end cap 1176 that may be positioned distally beyond distal end 1174. Cutting assembly 1175 may comprise a stationary serrated blade 1177 fixed to distal end cap 1175 and a movable serrated blade 1178 coupled to motor means (not shown) for reciprocating blade 1178 alongside of blade 1177 so that blades 1177 and 1178 work together to cut tissue.

In FIG. 51, there is shown a side view of a tissue removal device 1191. Device 1191 may include a tubular member 1192 and a milling member 1193. Tubular member 1192 may comprise a side window 1194 and a lumen 1195. Milling member 1193 may be rotatable within lumen 1195 and may oscillate back and forth within lumen 1195 across window 1194.

In FIG. 52, there is shown a fragmentary perspective view of a tissue removal device 1201. Device 1201 may comprise a tubular member 1203 and an electrocautery loop 1205. A gaffing hook 1207 for grabbing tissue may be fixed to loop 1205.

In FIGS. 53(a) and 53(b), there are shown fragmentary perspective and fragmentary section views of a tissue removal device 1221. Device 1221 may comprise an outer tubular member 1223 having a sharpened distal end 1224 and an inner tubular member 1225 having a sharpened distal end 1226, inner tubular member 1225 being rotatably mounted within outer tubular member 1223 to create a shearing effect at distal ends 1224 and 1226.

Figure 54:
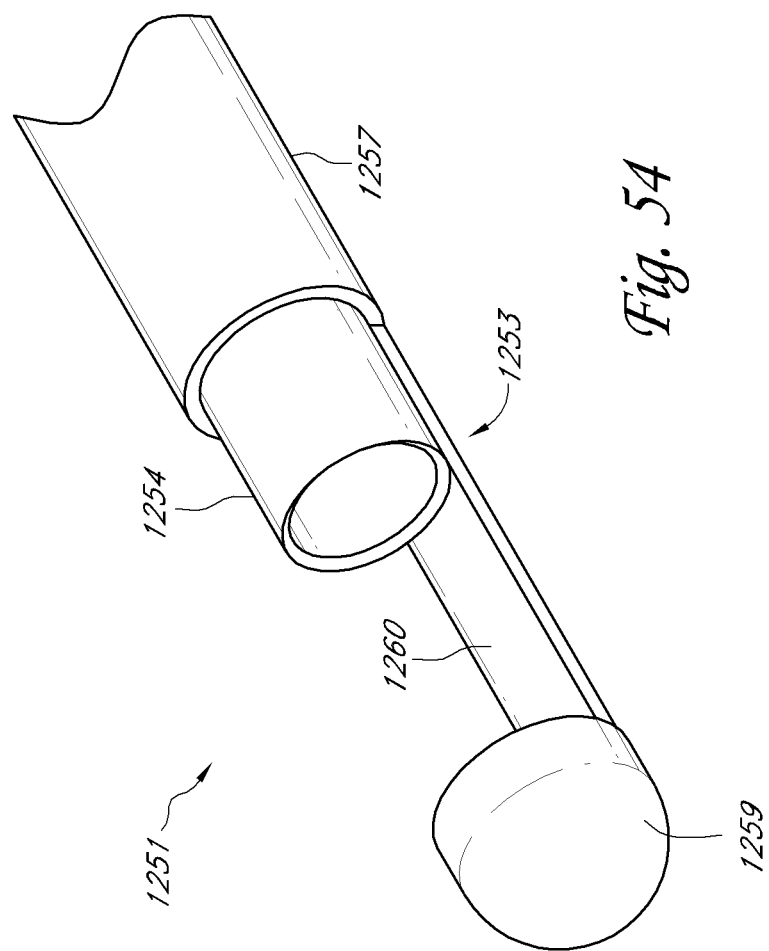
FIG. 54 is a fragmentary perspective view of a further embodiment of a tissue removal device constructed according to the teachings of the present invention.

In FIG. 54, there is shown a fragmentary perspective view of a tissue removal device 1251. Device 1251 may comprise an outer tubular member 1253 and an inner tubular member 1254, inner tubular member 1254 being slidably and rotatably mounted within outer tubular member 1253. Outer tubular member 1253 may comprise a proximal portion 1257 and a distal tip 1259, distal tip 1259 being coupled to proximal portion 1257 by a flexible bridge 1260. Bridge 1260 may permit tip 1259 to deflect away from proximal portion 1257, thereby maximizing the amount of tissue that may be drawn between tip 1259 and proximal portion 1257.

A series of experiments were conducted to evaluate the effect of differing translations speeds of the cutter, vacuum pressure and rotation speeds of the cutter. The data are reported in FIGS. 55 through 57. In these experiments, the outer geometry of the cutter was built in accordance with the design illustrated in FIG. 4A and the inner geometry of the cutter was constructed in accordance with FIG. 5A.

Referring to the data of FIG. 55, translation speeds were maintained at 2.8 cycles/sec and vacuum pressure was maintained at 600 mm Hg for all experiments. Experiments were run at rotation speeds of 1000, 3000, 6000 and 7500 rpm.

The data reported in FIG. 56 is from a series of experiments in which rotational speed was maintained at 6000 rpm and vacuum pressure was maintained at 600 mm Hg. Experiments were conducted at translation speeds of 1.2 and 4.4 cycles/sec.

The data in FIG. 57 was obtained through a series of experiments in which rotation speed was maintained at 6000 rpm and translation speed was maintained at 2.8 cycles/sec. Vacuum pressure was maintained at 300 mm Hg for two experiments and 450 mm Hg for two experiments.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A uterine fibroid tissue removal device, comprising:
   an elongate outer tubular member having an outside diameter of no more than about 3.5 mm, the outer tubular member including a tissue receiving side window configured to receive uterine fibroid tissue to be severed from a uterus wall;
   an inner tubular member positioned within the outer tubular member, the inner tubular member comprising a proximal end, an open distal end, and a tissue aspiration lumen extending therebetween;
   a translational drive configured to oscillate the inner tubular member translationally along a longitudinal axis of the inner tubular member, such that the open distal end of the inner tubular member oscillates translationally across the tissue receiving side window of the outer tubular member to thereby sever uterine fibroid tissue extending therethrough; and
   a rotational drive that rotates the inner tubular member at a rate of at least 5000 revolutions per minute about the longitudinal axis of the inner tubular member while the inner tubular member oscillates translationally across the tissue receiving side window, such that the device is capable of removing uterine fibroid tissue severed by the inner tubular member at a rate of at least about 1.8 gm/min.

2. The tissue removal device of claim 1, wherein
   the rotational drive comprises a rotational driving mechanism mechanically coupling a first drive shaft to the inner tubular member to transfer rotational energy from the first drive shaft to the inner tubular member to thereby rotate the inner tubular member about the longitudinal axis of the inner tubular member; and wherein
   the translational drive comprises an oscillating translational driving mechanism mechanically coupling a second drive shaft to the inner tubular member to transfer translating energy from the second drive shaft to the inner tubular member to thereby oscillate translationally the inner tubular member along the longitudinal axis of the inner tubular member.

3. The tissue removal device of claim 1, further comprising a vacuum source in communication with the tissue aspiration lumen of the inner tubular member.

4. The tissue removal device of claim 1, wherein at least a portion of the outer tubular member is flexible.

5. The tissue removal device of claim 4, wherein at least a portion of the inner tubular member is flexible.

6. The tissue removal device of claim 1, further comprising a housing coupled to the outer tubular member.

7. The tissue removal device of claim 6, wherein the outer tubular member is coupled to the housing in a non-coaxial manner.

8. The tissue removal device of claim 1, wherein the rotational drive rotates the inner tubular member at a rate of approximately 6000 revolutions per minute, and the translational drive is configured to translationally oscillate the inner tubular member at a rate of approximately 240 cycles per minute.

9. The tissue removal device of claim 8, wherein an advance ratio equal to a ratio of the rate of oscillation to the rate of rotation of the inner tubular member is less than 0.25.

10. The tissue removal device of claim 1, wherein the open distal end of the inner tubular member has an external bevel.

11. The tissue removal device of claim 1, wherein the tissue receiving side window on the outer tubular member has sloped or jagged distal and proximal ends.

* * * * *